United States Patent
Soper et al.

(10) Patent No.: US 12,280,374 B2
(45) Date of Patent: Apr. 22, 2025

(54) NANOFLUIDIC ANALYTICAL DEVICES AND METHODS OF USING THEREOF

(71) Applicants: UNIVERSITY OF KANSAS, Lawrence, KS (US); THE UNIVERSITY OF NORTH CAROLINA AT CHAPEL HILL, Chapel Hill, NC (US); BOARD OF SUPERVISORS OF LOUISIANA STATE UNIVERSITY AND AGRICULTURAL AND MECHANICAL COLLEGE, Baton Rouge, LA (US); NORTHEASTERN UNIVERSITY, Boston, MA (US); CLARKSON UNIVERSITY, Potsdam, NY (US)

(72) Inventors: Steven A. Soper, Baton Rouge, LA (US); Collin J. McKinney, Durham, NC (US); Elizabeth Podlaha-Murphy, Potsdam, NY (US); Sunggook Park, Baton Rouge, LA (US)

(73) Assignees: University of Kansas, Lawrence, KS (US); Univ. of N Carolina at Chapel Hill, Chapel Hill, NC (US); Board of Supervisors of LSU and A&M College, Baton Rouge, LA (US); Northeastern University, Boston, MA (US); Clarkson University, Potsdam, NY (US)

( * ) Notice: Subject to any disclaimer, the term of this patent is extended or adjusted under 35 U.S.C. 154(b) by 1015 days.

(21) Appl. No.: 17/260,125

(22) PCT Filed: Jul. 15, 2019

(86) PCT No.: PCT/US2019/041872
§ 371 (c)(1),
(2) Date: Jan. 13, 2021

(87) PCT Pub. No.: WO2020/014708
PCT Pub. Date: Jan. 16, 2020

(65) Prior Publication Data
US 2021/0268503 A1   Sep. 2, 2021

Related U.S. Application Data

(60) Provisional application No. 62/714,507, filed on Aug. 3, 2018, provisional application No. 62/697,916, filed on Jul. 13, 2018.

(51) Int. Cl.
*B01L 3/00*   (2006.01)
*C12Q 1/6869*   (2018.01)
*G01N 33/68*   (2006.01)

(52) U.S. Cl.
CPC ... *B01L 3/502761* (2013.01); *B01L 3/502715* (2013.01); *C12Q 1/6869* (2013.01);
(Continued)

(58) Field of Classification Search
None
See application file for complete search history.

(56) References Cited

U.S. PATENT DOCUMENTS 6,489,121 B1   12/2002   Skilling
9,017,937 B1   4/2015   Turner et al.
(Continued)

FOREIGN PATENT DOCUMENTS

WO   WO2005/076837   8/2005
WO   WO/2013/012440   1/2013
(Continued)

OTHER PUBLICATIONS

Kondylis et al., "Nanofluidic Devices with 8 Pores in Series for Real-Time, Resistive-Pulse Analysis of Hepatitis B Virus Capsid Assembly", Anal. Chem., 2017, 89, 4855-4862 (Year: 2017).*
(Continued)

*Primary Examiner* — Samuel P Siefke
*Assistant Examiner* — Henry H Nguyen
(74) *Attorney, Agent, or Firm* — Dickinson Wright PLLC

(57) ABSTRACT

Disclosed are nanofluidic analytical devices. The devices employ a sample processing region that includes a plurality
(Continued)

of fluidically connected sample handling elements that, in combination, affect a physical change on a sample introduced into the sample processing region. This physical change can include, for example, purification of an analyte of interest present in the sample, concentration of an analyte of interest present in the sample, chemical modification (e.g., cleavage and/or chemical derivatization) of an analyte of interest present in the sample, or a combination thereof. The analytical devices further include a nanochannel comprising a plurality of in-plane nanopores in series fluidically coupled to the sample processing region. The in-plane nanopores can be used to detect and/or analyze analyte(s) present in the sample following processing by the sample processing region. These analytical devices can advantageously provide for the label-free detection of single molecules.

18 Claims, 33 Drawing Sheets

(52) U.S. Cl.
CPC .. *G01N 33/6818* (2013.01); *B01L 2200/0652* (2013.01); *B01L 2300/0645* (2013.01); *B01L 2300/0896* (2013.01); *B01L 2400/0415* (2013.01); *B01L 2400/0421* (2013.01)

(56) References Cited

U.S. PATENT DOCUMENTS

| | | | |
|---|---|---|---|
| 9,738,927 | B2 | 8/2017 | So |
| 9,909,173 | B2 | 3/2018 | Soper et al. |
| 10,393,726 | B2 | 8/2019 | Soper et al. |
| 10,830,757 | B2 | 11/2020 | Soper et al. |
| 2007/0190546 | A1 | 8/2007 | Siddiqi et al. |
| 2012/0129716 | A1 | 5/2012 | Chee et al. |
| 2012/0245047 | A1 | 9/2012 | Craighead et al. |
| 2015/0361489 | A1 | 12/2015 | Soper et al. |
| 2017/0298432 | A1 | 10/2017 | Holt |
| 2018/0074039 | A1* | 3/2018 | Soper ............... B01L 3/502761 |
| 2018/0188230 | A1 | 7/2018 | Huff et al. |

FOREIGN PATENT DOCUMENTS

| | | |
|---|---|---|
| WO | 2014/124365 | 8/2014 |
| WO | 2016/154302 | 9/2016 |

OTHER PUBLICATIONS

Adams et al., "Highly Efficient Circulating Tumor Cell Isolation From Whole Blood and Label-Free Enumeration Using Polymer-Based Microfluidics With an Integrated Conductivity Sensor," *J. Am. Chem. Soc.* 130:8633-8641 (2008).
Chen et al., "Functional Template-Derived Poly(methyl methacrylate) Nanopillars for Solid-Phase Biological Reactions," *Chem. Mater.* 19:3855-3857 (2007).
Dapprich, J., "Single-Molecule DNA Digestion by Lambda-Exonuclease," *Cytometry* 36:163-168 (1999).
Dharmasiri et al., "Capture and Enumeration of LNCaP Prostate Cancer Cells Using Aptamers Immobilized to a PMMA Microsampling Unit," *Electrophoresis* 30:3289-3300 (2009).
Galloway et al., "Contact Conductivity Detection in Poly(methyl methacylate)-Based Microfluidic Devices for Analysis of Mono- and Polyanionic Molecules," *Anal. Chem.* 74:2407-2415 (2002).
Geisler and Coller, "XRN1: A Major 5' to 3' Exoribonuclease in Eukaryotic Cells," *Enzymes* 31:97-110 (2012).
Han and Craighead, "Separation of Long DNA Molecules in Microfabricated Entropic Trap Array," *Science* 288: 1026-1029 (2000).

Hashimoto et al., "Ligase Detection Reaction/Hybridization Assays Using Three-Dimensional Microfluidic Networks for the Detection of Low-Abundant DNA Point Mutations," *Analytical Chemistry* 77:3243-3255 (2005).
Hashimoto et al., "Rapid PCR in a Continuous Flow Device," *Lab on A Chip* 4:638-645 (2004).
Henry & McCarley, "Selective Deposition of Metals on Plastics Used in the Construction of Microanalytical Devices: Photo-Directed Formation of Metal Features on PMMA," *J. Phys. Chem. B* 105:8755-8761 (2001).
Henry et al., "Surface Modification of Poly(methyl methacrylate) Used in the Fabrication of Microanalytical Devices," *Anal. Chem.* 72:5331-5337(2000).
Henry, A. C., "Surface Modification and Characterization of PMMA Used in the Construction of Microelectromechanical Systems," *In Chemistry*, p. 147, Louisiana State University, Baton Rouge (2001).
Jinek et al., "Coupled 5' Nucleotide Recognition and Processivity in Xrn1-Mediated mRNA Decay," *Mol. Cell* 41:600-608 (2011).
Johnson & Martin, "Controlling Protein Orientation at Interfaces Using Histidine Tags: An Alternative to Ni/NTA," *J. Am. Chem. Soc.* 127:2018-2019 (2005).
Jones et al., "The 5'→3' Exoribonuclease XRN1/Pacman and its Functions in Cellular Processes and Development," *WIREs RNA* 3:455-468 (2012).
Lee et al., Elastic Coupling Between RNA Degradation and Unwinding by an Exoribonuclease, *Science* 336:1726-1729 (2012).
McCarley et al., "Resist-Free Patterning of Surface Architectures in Polymer-Based Microanalytical Devices," *J. Am. Chem. Soc.* 127:842-843 (2005).
O'Donnell et al., "Pressure-driven DNA Transport Across an Artificial Nanotopography," *New Journal of Physics* 11: 075032 (2009).
Park et al., "A Titer Plate-Based Polymer Microfluidic Platform for High Throughput Nucleic Acid Purification," *Biomedical Microdevices* 10:21-33 (2008).
Perkins et al., "Sequence-Dependent Pausing of Single Lambda Exonuclease Molecules," *Science* 301:1914-1918 (2003).
Reisner et al., "Direct Self-Organization of Single DNA Molecules in a Nanoslit via Embedded Nanopt Arrays," *Proc. Natl. Acad. Sci. USA* 106: 79-84 (2009).
Smith et al., "Measurement of Protein Using Bicinchoninic Acid," *Anal. Biochem.* 150:76-85 (1985).
Stoscheck, C. M., "Quantitation of Protein," *Methods in Enzymol.* 182:50-68 (1990).
Vaidya et al., "Surface Modification and Characterization of Microfabricated Poly(carbonate) Devices: Manipulation of Electroosmotic Flow," *Analyst* 127:1289-1292 (2002).
Wang et al., "Microarrays Assembled in Microfluidic Chips Fabricated From Poly(methyl methacrylate) for the Detection of Low-Abundant DNA Mutations," *Anal. Chem.* 75:1130-1140 (2003).
Warden et al., "Synthesis of Novel Derivatives of 1,4,7-Triazacyclononane," *Organic Lett.* 3:2855-2858 (2001).
Wei et al., Photochemically Patterned Poly(methyl methacrylate) Surfaces Used in the Fabrication of Microanalytical Devices. *J. Phys. Chem. B* 109:16988-16996 (2005).
Wei, S., "Multianalyte Detection of Breast Cancer by Fabrication of Hybridmicroarrays on Polymer-based Microanalytical Devices," Louisiana State University, Baton Rouge (2006).
Witek et al., "96-Well Polycarbonate-Based Microfluidic Titer Plate for High-Throughput Purification of DNA and RNA," *Analytical Chemistry* 80:3483-3491 (2008).
Xu et al., "Polymer Microfluidic Chips with Integrated Waveguides for Reading Microarrays," *Analytical Chemistry* 79:9007-9013 (2007).
Zuo et al., "Structural Basis for Processivity and Single-Strand Specificity of RNaseII," *Mol. Cell* 24:149-156 (2006).
International Search Report and Written Opinion for International Application No. PCT/US2014/15574 dated May 14, 2014.
Uba, Franklin I. et al. "Nanogap electrical detection of single molecules translocating through a nanochannel with transverse nanoelectrodes and funnels populated with an array of nanopillars." (2011). 15th International Conference on Miniaturized Systems for Chemistry and Life Sciences Oct. 2-6, 2011, Seattle, Washington, USA.

(56) References Cited

OTHER PUBLICATIONS

International Search Report and Written Opinion for International Application No. PCT/US2019/041872 dated Nov. 18, 2019.

* cited by examiner

Top pore: 50 nm width x 50 nm depth

Bottom pore: 80 nm width x 80 nm depth

NANOFLUIDIC ANALYTICAL DEVICES AND METHODS OF USING THEREOF

CROSS-REFERENCE TO RELATED APPLICATIONS

This application is a national stage application filed under 35 U.S.C. § 371 of PCT/US2019/041872 filed on Jul. 15, 2019, which claims benefit of U.S. Provisional Application No. 62/697,916, filed Jul. 13, 2018, and U.S. Provisional Application No. 62/714,507, filed Aug. 3, 2018, each of which are hereby incorporated herein by reference in their entireties.

STATEMENT REGARDING FEDERALLY SPONSORED RESEARCH OR DEVELOPMENT

This invention was made with government support under EB020594 and HG006278 awarded by the National Institutes of Health and 1507577 awarded by the National Science Foundation. The government has certain rights in the invention.

BACKGROUND

Solid-state nanopores are beginning to emerge as key elements in the study of individual particles and biomolecules (e.g., nucleic acids and proteins). Using nanopores, it is possible to directly probe individual molecules with high fidelity and high throughput without requiring the necessity of a label for detection. Most solid-state nanopores are formed in a thin membrane such as $Si_3N_4$ or $SiO_2$. Many applications utilize solid-state nanopores including, for example, single molecule deoxyribonucleic acid (DNA) sequencing, protein unfolding, micro-ribonucleic acid (RNA) detection and sequencing, label-free detection of nucleotide polymorphisms, and mapping of DNA-binding proteins such as those involved in homologous recombination.

While initial proof-of-principle studies using nanopores have been encouraging, existing nanopore-based detection methodologies suffer significant drawbacks, for example the need for extensive amounts of sample preparation required before the nanopore measurement is made. Integrated devices that employ nanopore-based detectors within a network of fluidic components can provide greater control of single-molecule transport and detection, enabling new methods and systems that address current analysis needs in fields such as genomics, proteomics, and medical diagnostics.

SUMMARY

Provided herein are nanofluidic analytical devices. The nanofluidic analytical devices can be coupled to microfluidic devices to form mixed-scale analytical systems. The devices and systems can employ a sample processing region that includes a plurality of fluidically connected sample handling elements that, in combination, affect a physical/biophysical/chemical change on a sample introduced into the sample processing region. This physical/biophysical/chemical change can include, for example, purification of an analyte of interest present in the sample, concentration of an analyte of interest present in the sample, chemical modification (e.g., ligase, cleavage, polymerase, and/or chemical derivatization/hybridization) of an analyte of interest present in the sample, or a combination thereof. The analytical devices further include a nanochannel comprising a plurality of in-plane nanopores in series fluidically coupled to the sample processing region. The in-plane nanopores can be used to detect and/or analyze analyte(s) present in the sample following processing by the sample processing region. These analytical devices can advantageously provide for the label-free detection of single molecules. As such, the devices and systems can be employed in a variety of analytical applications. For example, the devices described herein can be used to sequence nucleic acids, identify proteins and polypeptides, and characterize nanoparticles (e.g., synthetic nanoparticles, viral capsids, or exosomes).

For example, provided herein are analytical devices and systems that comprise a sample processing region comprising two or more fluidically coupled sample handling elements defined by a substrate; and a nanochannel formed in the substrate and fluidically coupled to the sample processing region. The sample processing region can comprise two or more sample handling elements which together affect a physical change on a sample introduced into the sample processing region. The nanochannel can comprise an input end, an output end, a first nanopore proximate to the input end of the nanochannel, and a second nanopore spaced apart from the first nanopore and proximate to the output end of the nanochannel. Optionally, the nanochannel can further comprise one or more additional nanopores disposed along the nanochannel between the first nanopore and the second nanopore. The devices and systems can further include an electric field generator operatively positioned to create an electric field in the sample processing region and along the length of the nanochannel.

In some embodiments, the nanochannel can have a length of from 100 nm to 5 mm (e.g., from 500 nm to 500 µm). Lengthier nanochannels can be formed, for example, as meandering nanochannels. The nanochannel can have a height of from greater than 10 nm to 500 nm, a width of from greater than 10 nm and up to 500 nm, or a combination thereof.

The nanochannel comprises two or more nanopores positioned in series along the fluid flow path defined by the nanochannel. In some embodiments, the nanopores can constitute in-plane nanopores (i.e., the two or more nanopores and the nanochannel are formed within a common layer of planar substrate material). The nanopores include a constriction the nanochannel at a point along the nanochannel's fluid flow path. For example, the nanopores can each independently have a reduced height relative to the nanochannel, a reduced width relative to the nanochannel, or a combination thereof. The height and width of the nanopores are determined based on the physical and chemical properties and the signal-to-noise ratio of the sample to be interrogate with the nanopores. For example, the nanopores can each independently have a width of from 10% to 50% of the width of the nanochannel, a height of from 10% to 50% of the height of the nanochannel, or a combination thereof. For example, in some embodiments, nanopores can each independently have a width of from 1 nm to 200 nm (e.g., 1 nm to 100 nm), a height of from 1 nm to 200 nm (e.g., 1 nm to 100 nm), or a combination thereof. In certain embodiments, the cross-sectional area of the nanopores can be 30% or less than the cross-sectional area of the nanochannel, such as from 5% to 30% of the cross-sectional area of the nanochannel. In some cases, each of the nanopores can have approximately the same cross-sectional area (e.g., the same height and the same width). In other cases, the cross-sectional area of the first nanopore can be different than the cross-sectional area of the second nanopore. For example, in some embodiments, the width of the first nanopore can be different than the width of the second nanopore.

The structure of the sample processing region (e.g., the design and connectivity of sample handling elements) can vary based on the intended analytical application for the device and/or system. By way of example, in some embodiments, the device can be designed for the analysis of biomolecules (e.g., for use in DNA and RNA sequencing, for use in proteomics, etc.). In these embodiments, the sample processing region can comprise a bioreactor chamber defined by the substrate; a support structure within the bioreactor chamber and attached to the substrate; and a cleaving enzyme immobilized to the support structure. The cleaving enzyme can comprise, for example, an exonuclease, an exoribonuclease, a protease, or a combination thereof. The cleaving enzyme can be operatively positioned within the bioreactor chamber to cleave monomer or multimer units of a biopolymer operatively engaged by the cleaving enzyme.

The sample processing region can further comprise an inlet channel defined by walls of the substrate, the inlet channel having a length extending from an input end proximate to a surface of the substrate to an output end fluidically connected to the bioreactor chamber. The inlet channel can further include one or more pre-processing chambers or traps (e.g., entropic traps) used to orient or process a biopolymer prior to downstream enzymatic cleavage in the bioreactor chamber. The inlet channel can also further include a nanopore to determine the input of sample into the sampling region.

In some embodiments, the sample processing region can comprise one or more fluidically coupled sample handling elements that together purify an analyte present in the sample introduced into the sample processing region. By way of example, in one such embodiment, the sample processing region can comprise chambers that catalyze (e.g., enzymatically) the release of molecules of interest (e.g., cell free DNA in plasma) from binding proteins (e.g., histones) using a solid phase bioreactor, and then perform a solid-phase extraction of the molecules of interest (e.g., cell free DNA in plasma). The molecules of interest can then be released from the extraction surface using an appropriate release reagent before being electrophoretically driven through the nanochannel (e.g., to count and size the cell free DNA molecules).

In some embodiments, the sample processing region can comprise one or more fluidically coupled sample handling elements that together enrich the concentration of an analyte present in the sample introduced into the sample processing region. For example, the two or more fluidically coupled sample handling elements can comprise an enrichment bed fluidically coupled to a microchannel. By way of example, in one such embodiment, the sample processing region can comprise a microchannel or chamber comprising one or more micropillars. The micropillars can be coated with a molecular recognition element (e.g., an antibody, pepetide, aptamer, etc.) to enrich an analyte of interest (e.g., a particle such as an exosome). Following enrichment, the analyte can be released from the capture surface and electrophoretically driven through the nanochannel (e.g., to count the particles in a label-free manner).

The analytical devices and/or systems described herein can be fabricated using a variety of suitable substrates. For example, in some cases, the substrate can be chosen from a thermoplastic, an elastomer, a paper, a ceramic, a glass, quartz, silicon, or a combination thereof.

In certain examples, the substrate can comprise a thermoplastic. In these embodiments, the analytical device and/ or systems can be formed by a process that comprises molding or imprinting the substrate. For example, the analytical device and/or systems can be formed by nanoimprint lithography (NIL), injection molding, compression injection molding or a combination thereof.

In the realization of the analytical device and/or systems via injection molding or compression injection molding, the molds are usually fabricated via electrodeposition of metal or metal alloys from master mold.

In some embodiments, the molds can be fabricated by direct replication such as nanoimprint lithography or casting in organic-inorganic composite resists or a thin layer of organic-inorganic composite resists with a lower Young's Modulus than that of Si or metals and thus reduce the adhesion force between the molds and molded substrate. In some embodiments, the Young's modulus of the organic-inorganic composite resist can be from 500 MPa to 100 GPa. Examples of organic-inorganic composite resists include hydrogen silsesquioxane (HSQ) and polysilazane.

Also provided herein are substrate wafers (also referred to herein as chips) that comprise a plurality of the analytical devices and/or systems described herein. In some cases, the plurality of devices and/or systems fabricated in the substrate wafer can be fluidically independent. In other cases, the plurality of devices and/or systems fabricated in the substrate wafer can be fluidically connected in parallel such that the sample processing region of each of the plurality of devices and/or systems is fluidically coupled to a common wafer sample inlet and/or outlet.

DETAILED DESCRIPTION

Analytical Devices and Systems

Provided herein are nanofluidic analytical devices. The nanofluidic analytical devices can be coupled to microfluidic devices to form mixed-scale analytical systems (systems containing a network comprising both microfluidic and nanofluidic channels). The devices and systems can employ a sample processing region that includes a plurality of fluidically connected sample handling elements that, in combination, affect a physical change on a sample introduced into the sample processing region. This physical change can include, for example, purification of an analyte of interest present in the sample, concentration of an analyte of interest present in the sample, chemical modification (e.g., cleavage and/or chemical derivatization) of an analyte of interest present in the sample, or a combination thereof.

The analytical devices and systems can further include a nanochannel comprising a plurality of in-plane nanopores in series fluidically coupled to the sample processing element. The in-plane nanopores can be used to detect and/or analyze analyte(s) present in the sample following processing through the sample processing region. These devices and systems can advantageously provide for the label-free detection of single molecules.

Figure 1A:
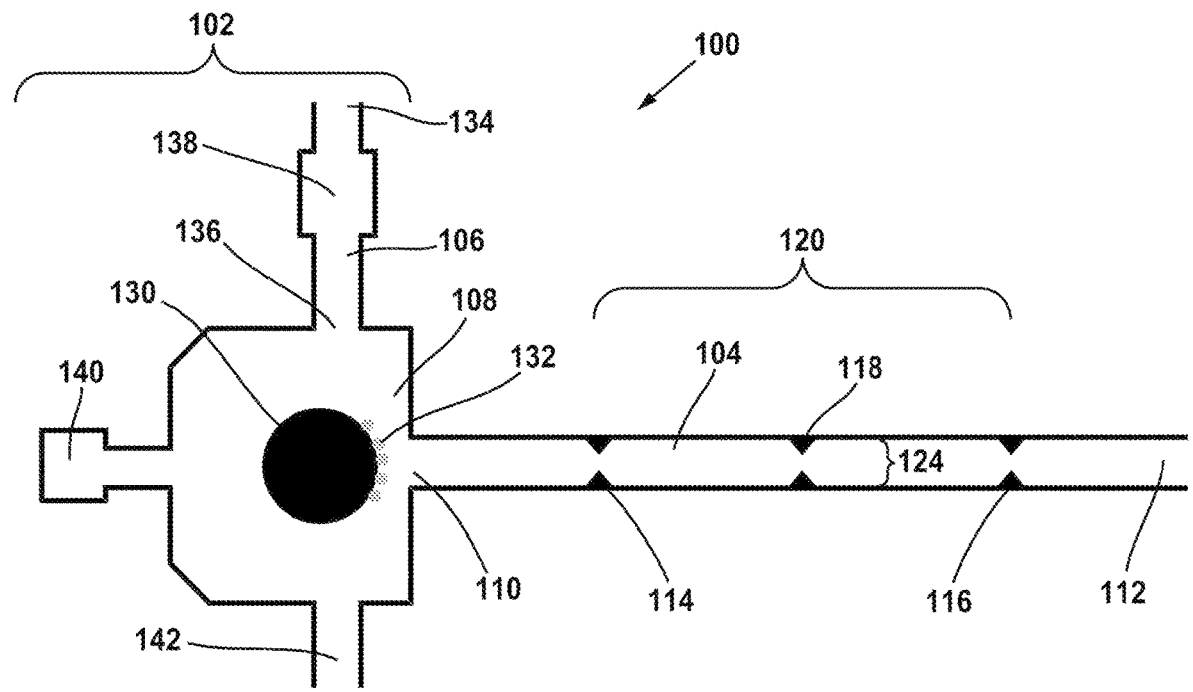
FIG. 1A is a schematic illustration of an example nanofluidic device described herein.

Referring now to FIG. 1A, provided herein are analytical devices (100) that comprise a sample processing region (102) comprising two or more fluidically coupled sample handling elements defined by a substrate; and a nanochannel (104) formed in the substrate and fluidically coupled to the sample processing region. The sample processing region (102) can comprise two or more sample handling elements (e.g., a first sample handling element 106 (in this example an inlet channel); and a second sample handling element 108 (in this example a bioreactor chamber) which act in concert to affect a physical change on a sample introduced into the sample processing region. The nanochannel (104) can comprise an input end (110), an output end (112), a first nanopore (114) proximate to the input end of the nanochannel, and a second nanopore (116) spaced apart from the first nanopore and proximate to the output end of the nanochannel. Optionally, the nanochannel can further comprise one or more additional nanopores (118) disposed along the nanochannel between the first nanopore and the second nanopore.

The nanochannel (can be linear in shape, or it can possess one or more non-linear regions (e.g., a curved region, a spiral region, an angular region, or combinations thereof) along the length of the fluid flow path. In certain examples, the nanochannel can be a straight, curved, or meandered. Referring still to FIG. 1A, in some embodiments, the length of the nanochannel (120), measured as the linear distance along the fluid flow path between the first nanopore (114) and the second nanopore (116) can be at least 100 nm (e.g., at least 500 nm, at least 1 µm, at least 5 µm, at least 10 µm, at least 25 µm, at least 50 µm, at least 100 µm, at least 200 µm, at least 250 µm, at least 300 µm, at least 400 µm, at least 500 µm, at least 1 mm, at least 2 mm, at least 3 mm, at least 4 mm, at least 5 mm, or longer). In some embodiments, the length of the nanochannel (120) can be 5 mm or less (e.g., 4 mm, 3 mm, 2 mm, 1 mm, 500 µm, 400 µm or less, 300 µm or less, 250 µm or less, 200 µm or less, 100 µm or less, 50 µm or less, 25 µm or less, 10 µm or less, 5 µm or less, 1 µm or less, or 500 nm or less). Nanochannel (104) can have a length (120) ranging from any of the minimum values described above to any of the maximum values described above. For example, in some embodiments, nanochannel (104) can have a length (120) of from 100 nm to 5 mm (e.g., from 500 nm to 500 µm, from 500 nm to 100 µm, or from 5 µm to 100 µm).

Figure 1B:
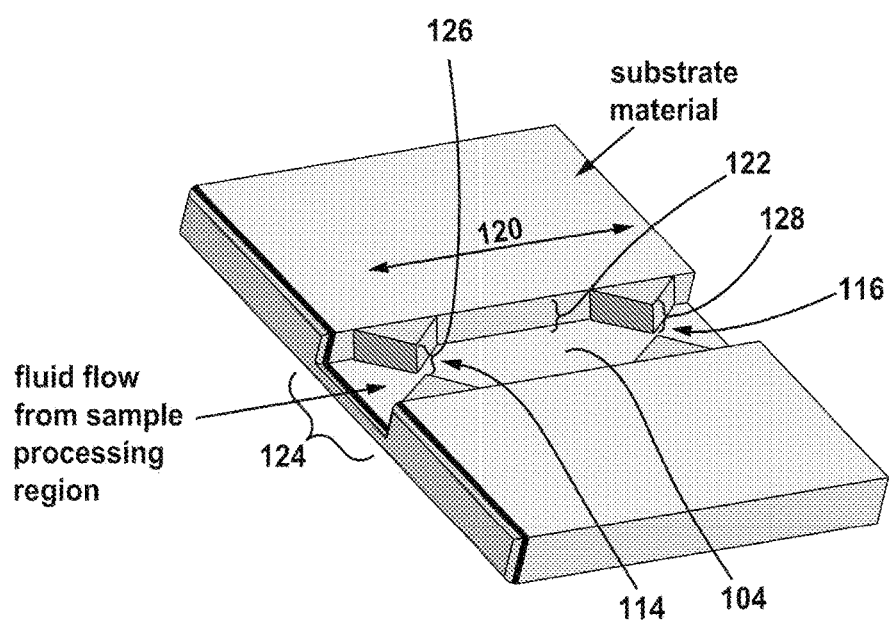
FIG. 1B is a perspective view of a nanochannel of an example nanofluidic device described herein. The upstream sample processing region is omitted for clarity.

Referring now to FIG. 1B, in some embodiments, the nanochannel (104) can have a height (122) of greater than 10 nm (e.g., at least 25 nm, at least 50 nm, at least 75 nm, at least 100 nm, at least 125 nm, at least 150 nm, at least 175 nm, at least 200 nm, at least 225 nm, at least 250 nm, at least 275 nm, at least 300 nm, at least 325 nm, at least 350 nm, at least 375 nm, at least 400 nm, at least 425 nm, at least 450 nm, or at least 475 nm). In some embodiments, the nanochannel (104) can have a height (122) of 500 nm or less (e.g., 475 nm or less, 450 nm or less, 425 nm or less, 400 nm or less, 375 nm or less, 350 nm or less, 325 nm or less, 300 nm or less, 275 nm or less, 250 nm or less, 225 nm or less, 200 nm or less, 175 nm or less, 150 nm or less, 125 nm or less, 100 nm or less, 75 nm or less, 50 nm or less, or 25 nm or less).

Nanochannel (104) can have a height (122) ranging from any of the minimum values described above to any of the maximum values described above. For example, in some embodiments, nanochannel (104) can have a height (122) of from 10 nm to 500 nm (e.g., from 25 nm to 500 nm, from 50 nm to 500 nm, from 75 nm to 150 nm).

In some embodiments, the nanochannel (104) can have a width (124) of greater than 10 nm (e.g., at least 25 nm, at least 50 nm, at least 75 nm, at least 100 nm, at least 125 nm, at least 150 nm, at least 175 nm, at least 200 nm, at least 225 nm, at least 250 nm, at least 275 nm, at least 300 nm, at least 325 nm, at least 350 nm, at least 375 nm, at least 400 nm, at least 425 nm, at least 450 nm, or at least 475 nm). In some embodiments, the nanochannel (104) can have a width (124) of 500 nm or less (e.g., 475 nm or less, 450 nm or less, 425 nm or less, 400 nm or less, 375 nm or less, 350 nm or less, 325 nm or less, 300 nm or less, 275 nm or less, 250 nm or less, 225 nm or less, 200 nm or less, 175 nm or less, 150 nm or less, 125 nm or less, 100 nm or less, 75 nm or less, 50 nm or less, or 25 nm or less).

Nanochannel (104) can have a width (124) ranging from any of the minimum values described above to any of the maximum values described above. For example, in some embodiments, nanochannel (104) can have a width (124) of from 10 nm to 500 nm (e.g., from 25 nm to 500 nm, from 50 nm to 500 nm, from 75 nm to 150 nm).

Molecular specific interactions between an analyte and the wall or walls of the nanochannel can be controlled by the composition and functionalization of the nanochannel walls. In one embodiment, the walls of the nanochannel comprise the same composition as the substrate, with or without modification. Alternatively, the wall or walls of the nanochannel may comprise a different composition than the substrate, with or without modification.

In some embodiments, the wall or walls of the nanochannel can comprise a polymeric material (e.g., PMMA, PC, epoxy-based resins, copolymers, polysulfones, elastomers, and polymeric organosilicons, or any combination of these materials). The polymeric material may be in its native state, or, alternatively, surface modified. For example, a polymeric nanochannel wall can comprise a neutral, hydrophobic, hydrocarbon surface with different degrees of chain order. In another example, the nanochannel wall surface may comprise a charge neutral, hydrophilic surface. In yet another example, the nanochannel wall surface may comprise a charged, hydrophilic surface.

A nanochannel wall surface comprising a neutral, hydrophobic, hydrocarbon surface with different degrees of chain order can be formed from monolayers of methyl-terminated alkane chains having various lengths that are built on the polymer nanochannel surfaces (Henry et al., "Surface Modification of Poly(methyl methacrylate) Used in the Fabrication of Microanalytical Devices," *Anal. Chem.* 72:5331-5337(2000), which is hereby incorporated by reference in its entirety). The monolayers can be formed by attachment of amino-alkanes to carboxylic acid-terminated surfaces (McCarley et al., "Resist-Free Patterning of Surface Architectures in Polymer-Based Microanalytical Devices," *J. Am. Chem. Soc.* 127:842-843 (2005); Wei et al., "Photochemically Patterned Poly(methyl methacrylate) Surfaces Used in the Fabrication of Microanalytical Devices. *J. Phys. Chem. B* 109:16988-16996 (2005), which are hereby incorporated by reference in their entirety). Alternatively, the monolayers can be formed from urea-linked alkane layers on amine functionalities attached to the polymer via amide bonds (Henry, A. C., "Surface Modification and Characterization of PMMA Used in the Construction of Microelectromechanical Systems," In *Chemistry*, pp. 147, Louisiana State University, Baton Rouge (2001); Henry et al., "Surface Modification of Poly(methyl methacrylate) Used in the Fabrication of Microanalytical Devices," *Anal. Chem.* 72:5331-5337 (2000), which are hereby incorporated by reference in their entirety). For example, well-ordered octadecyl monolayers can be formed on PMMA surfaces by reaction of n-octadecylisocyanate with amine-terminated PMMA surfaces (Henry & McCarley, "Selective Deposition of Metals on Plastics Used in the Construction of Microanalytical Devices: Photo-Directed Formation of Metal Features on PMMA," *J. Phys. Chem. B* 105:8755-8761 (2001), which is hereby incorporated by reference in its entirety), and these C18-PMMA surfaces are excellent for chromatographic separations in embossed channels (Galloway et al., "Contact Conductivity Detection in Poly(methyl methacylate)-Based Microfluidic Devices for Analysis of Mono- and Polyanionic Molecules," *Anal. Chem.* 74:2407-2415 (2002), which is hereby incorporated by reference in its entirety). Thus, various chain length n-alkylisocyanates can be used to make hydrophobic polymer surfaces possessing different degrees of order, which will affect the flight-time of the monomers, such as dNMPs. Issues regarding non-zero electroosmotic flows (EOFs) can be addressed by capping unreacted foundation groups (Henry, A. C., "Surface Modification and Characterization of PMMA Used in the Construction of Microelectromechanical Systems," In *Chemistry*. Louisiana State University, Baton Rouge (2001); Wei et al., "Photochemically Patterned Poly(methyl methacrylate) Surfaces Used in the Fabrication of Microanalytical Devices. J. Phys. Chem. B 109:16988-16996 (2005), which are hereby incorporated by reference in their entirety).

The latter two objectives are accomplished by attaching materials possessing (a) glycol and (b) organic acid or amine termini to carboxyl- or amine-terminated polymer surfaces. One approach for creating hydrophilic, charge neutral surfaces, involves reacting properly activated carboxylic-acid terminated polymer surfaces with ethanolamine or aminotri(ethyleneglycol) (Wei, S., "Multianalyte Detection of Breast Cancer by Fabrication of Hybridmicroarrays on Polymer-based Microanalytical Devices," In *Chemistry*. Louisiana State University, Baton Rouge (2005), which is hereby incorporated by reference in its entirety). As an alternative, amine-terminated PMMA and PC surfaces can be modified with glycols having surface generated carboxylic groups, such as glycolic acid or carboxyl-tri(ethyleneglycol). Cationic surfaces (at the pH conditions used for the exonucleases) can be formed using well-established methods for production of amine-terminated polymers (Henry & McCarley, "Selective Deposition of Metals on Plastics Used in the Construction of Microanalytical Devices: Photo-Directed Formation of Metal Features on PMMA," *J. Phys. Chem. B* 105:8755-8761 (2001); Henry et al., "Surface Modification of Poly(methyl methacrylate) Used in the Fabrication of Microanalytical Devices," *Anal. Chem.* 72:5331-5337 (2000); McCarley et al., "Resist-Free Patterning of Surface Architectures in Polymer-Based Microanalytical Devices," *J. Am. Chem. Soc.* 127:842-843 (2005); Wei et al., "Photochemically Patterned Poly(methyl methacrylate) Surfaces Used in the Fabrication of Microanalytical Devices. *J. Phys. Chem. B* 109:16988-16996 (2005), which are hereby incorporated by reference in their entirety). Anionic surfaces will result from routes that lead to either carboxylic-acid terminated surfaces (McCarley et al., "Resist-Free Patterning of Surface Architectures in Polymer-Based Microanalytical Devices," *J. Am. Chem. Soc.* 127:842-843 (2005); Vaidya et al., "Surface Modification and Characterization of Microfabricated Poly(carbonate) Devices: Manipulation of Electroosmotic Flow," *Analyst* 127:1289-1292 (2002), which are hereby incorporated by reference in their entirety) or those bearing sulfonic acids, with the latter having an almost pH-independent surface charge (Henry, A. C., "Surface Modification and Characterization of PMMA Used in the Construction of Microelectromechanical Systems," In *Chemistry*, pp. 147, Louisiana State University, Baton Rouge (2001), which is hereby incorporated by reference in its entirety).

Most modification chemistries are based on creating a scaffold, for example carboxy groups, comprised of functional groups that can be regiospecifically patterned in that only certain locations are activated on the substrate by masking areas that are not intended to be activated and UV exposing this assembly (McCarley et al., "Resist-Free Patterning of Surface Architectures in Polymer-Based Microanalytical Devices," *J. Am. Chem. Soc.* 127:842-843 (2005); Wei et al., "Photochemically Patterned Poly(methyl methacrylate) Surfaces Used in the Fabrication of Microanalytical Devices. *J. Phys. Chem. B* 109:16988-16996 (2005), which are hereby incorporated by reference in their entirety). Monolayer elements can be selectively immobilized to only the nanochannel domains through masking, leaving the rest of the solid support substrate and structures therein in their native form. Even though the nanochannel dimensions are below the diffraction limit of the activating light (254 nm), the length of the channel is well above the diffraction limit and this is the critical dimension The nanopores (114, 116) can each independently have a reduced height relative to the nanochannel, a reduced width relative to the nanochannel, or a combination thereof. The height and width of the nanopores can be selected based on the physical and chemical properties and signal-to-noise ratio of the sample to interrogate with the nanopores.

In some embodiments, the nanopores (114, 116) can each independently have a height (128) that is at least 10% (e.g., at least 15%, at least 20%, at least 25%, at least 30%, at least 35%, at least 40%, or at least 45%) of the height of the nanochannel (122). In some embodiments, the nanopores (114, 116) can each independently have a height (128) that is 50% or less (e.g., 45% or less, 40% or less, 35% or less, 30% or less, 25% or less, 20% or less, or 15% or less) of the height of the nanochannel (122).

The height of each nanopore (128) can independently range from any of the minimum values described above to any of the maximum values described above. For example, in some embodiments, each nanopore (114, 116) can independently have a height (128) that is from 10% to 50% of the height of the nanochannel (122)

In some embodiments, the nanopores (114, 116) can each independently have a height (128) of at least 1 nm (e.g., at least 5 nm, at least 10 nm, at least 15 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, or at least 95 nm). In some embodiments, the nanopores (114, 116) can each independently have a height (128) of 100 nm or less (e.g., 95 nm or less, 90 nm or less, 85 nm or less, 80 nm or less, 75 nm or less, 70 nm or less, 65 nm or less, 60 nm or less, 55 nm or less, 50 nm or less, 45 nm or less, 40 nm or less, 35 nm or less, 30 nm or less, 25 nm or less, 20 nm or less, 15 nm or less, 10 nm or less, or 5 nm or less).

The nanopores (114, 116) can each independently have a height (128) ranging from any of the minimum values described above to any of the maximum values described above. For example, in some embodiments, the nanopores (114, 116) can each independently have a height (128) of from 1 nm to 100 nm (e.g., from 30 nm to 100 nm).

In some embodiments, the nanopores (114, 116) can each independently have a width (126) that is at least 10% (e.g., at least 15%, at least 20%, at least 25%, at least 30%, at least 35%, at least 40%, or at least 45%) of the width of the nanochannel (124). In some embodiments, the nanopores (114, 116) can each independently have a width (126) that is 50% or less (e.g., 45% or less, 40% or less, 35% or less, 30% or less, 25% or less, 20% or less, or 15% or less) of the width of the nanochannel (124).

The width of each nanopore (126) can independently range from any of the minimum values described above to any of the maximum values described above. For example, in some embodiments, each nanopore (114, 116) can independently have a width (126) that is from 10% to 50% of the width of the nanochannel (124)

In some embodiments, the nanopores (114, 116) can each independently have a width (126) of at least 1 nm (e.g., at least 5 nm, at least 10 nm, at least 15 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, or at least 95 nm). In some embodiments, the nanopores (114, 116) can each independently have a width (126) of 100 nm or less (e.g., 95 nm or less, 90 nm or less, 85 nm or less, 80 nm or less, 75 nm or less, 70 nm or less, 65 nm or less, 60 nm or less, 55 nm or less, 50 nm or less, 45 nm or less, 40 nm or less, 35 nm or less, 30 nm or less, 25 nm or less, 20 nm or less, 15 nm or less, 10 nm or less, or 5 nm or less).

The nanopores (114, 116) can each independently have a width (126) ranging from any of the minimum values described above to any of the maximum values described above. For example, in some embodiments, the nanopores (114, 116) can each independently have a width (126) of from 1 nm to 100 nm (e.g., from 30 nm to 100 nm).

In certain embodiments, the cross-sectional area of each of the nanopores (height of the nanopore×width of the nanopore) can independently can be 30% or less (e.g., 25% or less, 20% or less, 15% or less, or 10% or less) of the cross-sectional area of the nanochannel (height of the nanochannel×width of the nanochannel). For example, the cross-sectional area of each of the nanopores can independently can be from 5% to 30% of the cross-sectional area of the nanochannel.

In some cases, each of the nanopores can have approximately the same cross-sectional area (e.g., the same height and the same width, ±10%, or ±5%). In other cases, the cross-sectional area of the first nanopore can be different than the cross-sectional area of the second nanopore. For example, in some embodiments, the width of the first nanopore can be different than the width of the second nanopore.

In some embodiments, the nanopores (114, 116) can each independently have a length (measured along the path for fluid flow through the nanopore) of at least 1 nm (e.g., at least 5 nm, at least 10 nm, at least 15 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, or at least 95 nm). In some embodiments, the nanopores (114, 116) can each independently have a length of 100 nm or less (e.g., 95 nm or less, 90 nm or less, 85 nm or less, 80 nm or less, 75 nm or less, 70 nm or less, 65 nm or less, 60 nm or less, 55 nm or less, 50 nm or less, 45 nm or less, 40 nm or less, 35 nm or less, 30 nm or less, 25 nm or less, 20 nm or less, 15 nm or less, 10 nm or less, or 5 nm or less).

The nanopores (114, 116) can each independently have a length ranging from any of the minimum values described above to any of the maximum values described above. For example, in some embodiments, the length can each independently have a width (126) of from 1 nm to 100 nm (e.g., from 10 nm to 100 nm, or from 30 nm to 100 nm).

The structure of the sample processing region (e.g., the design and connectivity of sample handling elements) can vary based on the intended analytical application for the device. The plurality of fluidically connected sample handling elements can be selected so that, in combination, they affect a desired physical change on a sample introduced into the sample processing region. This physical change can include, for example, purification of an analyte of interest present in the sample, concentration of an analyte of interest present in the sample, chemical modification (e.g., cleavage and/or chemical derivatization) of an analyte of interest present in the sample, or a combination thereof. For example, the sample processing region can be structured to isolate circulating tumor cells (CTCs), cell free DNA (cfDNA) or both directly from whole blood; perform a solid-phase extraction and/or enrichment of DNA (genomic or cfDNA or both) and/or RNA; fragment DNA to ~40 kbp lengths; feed the DNA fragments into the bioreactor chamber for sequence analysis; enzymatically digest a biopolymer, or a combination thereof.

The sample processing region can include, for example and without limitation, sample handling elements for solid-phase extraction of nucleic acids from cell lysates, both DNA and RNA (Witek et al., "96-Well Polycarbonate-Based Microfluidic Titer Plate for High-Throughput Purification of DNA and RNA," *Analytical Chemistry* 80:3483-3491 (2008); Park et al., "A Titer Plate-Based Polymer Microfluidic Platform for High Throughput Nucleic Acid Purification," *Biomedical Microdevices* 10:21-33 (2008), which are hereby incorporated by reference in their entirety); sample handling elements for protein/polypeptide isolation and enrichment; sample handling elements for shearing nucleic acids to the appropriate size for subsequent analysis/sequencing; sample handling elements for thermal amplification (Hashimoto et al., "Rapid PCR in a Continuous Flow Device," *Lab On A Chip* 4:638-645 (2004); Hashimoto et al., "Ligase Detection Reaction/Hybridization Assays Using Three-Dimensional Microfluidic Networks for the Detection of Low-Abundant DNA Point Mutations," *Analytical Chemistry* 77:3243-3255 (2005), which are hereby incorporated by reference in their entirety); sample handling elements for rare cell selection (Adams et al., "Highly Efficient Circulating Tumor Cell Isolation From Whole Blood and Label-Free Enumeration Using Polymer-Based Microfluidics With an Integrated Conductivity Sensor," *J. Am. Chem. Soc.* 130: 8633-8641 (2008); Dharmasiri et al., "Capture and Enumeration of LNCaP Prostate Cancer Cells Using Aptamers Immobilized to a PMMA Microsampling Unit," *Electrophoresis* 30:3289-3300 (2009), which are hereby incorporated by reference in their entirety); and DNA arrays (Xu et al., "Polymer Microfluidic Chips with Integrated Waveguides for Reading Microarrays," *Analytical Chemistry* 79:9007-9013 (2007), which is hereby incorporated by reference in its entirety).

By way of example, in some embodiments, the device can be designed for the analysis of biomolecules (e.g., for use in DNA and RNA sequencing, for use in proteomics, etc.). Referring again to FIG. 1A, in these embodiments, the sample processing region (102) can comprise a bioreactor chamber (108) defined by the substrate; a support structure (130) within the bioreactor chamber and attached to the substrate; and a cleaving enzyme (132) immobilized to the support structure. The cleaving enzyme can be operatively positioned within the bioreactor chamber to cleave monomer or multimer units of a biopolymer operatively engaged by the cleaving enzyme.

The bioreactor chamber (108) can be from about 100 to about 1000 nm wide. The support structure (130) can be, for example, a pillar having one or more cleaving enzymes (e.g., an exonuclease, exoribonuclease, or protease) covalently attached thereto. The support structure of the bioreactor chamber may comprise the same or different material as the solid substrate. In one embodiment, the support structure is a polymer support structure (e.g., PMMA, PC, or COC polymer). The support structure of the bioreactor chamber can be about 50 nm to about 900 nm in width and about 10 nm to about 100 nm tall. The surface area of the support structure can be about 1500 to about 285,000 nm$^2$. The cleaving enzyme immobilized on the support structure engages and cleaves a biopolymer molecule that enters the bioreactor chamber from the inlet channel. In some embodiments, the cleaving enzyme may require activation. Buffers containing activating agents, e.g., Mg$^{+2}$, or electrophoresis buffers can be stored in a reagent chamber (140) fluidically coupled to the bioreactor chamber.

The cleaving enzyme may be tethered to the support structure of the bioreactor chamber using standard coupling chemistry known in the art. In one embodiment, the enzyme is tethered to the support structure via adventitious immobilization. Commercially-available cleavage enzymes such as exonucleases (New England Biolabs) or other enzymes can be immobilized using well-established carbodiimide (1-ethyl-3-(3-dimethylaminopropyl)carbodiimide, EDC) chemistries routinely utilized for a variety of antibodies (McCarley et al., "Resist-Free Patterning of Surface Architectures in Polymer-Based Microanalytical Devices," *J. Am. Chem. Soc.* 127:842-843 (2005); Chen et al., "Functional Template-Derived Poly(methyl methacrylate) Nanopillars for Solid-Phase Biological Reactions," *Chem. Mater.* 19:3855-3857 (2007); and Wang et al., "Microarrays Assembled in Microfluidic Chips Fabricated From Poly (methyl methacrylate) for the Detection of Low-Abundant DNA Mutations," *Anal. Chem.* 75:1130-1140 (2003), which are hereby incorporated by reference in their entirety).

In another embodiment, the cleaving enzyme is tethered to the support structure via the immobilization of a suitable capture moiety, where the enzyme contains or is engineered to contain a capture moiety binding partner. For example, in one embodiment, the surface of the support structure contains a plurality of capture ligands bound to Ni(II) that allow for enzyme immobilization using a hexahistidine tag engineered enzyme (Dapprich, J., "Single-Molecule DNA Digestion by Lambda-Exonuclease," *Cytometry* 36:163-168 (1999), which is hereby incorporated by reference in its entirety). The Ni(II) surfaces can be generated by coordinating Ni(II) to CT-PMMA that has been modified with 1-acetato-4-benzyl-triazacyclononane (Acbztacn) (Johnson & Martin, "Controlling Protein Orientation at Interfaces Using Histidine Tags: An Alternative to Ni/NTA," *J. Am. Chem. Soc.* 127:2018-2019 (2005); Warden et al., "Synthesis of Novel Derivatives of 1,4,7-Triazacyclononane," *Organic Lett.* 3:2855-2858 (2001), which are hereby incorporated by reference in their entirety) or nitrilotriacetic acid (NTA). Acbztacn-PMMA surfaces can be formed by exposure of CT-PMMA surfaces to EDC/Acbztacn to form amide linkages of the Acbztacn to the PMMA through the secondary amine of the triazacyclononane (Johnson & Martin, "Controlling Protein Orientation at Interfaces Using Histidine Tags: An Alternative to Ni/NTA," *J. Am. Chem. Soc.* 127:2018-2019 (2005), which is hereby incorporated by reference in its entirety).

Alternative capture and binding partners that can be used to tether the cleaving enzyme or enzymes to the support structure include, without limitation, biotin and streptavidin, maltose and maltose binding protein, chitin and chitin binding protein, amylase and MBP, glutathione transferase and glutathione-S-transferase, integrin and integrin binding peptides, nucleic acid oligonucleotides or nucleic acid analogue oligonucleotides and their complementary oligonucleotides.

In another embodiment, the enzyme is tethered to the support structure using immobilized antibodies. For example, the cleaving enzyme, which has been engineered to contain a hexahistidine tag, can be immobilized to the support structure via anti-His-Tag antibodies (Perkins et al., "Sequence-Dependent Pausing of Single Lambda Exonuclease Molecules," *Science* 301:1914-1918 (2003), which is hereby incorporated by reference in its entirety). Immobilization of commercially-available anti-histidine-Tag antibodies (Roche, Qiagen, or Novagen) or other antibodies can be achieved using well-established carbodiimide (1-ethyl-3-(3-dimethylaminopropyl)carbodiimide, EDC) chemistries routinely utilized for a variety of antibodies (McCarley et al., "Resist-Free Patterning of Surface Architectures in Polymer-Based Microanalytical Devices," *J. Am. Chem. Soc.* 127: 842-843 (2005); Chen et al., "Functional Template-Derived Poly(methyl methacrylate) Nanopillars for Solid-Phase Biological Reactions," *Chem. Mater.* 19:3855-3857 (2007); and Wang et al., "Microarrays Assembled in Microfluidic Chips Fabricated From Poly(methyl methacrylate) for the Detection of Low-Abundant DNA Mutations," *Anal. Chem.* 75:1130-1140 (2003), which are hereby incorporated by reference in their entirety). Additional embodiments of antibody capture of enzyme containing an engineered peptide capture sequence include but are not limited to: FLAG epitope with Anti-FLAG antibody; and Myc tag epitope with Anti-Myc Tag antibody.

Surface coverage of the support structure by the cleaving enzyme can be assessed by evaluation of protein content in immobilization solutions before and after immobilization (solution difference method) (Smith et al., "Measurement of Protein Using Bicinchoninic Acid," *Anal. Biochem.* 150:76-85 (1985); Stoscheck, C. M., "Quantitation of Protein," *Methods in Enzymol.* 182:50-68 (1990), which are hereby incorporated by reference in their entirety), and its activity will be determined using standard kinetic methods (Chen et al., "Functional Template-Derived Poly(methyl methacrylate) Nanopillars for Solid-Phase Biological Reactions," *Chem. Mater.* 19:3855-3857 (2007), which is hereby incorporated by reference in its entirety).

In one embodiment, the immobilized cleaving enzyme of the bioreactor chamber is an exonuclease. As used herein an "exonuclease" encompasses any enzyme capable of catalyzing the hydrolysis of a single nucleotide from the end of a DNA or RNA molecule. In one embodiment, the exonuclease is a processive enzyme, i.e., it catalyzes a series of successive cleavage events of a template without releasing the template. Such exonucleases can be monomeric enzymes, multimeric enzymes, or enzyme complexes comprised of multiple subunits. Suitable exonucleases include, without limitation, lambda exonuclease, which cleaves double-stranded and single-stranded DNA substrates in the 5'-3' direction; exonuclease I, which cleaves single-stranded DNA substrates in the 3'-5' direction; exonuclease III, which cleaves double-stranded DNA substrates in the 3'-5' direction; T7 exonuclease, which cleaves double-stranded DNA substrates, or RNA/DNA hybrid substrates in the 5'-3' direction; XRN-1, which cleaves single-stranded RNA substrates in the 5'-3' direction (Geisler and Coller, "XRN1: A Major 5' to 3' Exoribonuclease in Eukaryotic Cells," *Enzymes* 31:97-110 (2012), Jinek et al., "Coupled 5' Nucleotide Recognition and Processivity in Xrn1-Mediated mRNA Decay," *Mol. Cell* 41:600-608 (2011), and Jones et al., "The 5'→3' Exoribonuclease XRN1/Pacman and its Functions in Cellular Processes and Development," *WIREs RNA* 3:455-468 (2012), which are hereby incorporated by reference in their entirety); RNase II, which cleaves single-stranded RNA substrates in the 3'-5' direction (Zuo et al., "Structural Basis for Processivity and Single-Strand Specificity of RNaseII,"*Mol. Cell* 24:149-156 (2006), which is hereby incorporated by reference in its entirety); and exosome complex, which cleaves single-stranded RNA substrates in the 3'-5' direction (Lee et al., "Elastic Coupling Between RNA Degradation and Unwinding by an Exoribonuclease, *Science* 336:1726-1729 (2012), which is hereby incorporated by reference in its entirety). The support structure of the bioreactor chamber may comprise any one or more of the aforementioned exonuclease enzymes. In some embodiments, a combination of enzymes, such as, e.g., an exosome complex in combination with XRN-1, ensures cleavage of an RNA molecule regardless of RNA orientation (i.e., 5'-3' or 3'-5') as it enters the bioreactor chamber. In some embodiments, a prior processing step may be needed, for example decapping messenger RNA to create a 5' phosphorylated substrate for XRN-1, or deadenylation of messenger RNA to create a suitable substrate for the Exosome complex. Such additional enzymes may be present in pre-reaction chambers, the feeder channel, or attached to the support structure of the bioreactor chamber.

In another embodiment, the immobilized cleaving enzyme of the bioreactor chamber is a protease or peptidase. As used herein, "protease" and "peptidase" are used interchangeably to refer to any enzyme capable of proteolysis by hydrolysis of peptide bonds. Suitable proteases include, without limitation, serine proteases, threonine proteases, cysteine proteases, aspartate proteases (cleave at the amino side of aspartate residues), asparagine proteases, lysine proteases (cleaves at the carboxyl side of lysine residues), metalloproteases, and glutamic acid proteases (cleaves at the carboxyl side of glutamate or aspartate). Particular proteases that are suitable for use in the present invention include, without limitation, proteinase K, which cleaves at the carboxyl side of aliphatic, aromatic, and hydrophobic residues; *S. aureus* V-8 Protease which cleaves at the carboxyl side of aspartate and glutamate residues; trypsin, which cleaves at the carboxyl side of arginine and lysine residues; and chymotrypsin, which cleaves at the carboxyl side of tyrosine, phenylalanine, tryptophan and leucine.

The bioreactor chamber (108) can be fluidically coupled to an output channel (142) that runs opposite the inlet channel. The output channel can collect non-cleaved biopolymer components, e.g., when the biopolymer molecule is a double stranded DNA molecule and only one strand of the DNA is cleaved by the cleaving enzyme, the output channel collects the non-digested strand of DNA. Alternatively, the output channel can serve as a second feeder channel, collecting non-digested biopolymer units and transporting them downstream to one or more other bioreactor chambers for cleavage.

The sample processing region can further comprise an inlet channel (106) defined by walls of the substrate, the inlet channel having a length extending from an input end (134) proximate to a surface of the substrate to an output end (136) fluidically connected to the bioreactor chamber (108). The inlet channel can be sized to receive and orientate a biopolymer molecule, e.g., a nucleic acid molecule, prior to feeding it into the bioreactor chamber for enzymatic processing.

The input end (134) may be modified structurally in various ways to facilitate capture and loading of a biopolymer molecule into the inlet channel. For example, the input end may be a simple micro/sub-micron groove inlet, a V-shape micro/sub-micron groove inlet, a pillar inlet with an array of micro/nanopillars, or a funnel inlet.

In one embodiment, the dimensions of the inlet channel (106) are less than or equal to 100 nm wide and less than or equal to 100 nm deep. In another embodiment, the dimensions of the inlet channel (106) are less than or equal to 75 nm wide and less than or equal to 75 nm deep. In another embodiment, the dimensions of the inlet channel (106) are less than or equal to 50 nm wide and less than or equal to 50 nm deep. The length of the inlet channel (106) can be from about 1 µm to about 100 µm or longer, although longer and shorter inlet channel lengths can also be used. The inlet channel can have any desired geometrical cross-section, i.e., circle, triangle, square, rectangle, pentagon, hexagon, heptagon, or octagon.

The inlet channel can further include one or more preprocessing chambers or traps (e.g., entropic traps, 138) to orient or process a biopolymer prior to downstream enzymatic cleavage in the bioreactor chamber. Suitable entropic nucleic acid traps are known in the art, see e.g., Han and Craighead, "Separation of Long DNA Molecules in Microfabricated Entropic Trap Array," *Science* 288: 1026-1029 (2000), O'Donnell et al., "Pressure-driven DNA Transport Across an Artificial Nanotopography," *New Journal of Physics* 11: 075032 (2009), and Reisner et al., "Direct Self-Organization of Single DNA Molecules in a Nanoslit via Embedded Nanopt Arrays," *Proc. Natl. Acad. Sci. USA* 106: 79-84 (2009), which are hereby incorporated by reference in their entirety.

The inlet channel can further contain one or more preprocessing chambers used to process a biopolymer molecule prior to downstream enzymatic cleavage in the bioreactor chamber. For example, if the biopolymer is an mRNA molecule, the molecule may need to be decapped or deadenylated to create a suitable substrate for enzymatic cleavage. Suitable processing enzymes can be tethered or coupled to the walls of the inlet channel or walls of a pre-bioreactor processing chamber located in the inlet channel upstream of the bioreactor chamber.

The entropic trap, inlet channel, and any other prebioreactor processing chamber can also contain immobilized capture oligonucleotides. These capture oligonucleotides immobilized to the walls or support structures within the channel, traps, or chambers may comprise a homopolymer repeat sequence that is complementary to an end of the biopolymer molecule, e.g., a nucleic acid, that is fed through the channel. Hybridization between the immobilized capture oligonucleotides and complementary regions of the biopolymer molecule help orient the molecule as it traverses the feeder channel.

Figure 3:
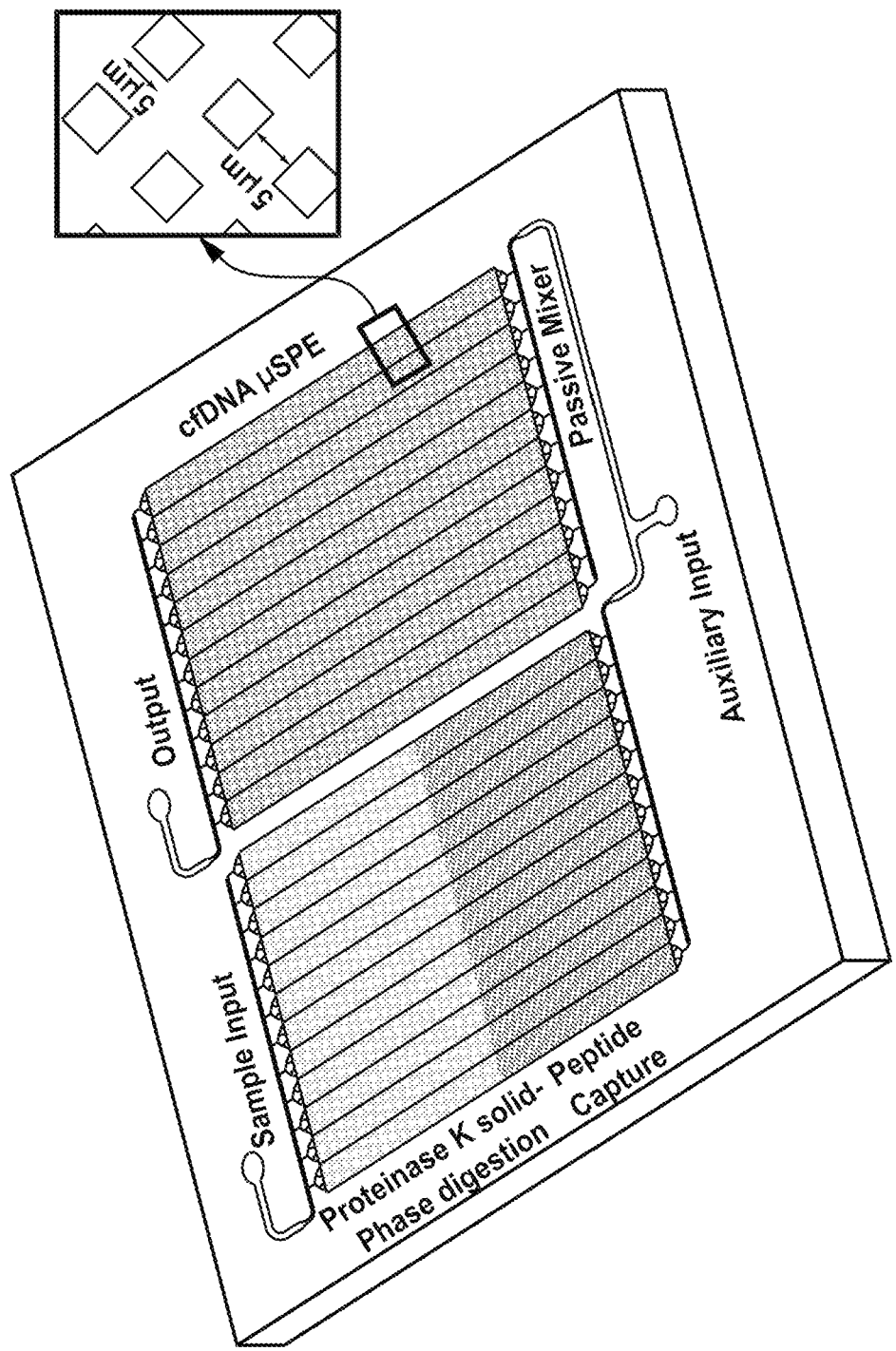
FIG. 3 is a schematic illustration of an example sample processing element that can extract an analyte of interest from a sample. This example sample processing device can be, for example, used to extract cell free DNA from plasma. During operation, plasma flows through region 1, where proteinase K is immobilized to release the cell free DNA from histones, and digest endogenous proteins found in plasma. Next, fluid is transported to region 2 where peptides are cleared using electrostatic interactions. An immobilization buffer is introduced through the auxiliary port, where the buffer mixes with the sample in a passive mixing channel. Finally, fluid passes into region 3 where the cell free DNA is extracted. The dimensions of the pillars within region 3 can be can be selected to maximize recovery of the cell free DNA molecules. The output of the sample processing device can be connected to a nanochannel detector through the output port.

In some embodiments, the sample processing region can comprise one or more fluidically coupled sample handling elements that together purify an analyte present in the sample introduced into the sample processing region. FIG. 3 is a schematic illustration of an example sample processing element that can extract and purify an analyte of interest from a sample. This example sample processing device can be, for example, used to extract cell free DNA from plasma.

The sample processing region in this case includes microfluidic channels populated with diamond-shape pillars that have a side length of 5 µm with a 5 µm spacing, and a 20 µm height. Small inter-pillar spacing minimizes diffusional distances required to illicit binding between cfDNA molecules and the polymer surface, leading to efficient recovery. The large surface area (75 cm$^2$) of the extraction bed ensures cfDNA high mass load in a small (18 µL) volume appropriate for detection.

The example sample processing element includes three major sections used for: (1) the solid-phase digestion of histones and plasma proteins; (2) the clearance of peptides and residual proteins; and (3) the solid phase extraction of cfDNA. During operation, plasma flows through region 1, where proteinase K is immobilized to release the cell free DNA from histones, and digest endogenous proteins found in plasma. Next, fluid is transported to region 2 where peptides are cleared using electrostatic interactions. An immobilization buffer is introduced through the auxiliary port, where the buffer mixes with the sample in a passive mixing channel. Finally, fluid passes into region 3 where the cell free DNA is extracted. The dimensions of the pillars within region 3 can be can be selected to maximize recovery of the cell free DNA molecules. The output of the sample processing device can be connected to a nanochannel detector through the output port.

Sample processing elements of this type can be fabricated using techniques known in the art. An optical mask can be used to selectively expose only region 1 of the assembled device (substrate and sealed with a cover plate) to UV/O$_3$ light. This process forms a scaffold of surface-confined —COOH groups only in the exposed region of the device (defined by optical mask). A proteolytic enzyme (e.g., proteinase K) used to digest histones and plasma proteins can then be covalently attached to surfaces within region 1. This can be accomplished by loading the device with 1-ethyl-3-[3-dimethylaminopro-pyl]carbodiimide hydrochloride (EDC) and N-hydroxy-succinimide (NETS) in buffer (pH 6.0) to form a succinimidyl ester intermediate where the —COOH groups are present. This intermediate can then be reacted with a primary amine group in proteinase K to covalently tether the protein.

Following attachment of proteinase K, the remaining portions of the device (other than region 1) can be exposed to UV/O3 light to induce the formation of a negative surface within these portions of the device. As a consequence, when plasma that has been proteolytically digested enters region 2, peptide fragments and non-digested proteins are removed electrostatically due to the negatively charged surface of region 2 when operated above the pKa of the surface carboxylic acids (pKa ~4.8).

Region 3 serves as the extraction bed for cfDNA once activated with UV/O3 light. The output from region 2 is shuttled to region 3 through an interconnecting channel, where the immobilization buffer is introduced through the auxiliary port. The interconnecting channel also includes a herringbone mixer to facilitate mixing between the plasma and the immobilization buffer.

In some embodiments, the sample processing region can comprise one or more fluidically coupled sample handling elements that together enrich the concentration of an analyte present in the sample introduced into the sample processing region. For example, the two or more fluidically coupled sample handling elements can comprise an enrichment bed fluidically coupled to a microchannel.

Figure 4A:
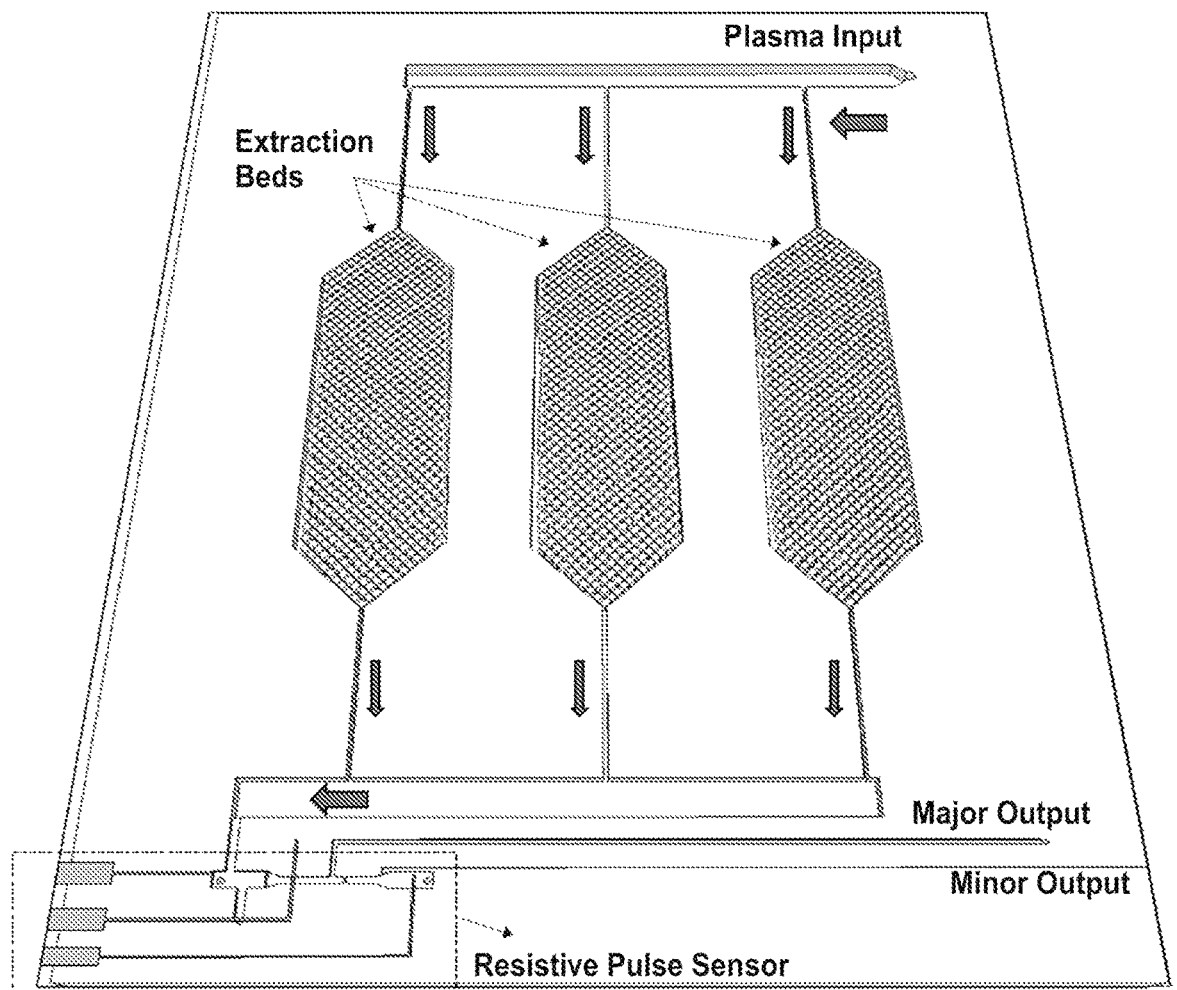
FIG. 4A is a schematic illustration of an example sample processing element that can be used to extract exosomes from plasma. The sample processing element includes one or more solid-phase purification beds comprising pillars (e.g., diamond-shaped pillars) that are surface decorated with monoclonal antibodies. The output of the sample processing device can be connected to a nanochannel detector.
Figure 4B:
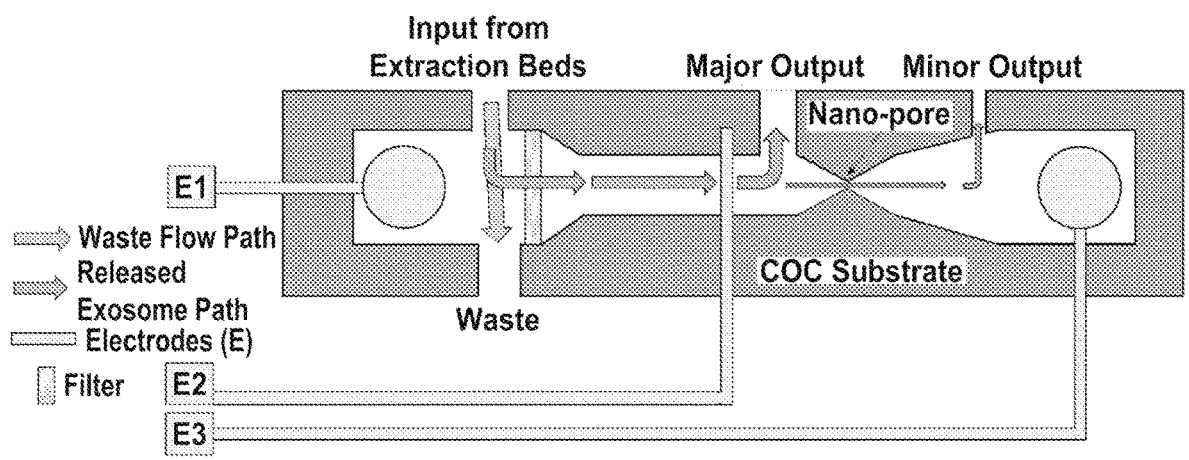
FIG. 4B illustrates an example nanochannel detector (resistive pulse sensor) for counting and sizing individual exosomes following their affinity selection from plasma, for example, using the sample processing element illustrated in FIG. 4A. Following UV-induced release of the exosomes from the capture surface, the exosomes are shuttled through the sensor via hydraulic pressure applied at the wash buffer reservoir (see FIG. 4A) and exerting a positive pressure at the waste reservoir. The effluent is passed through a filter, which also serves as a fluidic resistor. The amount of effluent sent through the nanopore is determined by the hydraulic pressure placed on the major/minor output ports. During nanopore readout, E1 and E3 are used for the bias voltage and E3 is the sensing electrode.

FIGS. 4A and 4B are schematic illustrations of an example sample processing element that can be used to extract exosomes from plasma. The sample processing element includes one or more solid-phase purification beds comprising pillars (e.g., diamond-shaped pillars) that are surface decorated with monoclonal antibodies. In some cases, the sample processing element can include multiple beds placed fluidly connected in parallel, which allows for the selective enrichment of a number of different nanovesicles. The device can be made from a plastic. Antibodies can be attached to the polymer activated surfaces using the techniques described above. In some cases, a photocleavable linker can be used to attach the antibodies so that the affinity-selected exosomes can be released intact from the capture surfaces for analysis downstream. The output of the sample processing device can be connected to a nanochannel detector.

Figure 2:
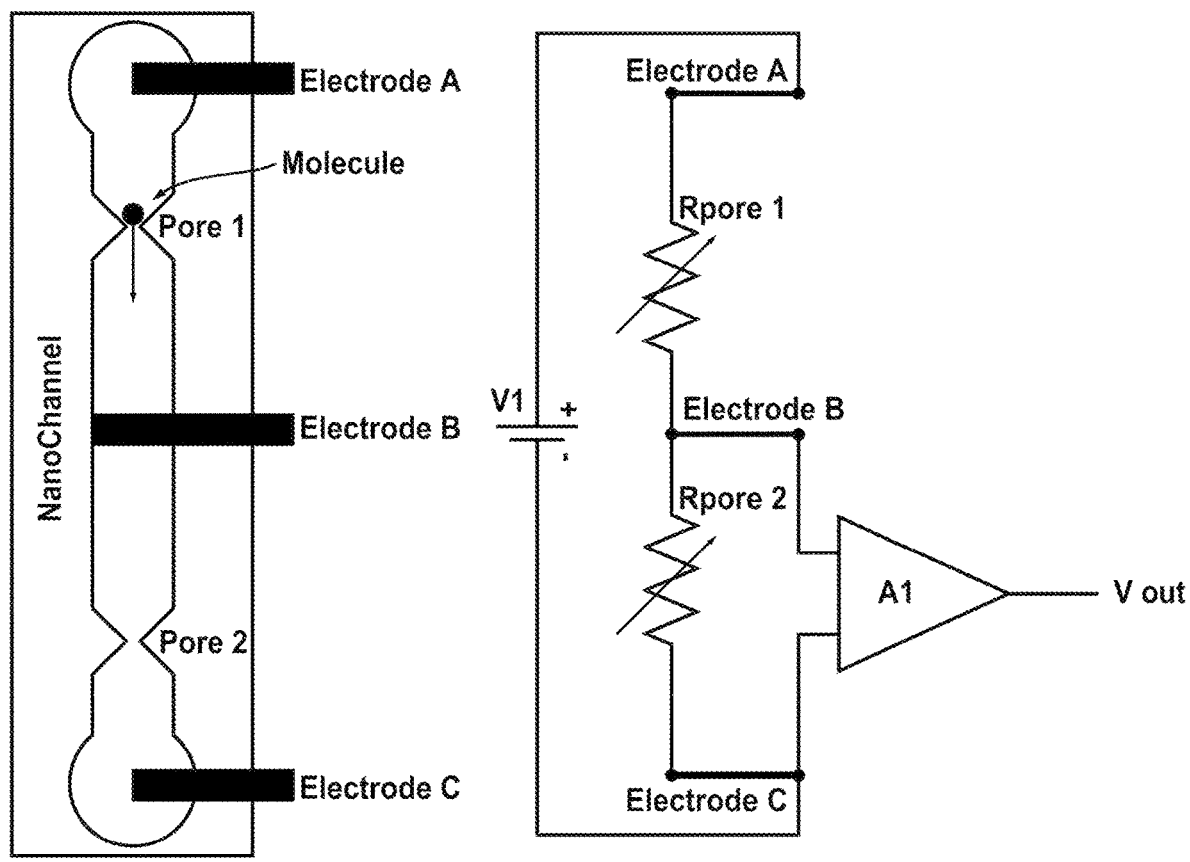
FIG. 2 is a schematic illustration of the electronics for measuring current transients associated with an analyte of interest passing through a nanochannel comprising two in-plane nanopores. The circuitry provides a pair of peaks having different polarities. This can provide a distinctive signature for a single molecule or analyte passing through the nanochannel.

The devices and systems described herein can further include electronics configured to drive an analyte through the nanochannel. A schematic illustration of example electronics for measuring current transients associated with an analyte of interest passing through a nanochannel comprising two in-plane nanopores is illustrated in FIG. 2. Electrodes are placed in reservoirs flanking either side of the nanochannel with a third electrode situated in the middle of the nanochannel and poised between a pair of in-plane pores. A standard voltage amplifier circuit with gain can be used to measure the voltage signals. In this measurement scheme, a blockage event in Pore 1 will cause the voltage measured across Pore 1 to increase (positive polarity). A blockage event in Pore 2 will cause the measured voltage to decrease (negative polarity). In this fashion, we can correlate a pair of blockage events to a single molecule and not different molecules (a positive/negative pulse pair represents a single molecule, FIG. 9B, inset). This measurement method offers advantages compared to a current transient measurement method typically employed for nanopore sensing including: (i) A higher SNR; (ii) the noise is directly dependent on pore noise voltage rather than current; (iii) the bandwidth is less dependent on nanochannel parasitic capacitance; (iv) it is easier to design a high bandwidth low noise voltage amplifier; (v) amenable to using a differential amplifier to measure potentials across $R_{pore1}$ and $R_{pore2}$ thus removing common mode noise; and (vi) there is an opposite polarity for $R_{pore1}$ versus $R_{pore2}$ (FIG. 9B, inset). The electrodes can be patterned onto the cover plate of the nanochannel, for example, using an electro-less deposition process. In one example, the electronics package used for the nanochannel readout can have a footprint of ~10" (wide)×6" (deep)×4" (height). The circuitry can provide a pair of peaks having different polarities. This can provide a distinctive signature for a single molecule or analyte passing through the nanochannel. As configured, transients are measured in terms of voltage.

The analytical devices and/or systems described herein can be fabricated using a variety of suitable substrates. For example, in some cases, the substrate can be chosen from a thermoplastic, an elastomer, a paper, a ceramic, a glass, quartz, silicon, or a combination thereof.

In certain examples, the substrate can comprise a glass, quartz or silicon. In these embodiment, the analytic device can be formed by micromachining processes, or nanomachining processes or a combination thereof. For example, the analytical device can be formed by focused ion beam milling, by a combination of electron beam lithography and reactive ion etching, or by a combination of photolithography, reactive ion etching and focused ion beam milling. Those processes for the analytical device can be combined with a size reduction process. For example, the size of the in-plane nanopore can be reduced by irradiation of high energy electron or ion beams, thermal oxidation process, deposition of a material, or the combination thereof. The pore reduction can also be performed during the thermal fusion bonding of a cover plate.

In certain examples, the substrate can comprise a thermoplastic. In these embodiments, the analytical device and/or systems can be formed by a process that comprises molding or imprinting the substrate. For example, the analytical device and/or systems can be formed by nanoimprint lithography (NIL), injection molding, or a combination thereof. The mold can be fabricated in a glass, quartz, or silicon by micromachining processes, or nanomachining processes or a combination thereof. The mold can also be formed in metals, polymeric materials, or inorganic compounds via replicating the device structure formed in a glass, quartz or silicon. In this case, the device structure formed in a glass, quartz, or silicon is used as master mold. For example, a metal mold can be fabricated via an electrodeposition (or electroplating) process from a master mold. A polymeric mold can be fabricated via thermal or UV NIL from a master mold. For example, a polymeric mold can be formed in polyurethane acrylate (PUA), polydimethyl siloxane (PDMS), fluorine-containing MD 700 UV resin, tripropyleneglycol diacrylate (TPGDA)-based UV resin, or polypropyleneglycol diacrylate (PPGDA)-based UV resin. An inorganic compound mold can be fabricated via UV or thermal NIL. For example, an inorganic compound mold can be formed in Hydrogen silsesquioxane (HSQ) or polysilazane. Those processes for the analytical device can be combined with a size reduction process. For example, the size of the in-plane nanopore formed in polymeric material can be reduced by applying a pressure on the substrate or cover plate, irradiation of high energy electron or ion beams, oxidation process, deposition of a material, or the combination thereof. The pore reduction can also be performed during the thermal fusion bonding of a cover plate.

Also provided herein are substrate wafers (also referred to herein as chips) that comprise a plurality of the analytical devices and/or systems described herein. In some cases, the plurality of devices and/or systems fabricated in the substrate wafer can be fluidically independent. In other cases, the plurality of devices and/or systems fabricated in the substrate wafer can be fluidically connected in parallel such that the sample processing region of each of the plurality of devices and/or systems is fluidically coupled to a common wafer sample inlet.

In some embodiments, a device and/or system can include two different nanochannels coupled together either in series or orthogonally. Each nanochannel can include a pair of in-plane nanopores poised at the input end and output end of the nanochannel. If desired, different separation mechanisms can be employed in each nanochannel to increase in the number of components that can be successfully analyzed and/or identified via their time-of-flight (analogous to the peak capacity sometimes used in multi-dimensional chromatography). Whereas a 1-D separation technique may be sufficient to map a single protein peptide digest (a few tens of peptides, a five proteins digest may already be beyond the resolving power of most 1-D separation techniques. However, the peak capacity of orthogonal separations (i.e., uncorrelated in their separation mechanism) is the product of individual peak capacities. As a consequence, the coupling of two 1-D separations can easily reach a peak capacity in the thousands range. By way of example, in some cases, the first dimension of the coupled nanochannels can include a hydrophobic surface that can produce unique flight times based on the hydrophobicity characteristic of the analyte of interest. The second nanochannel can comprise a charged surface that can produce characteristic flight times based on the ionic character of the analyte of interest.

Methods of Use

The devices described herein can find application in a variety of analytical application. For example, the devices described herein can be used to sequence nucleic acids, identify proteins and polypeptides, and characterize nanoparticles (e.g., synthetic nanoparticles, viral capsids, or exosomes).

In some cases, the devices described herein can be used for sequencing nucleic acids. Methods for sequencing a nucleic acid can comprise providing a device described herein including a bioreactor in which a suitable cleaving enzyme (e.g., exonuclease or exoribonuclease) is immobilized; feeding a sample comprising a nucleic acid molecule into the bioreactor chamber of the device under conditions effective for the cleaving enzyme within the bioreactor chamber to engage the nucleic acid molecule and cleave the nucleic acid molecule into monomer nucleotides that individually enter the input end of the nanochannel; applying an electric field across the bioreactor chamber and along the length of the nanochannel to transport the monomer nucleotides through the nanochannel; detecting, based on said applying, the monomer nucleotides as they pass through the first nanopore and the second nanopore; measuring, based on said detecting, (i) how long it takes for each monomer nucleotide to pass between the first nanopore and the second nanopore, and/or (ii) electrical peak amplitude of the monomer nucleotide as it passes through at least one of the first nanopore and the second nanopore; and identifying the monomer nucleotides based on said measuring. In some embodiments, the method can further comprise obtaining, based on the identifying, at least a portion of a nucleotide sequence of the nucleic acid molecule in the sample.

Nucleic acid molecules that can be sequenced using these methods include, without limitation, deoxyribonucleic acid (DNA) molecules and ribonucleic acid (RNA) molecules. Specifically, double stranded DNA, single stranded DNA molecules, DNA and RNA molecules comprising one or more methylated nucleotide bases, DNA and RNA molecules comprising one or more modified or damaged nucleotide bases. In particular, these methods can readily identify DNA and RNA molecules comprising one or more nucleotide base insertions, deletions, translocations, and mutations, especially when present in a sample in low abundance. When the one or more nucleic acid molecules is a double-stranded DNA molecule, the method affords the ability to identify at least a portion of monomer nucleotides from both strands of the double-stranded DNA molecule. RNA molecules that can be sequenced using these methods include, e.g., long non-coding RNA (lncRNA), ribosomal RNA (rRNA), small nuclear RNA (snoRNA), microRNA (miRNA), transfer RNA (tRNA), and small interfering RNA (siRNA)), and RNA/DNA hybrid molecules. The one or more nucleic acid molecules can be isolated from any biological source, including, without limitation, tissue, cells, serum, plasma, blood, or exosomes.

In some cases, the devices described herein can be used to identify a protein or polypeptide. Methods for identifying a protein or polypeptide can comprise providing a device described herein including a bioreactor in which a suitable cleaving enzyme (e.g., a protease) is immobilized; feeding a sample comprising a protein or polypeptide into the bioreactor chamber of the device under conditions effective for the cleaving enzyme within the bioreactor chamber to engage the protein or polypeptide and cleave the protein or polypeptide into peptide fragments that individually enter the input end of the nanochannel; applying an electric field across the bioreactor chamber and along the length of the nanochannel to transport the peptide fragments through the nanochannel; detecting, based on said applying, the peptide fragments as they pass through the first nanopore and the second nanopore; and measuring, based on said detecting, (i) how long it takes for each peptide fragment to pass between the first nanopore and the second nanopore, and/or (ii) electrical peak amplitude of the peptide fragment as it passes through at least one of the first nanopore and the second nanopore; and identifying the protein or polypeptide in the sample based on said measuring of the peptide fragments.

In some embodiments, the identification step can comprise comparing measurements (i) and (ii) of the peptide fragment to a library of corresponding measurements of peptide fragments generated by cleavage of known proteins or polypeptides to identify the protein or polypeptide in the sample.

The human genome has identified about 21,000 protein coding genes, and with alternative splicing these yield about 100,000 different cellular proteins. The vast majority of these proteins undergo post-translational modifications such as phosphorylation, acetylation, and methylation, and such modifications often play a critical role in the function and active state of the protein.

The complexity of the analysis can be reduced by adding an initial step to fractionate or enrich the desired proteins from a sample containing a plurality of proteins. This fractionation step is easily added by integrating discrete modules into the device of the present invention that using a modular integration approach. This fractionation step may be dependent on a physical property, such as separation by size, charge, or hydrophobicity, using for example chromatography. The fractionation may also depend on affinity to an antibody, a small molecule, or a macromolecule. For example an antibody enrichment step, or isolating the proteins associated with a given transcription factor (also pulled down by specific antibodies). Alternatively, proteins may be enriched for by binding to one or more of a family of phosphorylated, methylated, or acetylated peptides, or other protein domains, or methylated DNA, or specific DNA sequences, or a family of DNA sequences, or common substrates such as ATP or GTP or their analogues, and may be fractionated by affinity purification on a solid support containing covalently attached substrates or their analogues. Other approaches to fractionate the input proteins include separation by subcellular compartment such as nucleus, cytoplasm, mitochondria, endoplasmic reticulum, golgi, cell membrane, nuclear membrane, lysozome, or association with DNA, RNA, chromatin, other protein scaffolds. Fractionation may be designed to enrich for a group of proteins including, but not limited to: G-protein coupled receptors, nuclear receptors, voltage gated ion channels, ligand gated ion channels, receptor tyrosine kinases, growth factors, proteases, sequence specific proteases, phosphatases, protein kinases, bioactive lipids, cytokines, chemokines, ubiquitin ligases, viral regulators, cell division proteins, scaffold proteins, DNA repair proteins, bacterial ribosomes, histone deacetylases, apoptosis regulators, chaperone proteins, serine/threonine protein kinases, cyclin dependent kinases, growth factor receptors, proteasome, signaling protein complexes, protein/nucleic acid transporters, and viral capsids As individual proteins are fed into the bioreactor chamber, the immobilized cleaving enzyme, i.e., a protease, digests the protein to completion, and the fragments are separated and detected in one or more nanochannels using either capillary electrophoresis or capillary electrochromatography. This separation and detection creates a fingerprint for that given protein. If a certain residue is modified, e.g., a lysine is acetylated, the mobility of that fragment will be modified compared to the same fragment containing a non-acetylated lysine. Alternatively, the acetylation may prevent enzyme cleavage at that position that would normally occur (e.g., trypsin will not cleave at an acetylated residue), changing the peptide fingerprint. Using a database containing measurements or fingerprints of peptide fragments cleaved from known proteins with known modifications, one can compare the pattern acquired for the unknown proteins/polypeptides in a sample to the database to identify and characterize the proteins/polypeptides in the sample. Importantly, this analysis is performed at the single molecule level, therefore, rare modifications can be observed that are not manifested using conventional protein processing protocols that utilize many different forms of mass spectrometry.

Also provided are methods for characterizing nanoparticles. Methods for characterizing nanoparticles can comprise providing a device described herein; feeding a sample comprising the nanoparticles into the sample processing region of the device; applying an electric field across the sample processing region and along the length of the nanochannel to transport the nanoparticles through the nanochannel; detecting, based on said applying, the nanoparticles as they pass through the first nanopore and the second nanopore; measuring, based on said detecting, (i) how long it takes for the nanoparticles to pass between the first nanopore and the second nanopore, and/or (ii) electrical peak amplitude of the nanoparticles as the pass through at least one of the first nanopore and the second nanopore; and characterizing the nanoparticles in the sample based on said measuring of the nanoparticles.

In some embodiments, the characterization step can comprise counting the number of nanoparticles in the sample, determining the size of the nanoparticles, determining the size distribution of the nanoparticles in the sample, determining the zeta potential of the nanoparticles, or a combination thereof.

In some embodiments, the nanoparticles can comprise exosomes. In some of these embodiments, the sample can comprise a biological fluid and wherein the sample processing region of the device extracts and enriches the exosomes from the biological fluid.

By way of non-limiting illustration, examples of certain embodiments of the present disclosure are given below.

EXAMPLES

Example 1: Analytical Device for Single Molecule Sequencing (SMS)

Figure 5A:
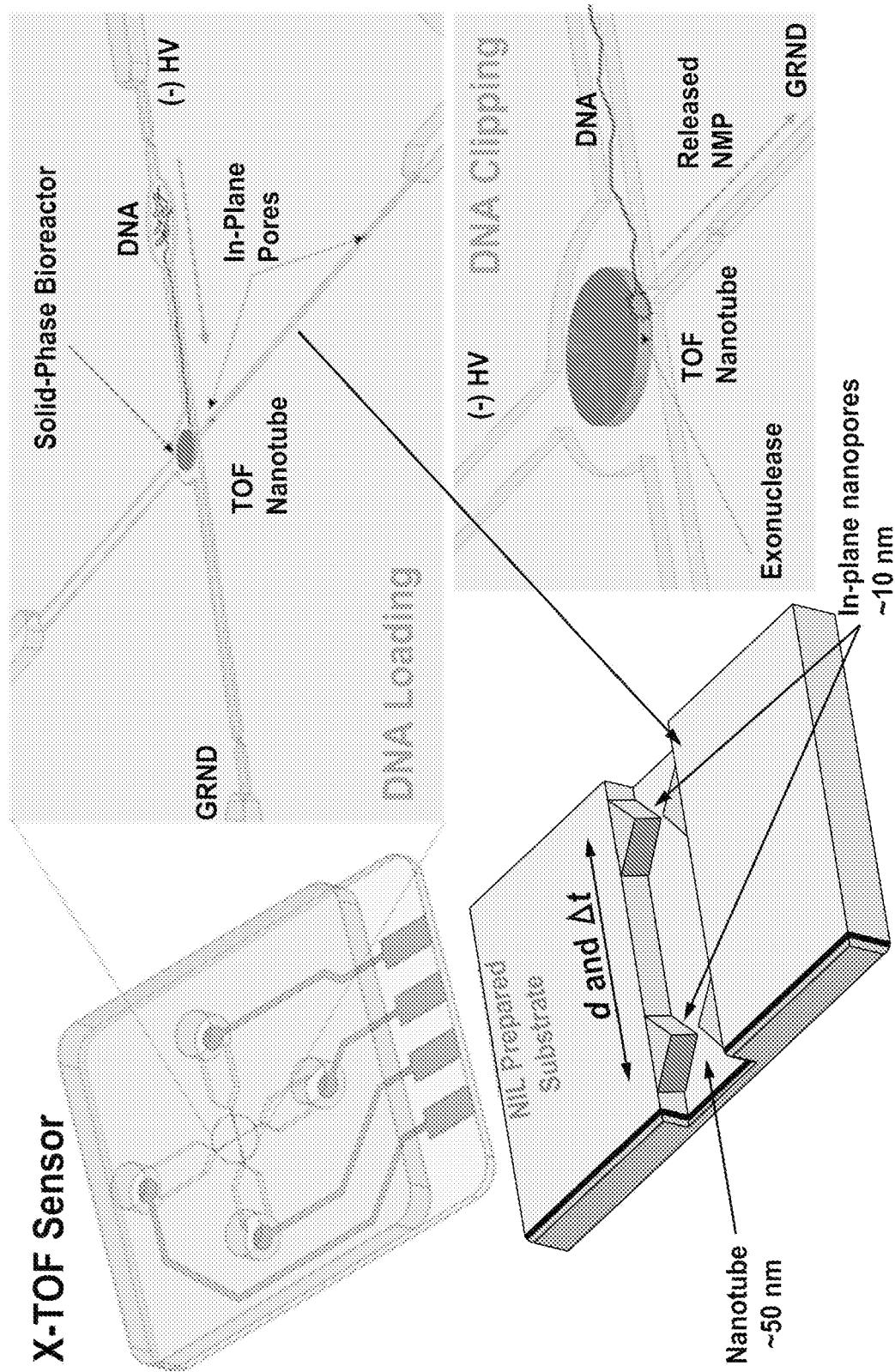
FIG. 5A is a schematic illustration of an analytical system designed for use in single molecule sequencing (SMS). In this example, the device accepts double stranded DNA (dsDNA) input molecules and deduces their primary sequence by the sequential clipping of the input dsDNA molecule using an exonuclease enzyme. The single deoxynucleotide monophosphates (dNMPs) generated are moved through a nanochannel that produces a molecular-dependent flight time used for dNMP identification. The flight time is measured using a pair of in-plane nanopores poised at the input and output ends of the nanochannel, which is made from the appropriate material to suit the application need and the structures produced via micro- and nano-replication technologies. The nanosensor uses electrical signatures to monitor the input of dsDNA, immobilized exonuclease to complex the dsDNA, entropic traps to stretch the dsDNA and identify the clipped dNMPs using flight-times through 2D nanochannels. The same format can be used to process RNA molecules.

An example analytical device structured for use in single molecule sequencing (SMS) applications is illustrated in FIG. 5A. A pre-processed DNA fragment (~50 kbp) is electrokinetically directed through a nanochannel flight tube ~50 nm in width and height, similar to the persistence length of dsDNA, and into a bioreactor chamber. Located within the bioreactor chamber is a highly processive exonuclease, such as λ-exonuclease, that is covalently tethered to a pillar support via a linker using polymer-based modification chemistries. The initiation of the sequencing run is affected by applying an electric field across the nanochannel containing a plurality of in-plane nanopores positioned along the nanochannel in series. The in-plane nanopores can be used to measure the flight-time of single individual deoxynucleotide monophosphates (dNMPs) sequentially cleaved by the processive exonuclease. The application of this field also introduces $Mg^{+2}$ into the bioreactor to activate the exonuclease. The released dNMPs are electrokinetically transported through the nanochannel with the flight-time determined by the applied electric field, the length (d) of the nanochannel and the molecular-dependent electrophoretic mobility of the dNMPs. Because the mobilities are molecular dependent, the flight-times will provide a direct indicator of the identity of the dNMPs. Therefore, our base identification protocol is predicated on molecular-specific electromigration, similar to what has been demonstrated for nucleotides using chromatographic techniques. The major difference is that in this approach, the flight-time of single molecules are monitored.

This approach advantageously employs in-plane nanopores fabricated in series along the length of a nanochannel. Because nanochannels can be produced using top-down fabrication strategies, replication-based techniques can generate a low-cost modality for their production, especially if polymers are used.

Figure 5B:
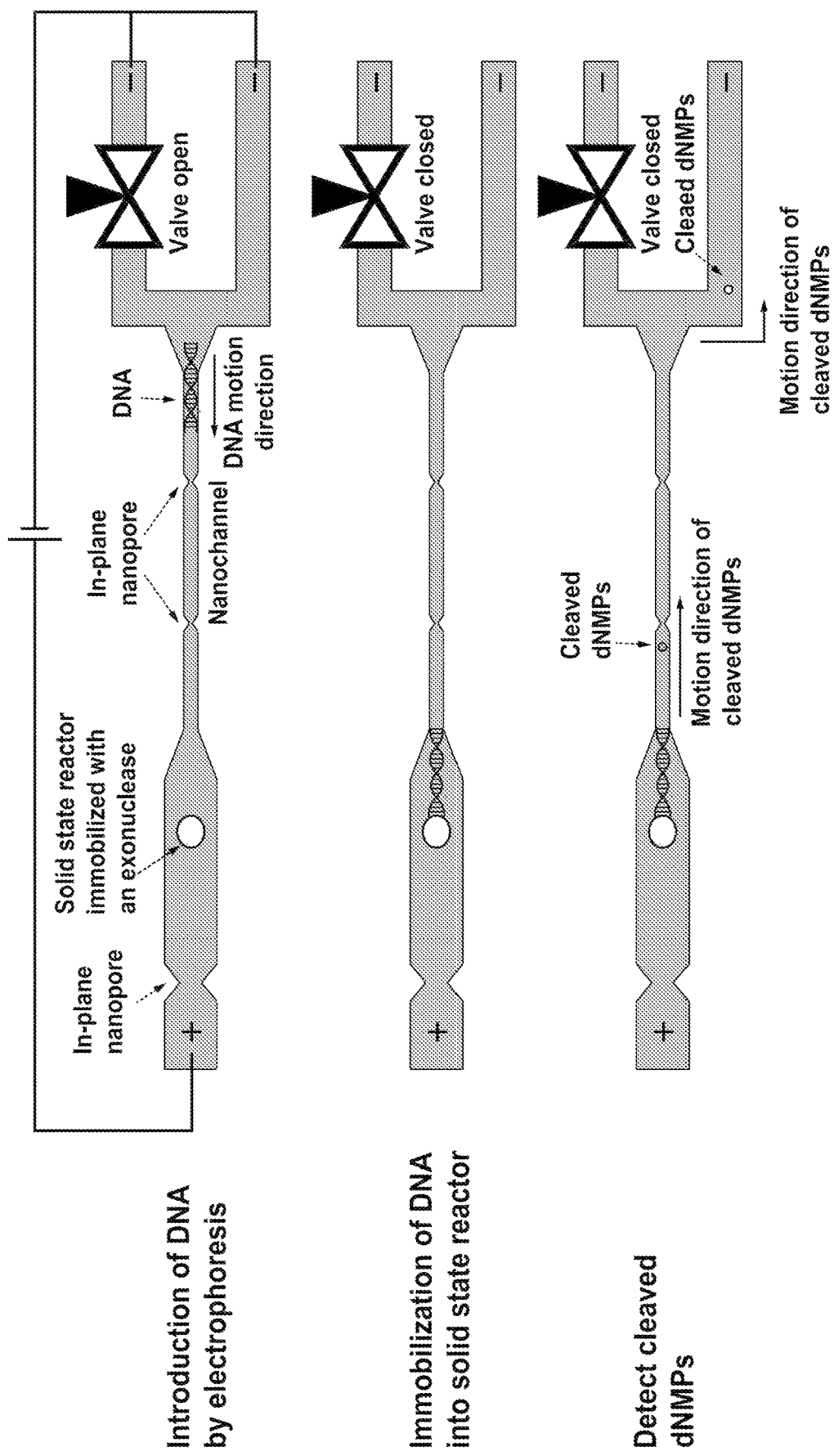
FIG. 5B schematically illustrates another example analytical device structured for use in single molecule sequencing (SMS) applications.

Another example analytical device structured for use in single molecule sequencing (SMS) applications is illustrated in FIG. 5B. In this example, the nanochannel flight tube with in-plane nanopores to be used for detecting the sequentially cleaved deoxynucleotide monophosphates (dNMPs) is also used to electrokinetically direct a pre-processed DNA fragment (~50 kbp) into a bioreactor chamber. Located within the bioreactor chamber is a highly processive exonuclease, such as λ-exonuclease, that is covalently tethered to a pillar support via a linker using polymer-based modification chemistries. The passage of the pre-processed DNA fragment and its reaction at the bioreaction chamber can be monitored by the in-plane nanopores. Once the reaction of the pre-processed DNA fragment at the bioreaction chamber is confirmed, then the valve at a microfluidic inlet channel is closed, so that no more DNA fragment enters into the nanochannel flight tube. An entropic trap can also be used to prevent introduction of more than one pre-processed DNA fragment. In this case, a pulsed increase of the driving voltage can induce introduction of the next DNA fragment into the nanochannel flight tube. The initiation of the sequencing run is affected by applying an electric field across the nanochannel containing a plurality of in-plane nanopores positioned along the nanochannel in series. The effective driving force to move a biomolecule can be controlled in such a way that the direction of the electrokinetic motion of the pre-processed DNA fragment and the cleaved dNMPs is opposite to each other by controlling the surface charge density of the walls of nanopore and nanochannel, and the conditions of the electrolyte. Therefore, immobilization of the pre-processed DNA fragment and the driving the cleaved dNMPs into the nanochannel flight tube with in-plane nanopores can be done without changing the applied electric field. Then, the in-plane nanopores can be used to measure the flight-time of single individual deoxynucleotide monophosphates (dNMPs) sequentially cleaved by the processive exonuclease. The application of this field also introduces $Mg^{+2}$ into the bioreactor to activate the exonuclease. The released dNMPs are electrokinetically transported through the nanochannel with the flight-time determined by the applied electric field, the length (d) of the nanochannel and the molecular-dependent electrophoretic mobility of the dNMPs. Because the mobilities are molecular dependent, the flight-times will provide a direct indicator of the identity of the dNMPs. Therefore, our base identification protocol is predicated on molecular-specific electromigration, similar to what has been demonstrated for nucleotides using chromatographic techniques. The major difference is that in this approach, the flight-time of single molecules are monitored.

Synthetic In-Plane Nanopores

The analytical device includes a time-of-flight nanosensor formed using two or more in-plane synthetic nanopores positioned in series along a nanochannel. Advantageously, the nanopores can be fabricated in the same imprinting step used to produce the nanofluidic network.

Figure 6A:
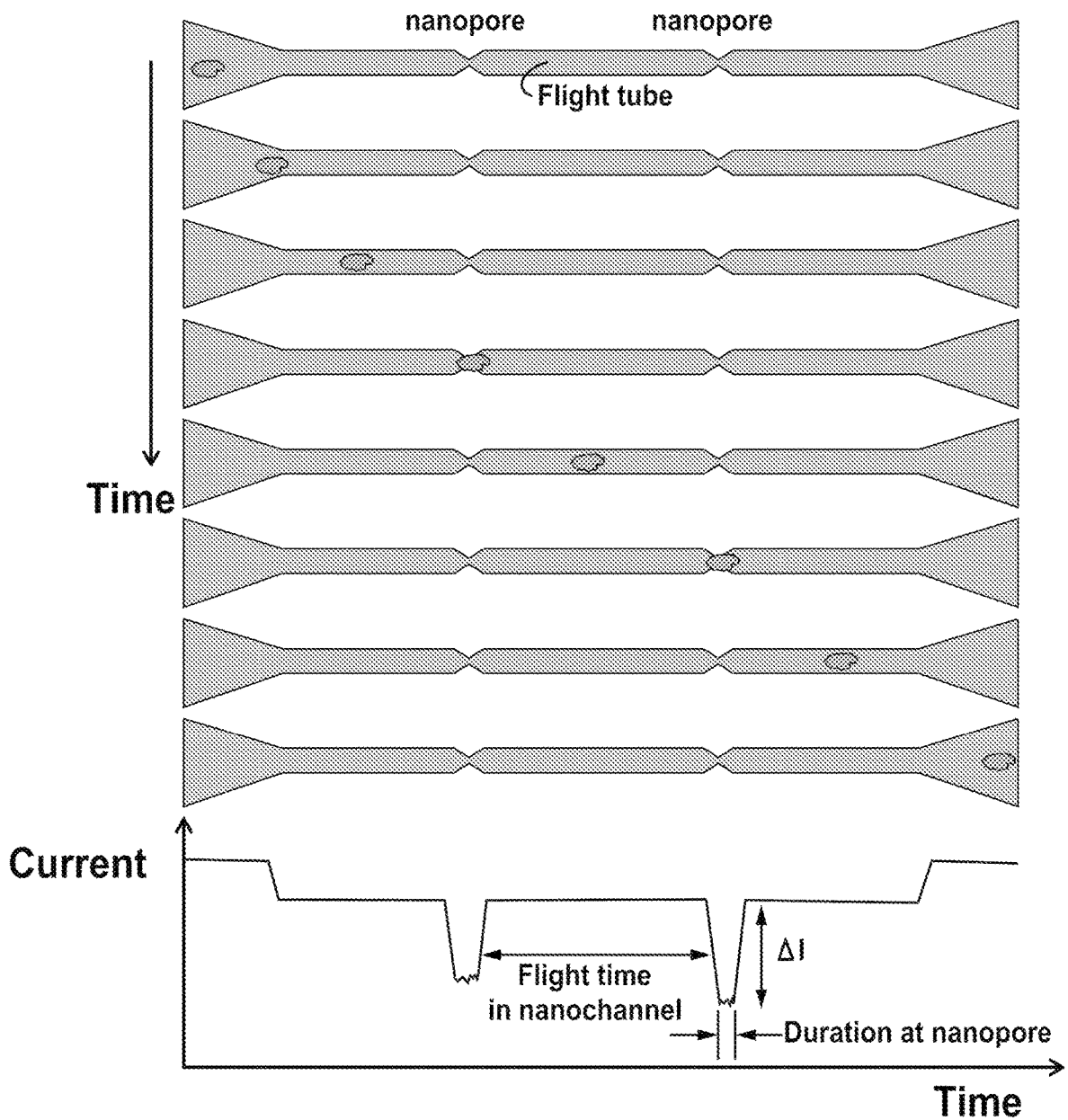
FIG. 6A schematic showing the nanopore readout mechanism for deducing the molecular-dependent flight times of single dNMPs.
Figure 6B:
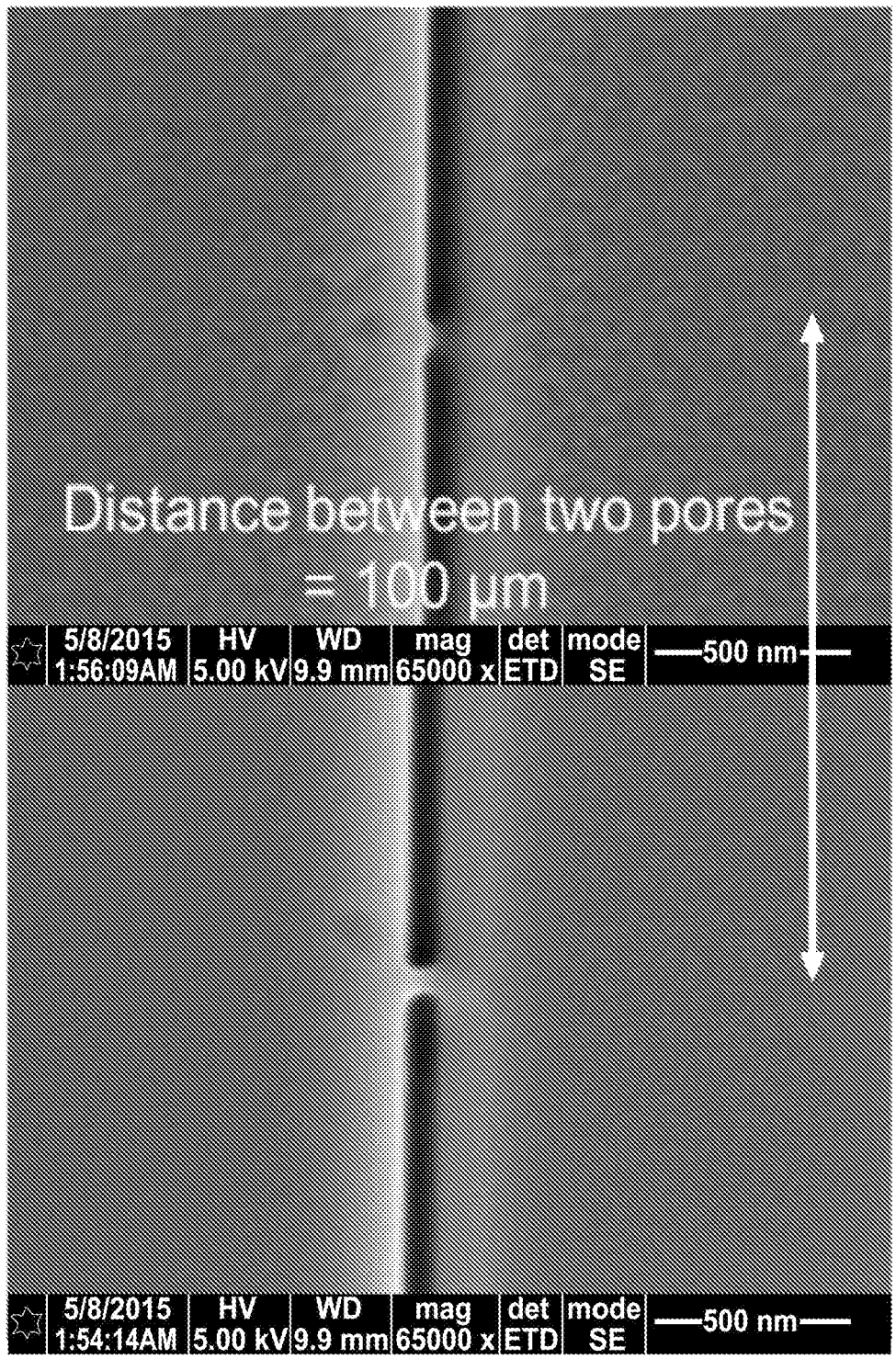
FIG. 6B is an SEM micrograph of a polymeric (e.g., PMMA-based) nanosensor flight tube equipped with 2 nanopores of different sizes. The pores are 3 dimensional—the flight tube is 100 nm deep while the pores are either 50 or 80 nm deep with a length of 50 nm. The flight tube in this case is 100 μm in length with the column width/depth=100 nm.

FIG. 6A illustrates a schematic of the readout process and determining the flight time using the in-plane nanopore-based nanosensor. As can be seen, two in-plane nanopores flank the flight tube to read when the molecule enters the flight tube and when it exits. The flight time is then equal to the time difference between the two current transients produced by the pores. FIG. 6B shows an SEM micrograph of a flight tube and pores produced a PMMA polymer substrate using nanoimprint lithography (NIL). Following enclosure of the device, DNA molecules were successfully translocated through the device.

Figure 6C:
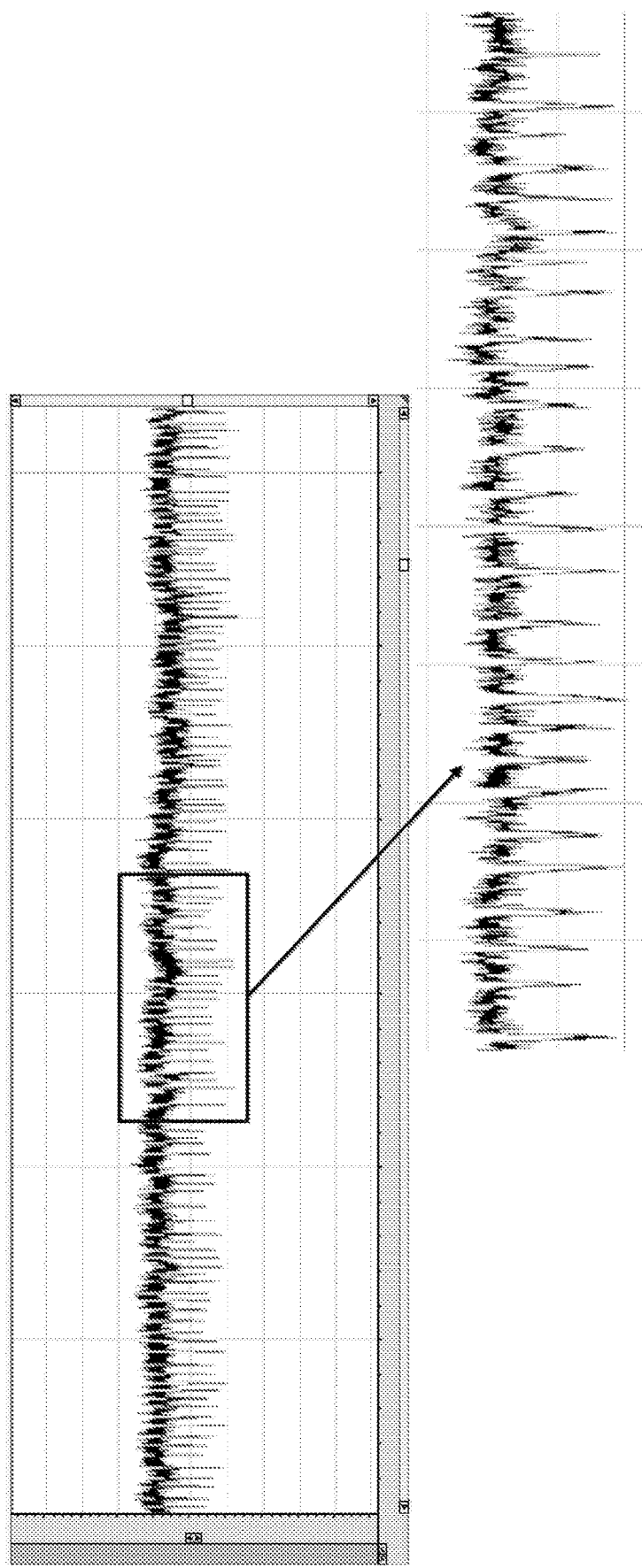
FIG. 6C shows current blockage events for 500 bp single DNA molecules electrophoretically translocating through the device shown in FIG. 6B. The applied voltage in this example was 1 V (E=100 V/cm). The current blockage events were measured using an Axopatch current amplifier.
Figure 6D:
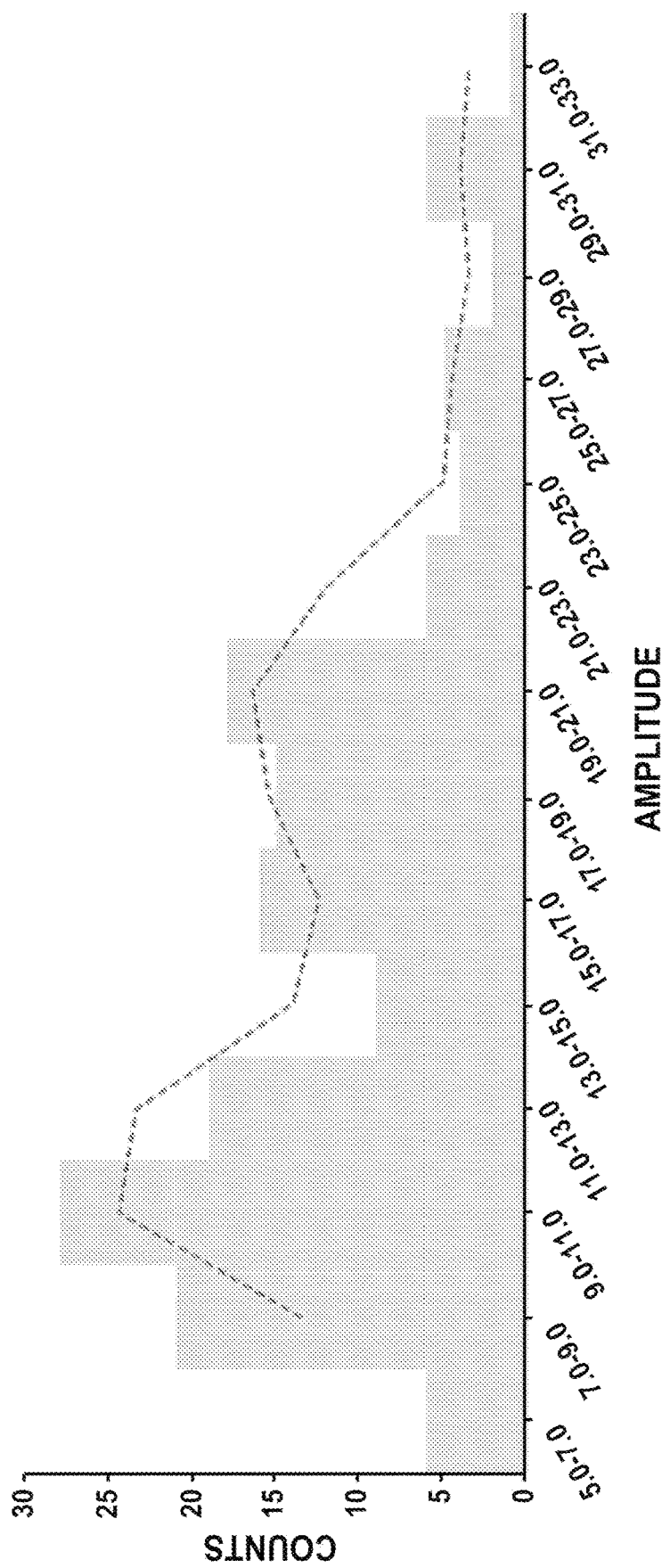
FIG. 6D is a histogram showing the peak amplitude versus frequency for the trace data shown in FIG. 6C. The bimodal distribution in the histograms arises from the DNA traveling through 2 different sized nanopores.

FIG. 6C shows discrete current blockage events arising from single DNA molecules (500 bp, double-stranded) electrophoretically moving through the dual pore system. In order to discern the difference in translocation events arising from the first (top) or the second (bottom) pore, the pore size was altered so that the amplitude of the current transient would be different for each pore (smaller pore ~50 nm—produces a larger amplitude event versus the larger pore –80 nm). Indeed, when the trace data depicted in FIG. 6D was analyzed, a bimodal distribution was observed. By appropriately scaling the size of the pores, analytes of different sizes can be detected. For example, by scaling down the size of the pores, single dNMPs can be detected. Likewise, by increasing the dimensions of the pores, single nanoparticles or virus particles can be detected.

This device design offers several distinct advantages. First, the nanopores can be fabricated in a thermoplastic or UV-curable resist using NIL. In this way, the nanopores can be integrally formed within the nanochannel in the same NIL step that is used to fabricate the fluidic network. In addition, the entire nanosensor along with the readout nanopores can be fabricated in a single NIL step, simplifying construction and making it conducive to high-scale production to allow dissemination of the nanosensor devices to the community at low-cost.

Any number of pores as well as their location on a chip can be produced using the proper imprinting tool. This is attractive, because it facilitates producing a number of nanosensors on a single substrate (e.g., a 6" plastic wafer), for example, for high throughput DNA sequencing applications.

The nanopores can be easily shaped in terms of dimensions (height, width, length, and cross-sectional area). Shaping of the pore is not possible with naturally occurring pores unless site-directed mutagenesis is performed. This allows pores to be formed that generate unique current blockade signatures from even single molecules, such as the dNMPs. This will allow proper registry of a molecule with its location on the chip, such as the entrance or exit nanopores flanking the flight tube. In addition, the size of the pore can be shaped to accommodate detection of different entities in a label-less strategy (single biological cells, exosomes, biopolymers and small molecules).

Because the nanochannel flight tube and in-plane nanopores are formed on the substrate surface, it can be readily integrated with other devices performing pre- and post-processing of biomolecules (e.g., a variety of sample processing regions).

The error occurring in the molecular identification by the time-of-flight measurement can be significantly reduced by combining the analysis of individual pulsed electrical signals produced by each pore. The width and amplitude of a pulsed electrical signal produced by each nanopore can be specific to the translocation of a molecule.

Figure 7:
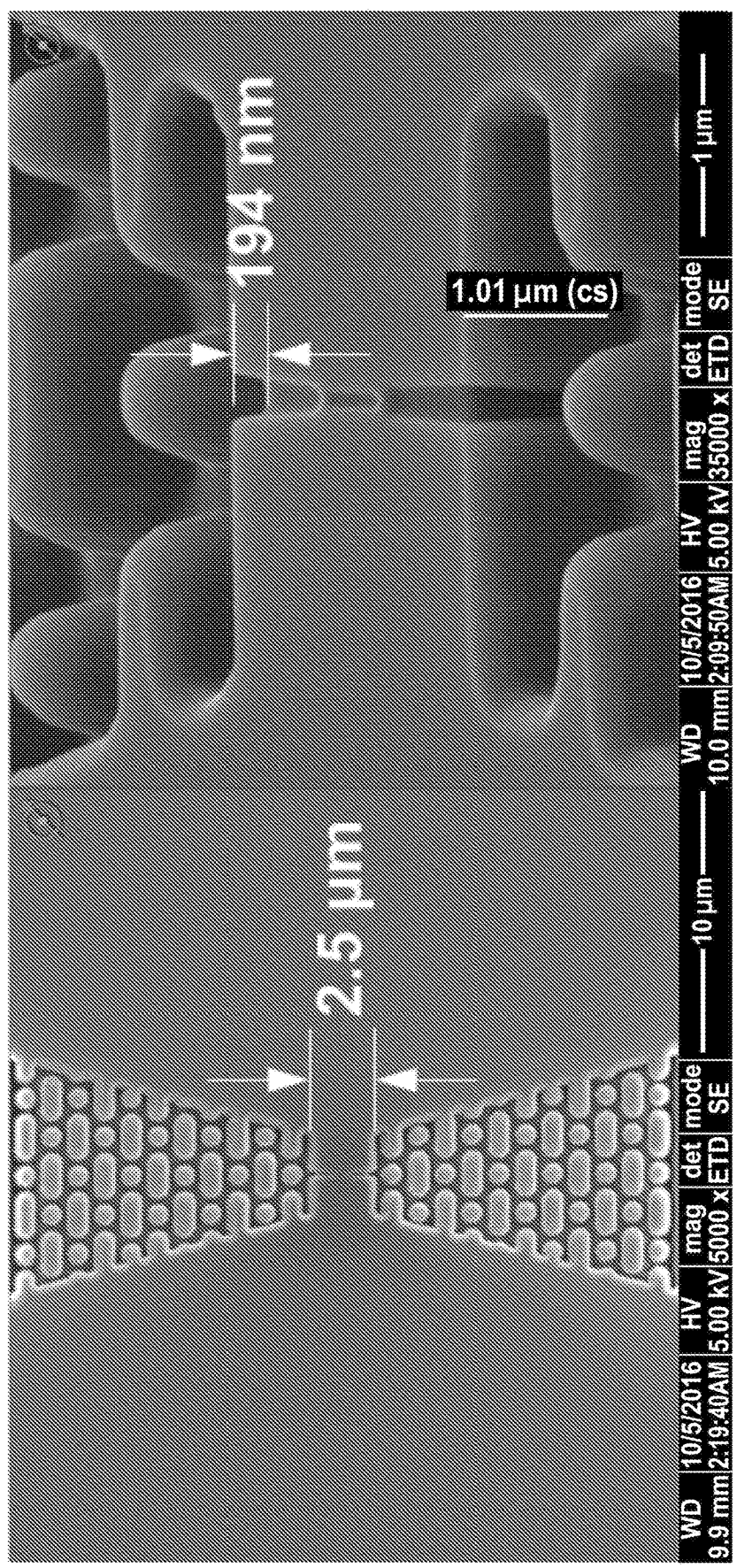
FIG. 7 shows a nanochannel containing a pair of in-plane nanopores fabricated in a poly(ethylene glycol) diacrylate (PEGDA) substrate. The device was prepared by spinning PEGDA on a PMMA substrate, cross-linking the PEGDA, then forming the fluidic channel(s) and nanopores via thermal NIL.
Figure 7:
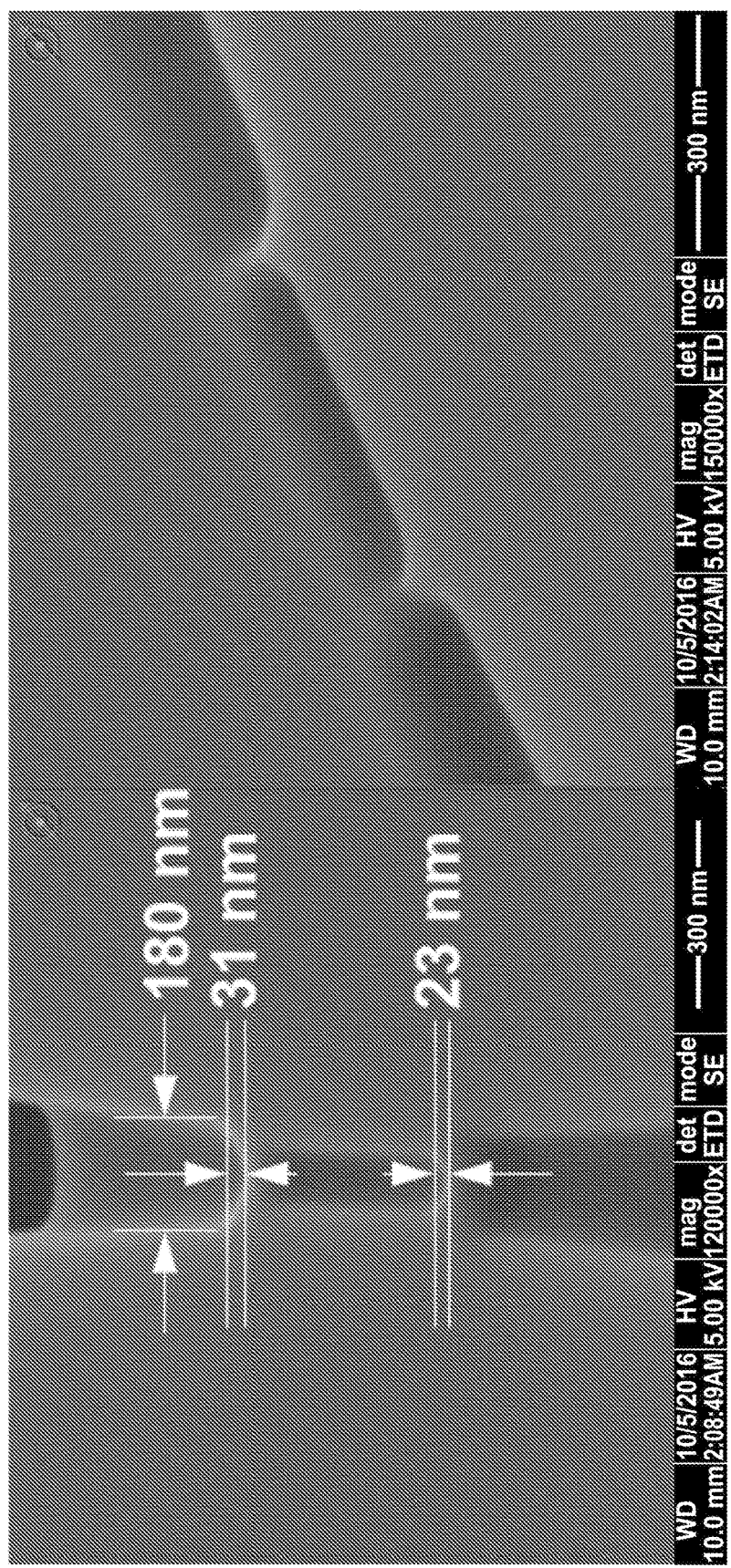
Figure 8A:
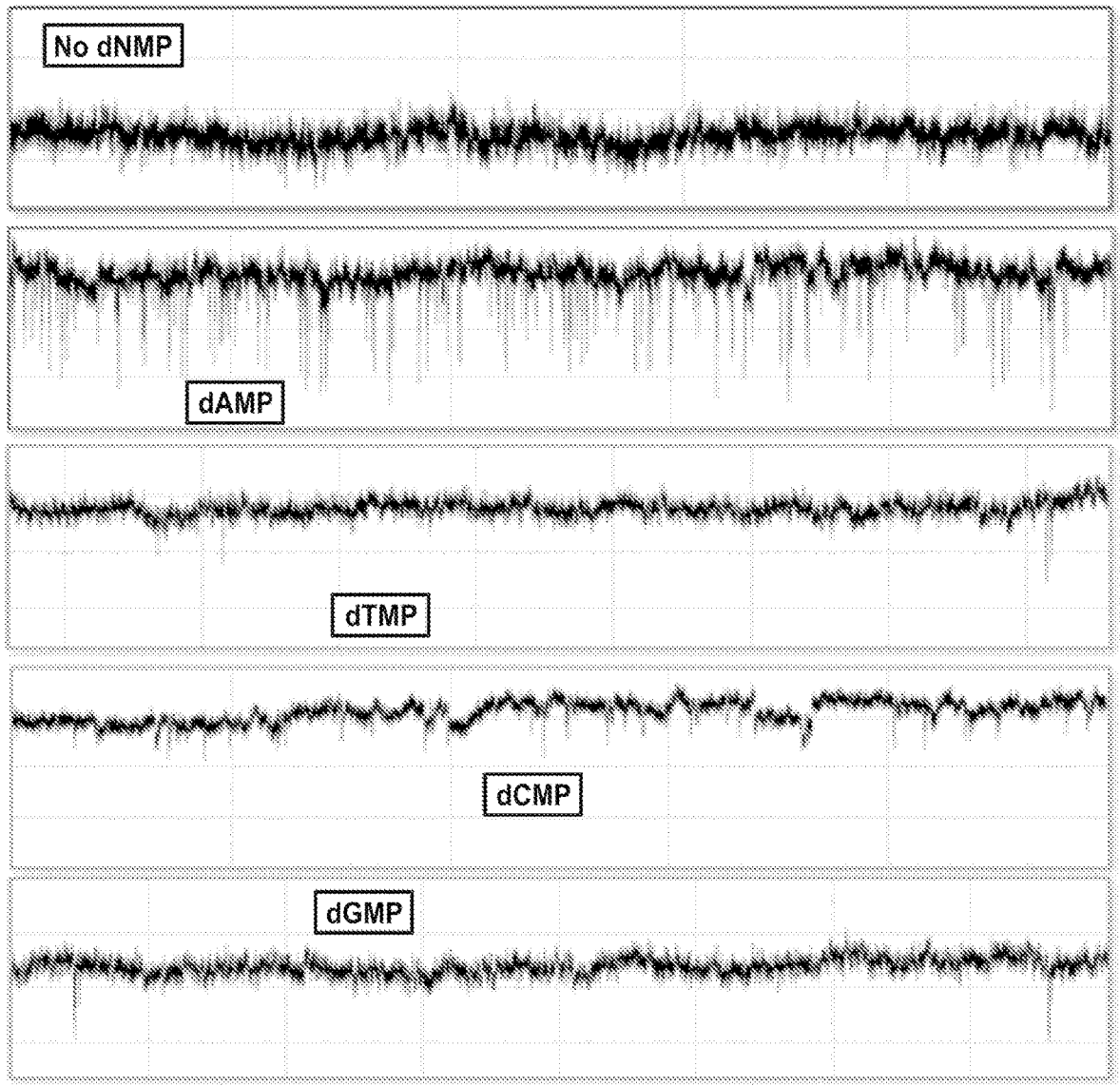
FIG. 8A is a plot showing the current transient data for the dNMPs electrokinetically travelling through a PEGDA flight tube possessing dual in-plane nanopores.
Figure 8B:
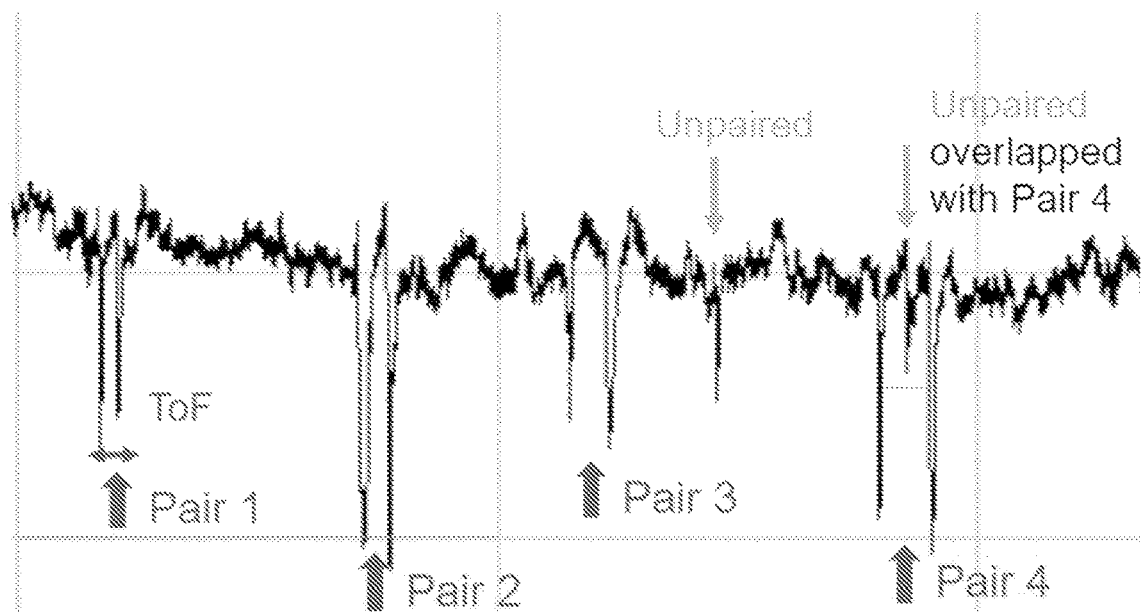
FIG. 8B shows an example transient current which shows several distinct paired peaks.
Figure 8C:
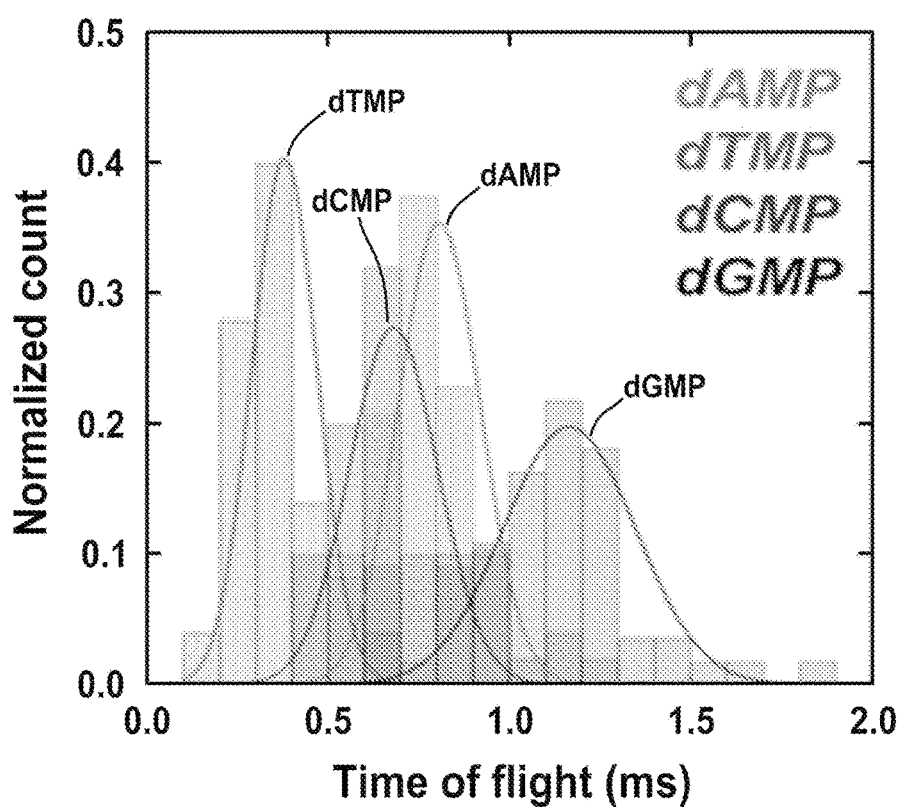
FIG. 8C shows the distribution of the time-of-flight for four dNMP molecules.

FIG. 7 illustrates an alternative fabrication protocol that uses PEGDA as the biocompatible substrate. PEGDA exhibits a high degree of hydrophilicity and thus minimizes the non-specific adsorption of biological molecules to substrate surface. This reduces the effect of electroosmosis when introducing biomolecules into the nanochannel flight tube and nanopores. As a proof-of-principle experiment, these in-plane pores were used to collect data for transducing single dNMP molecules (see FIG. 8A). The dNMPs were electrokinetically moved through a flight tube that was 100 μm in length and about 50×50 nm (width×depth). Signals from dTMP and dGMP show distinct paired peaks from the two in-plane nanopores, from which the time-of-flight of their translocation could be obtained. However, for dAMP and dCMP, it was difficult to identify the paired peaks. By lowering the concentrations of the dNMP solutions, it should be possible to obtain the paired peaks and thus the time-of-flight. As another proof-of-principle experiment, the dNMPs were electrokinetically moved through a flight tube that was 500 nm in length and about 50×50 nm (width×depth). FIG. 8B shows an example transient current which shows several distinct paired peaks. FIG. 8C shows the distribution of the time-of-flight for four dNMP molecules. As determined by the (un-overlapped area)/(total area) for each dNMP, the identification accuracy was 35%, 85%, 24%, and 78% for dAMP, dTMP, dCMP and dGMP, respectively. This leads to the average identification accuracy of 55%. This average identification accuracy was increased to 75% by increasing the flight tube length from 500 nm to 1 μm.

Figure 8D:
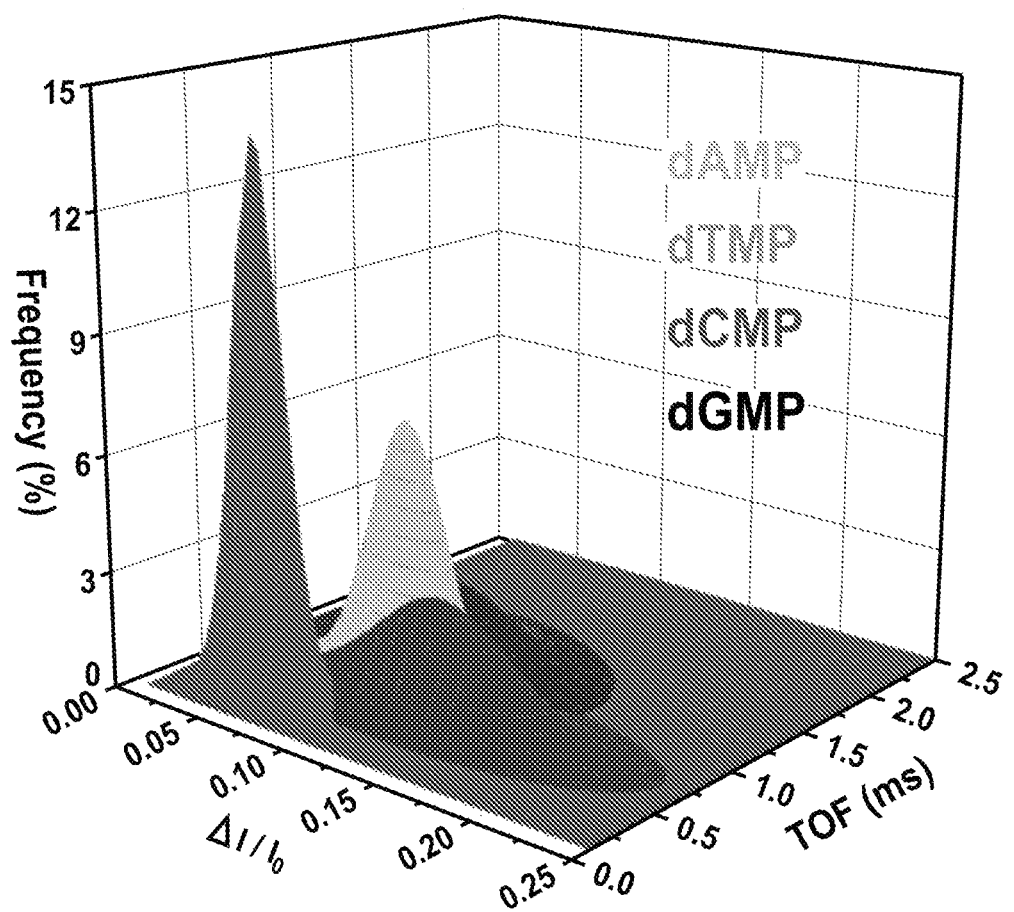
FIG. 8D shows the 2D Gaussian fitted curves from the distribution of the time-of-flight and normalized amplitude of the pulsed electrical signals for four dNMPs obtained with the 500 nm flight tube.

The error occurring in the molecular identification by the time-of-flight measurement can be significantly reduced by combining the analysis of individual pulsed electrical signals produced by each pore. The width and amplitude of a pulsed electrical signal produced by each nanopore can be specific to the translocation of a molecule. As an example, FIG. 8D shows the 2D Gaussian fitted curves from the distribution of the time-of-flight and normalized amplitude of the pulsed electrical signals for four dNMPs obtained with the 500 nm flight tube. As determined by the (un-overlapped volume)/(total volume) for each dNMP, the identification accuracy was improved from 55% to 60%.

Electronics

Using the two longitudinal electrodes positioned at either end of the nanochannel, single dNMPs were driven through the nanochannel and electrical signals from the two in-plane nanopores were measured. However, with this two-electrode system, a translocation event does not always produce a paired peak, particularly when too many molecules are introduced into the sensor structure simultaneously. To address this shortcoming, a three-electrode system was developed.

Figure 9A:
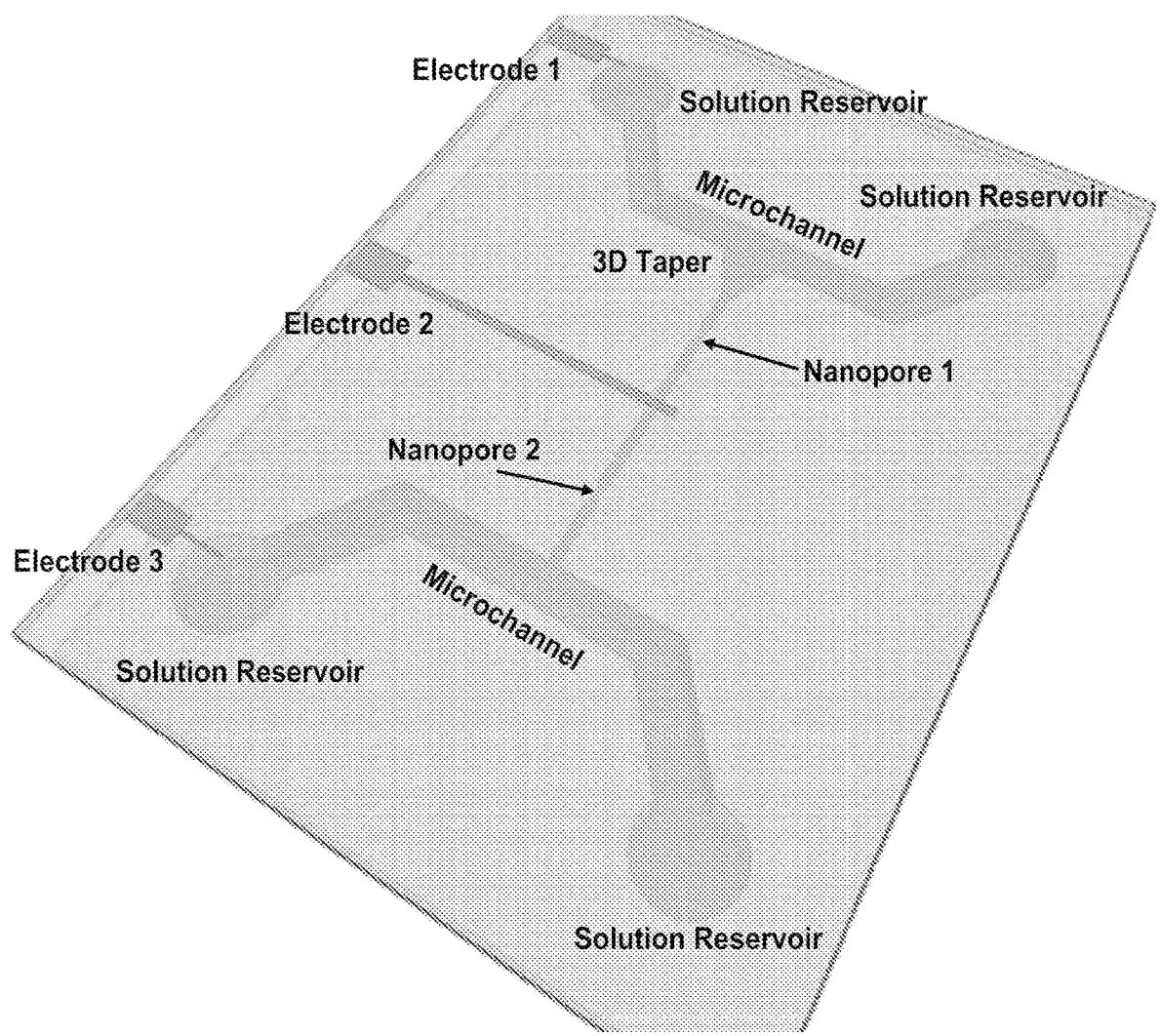
FIG. 9A is a perspective view of an example nanochannel that includes a pair of in-plane nanopores with three electrodes. Two electrodes are positioned at the inlet and outlet microchannels and the third electrode is located across the nanochannel between the two in-plane nanopores.
Figure 9B:
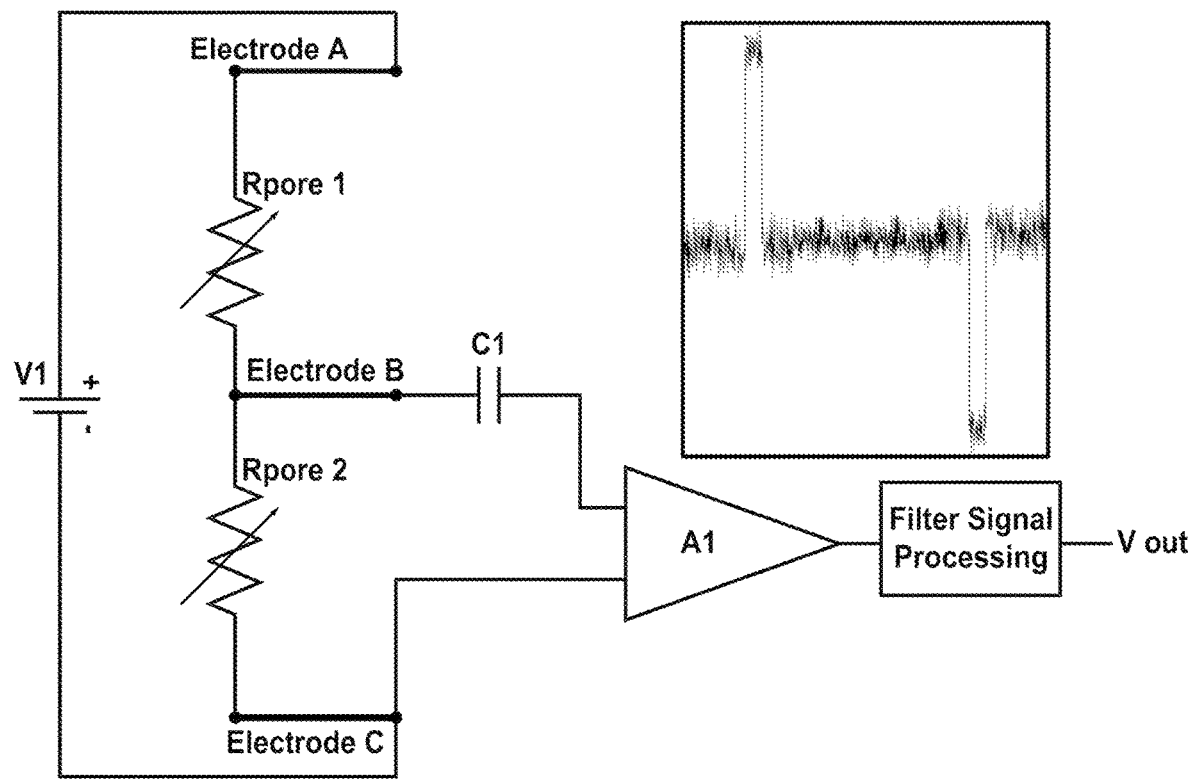
FIG. 9B shows a circuit diagram of the nanochannel with 3 electrodes and measuring circuitry. The inset shows a schematic of a positive/negative pulse pair produced by a single molecule passing through a pair of pores. The duration of the resistive pulses depends on the lengths of the particle (e.g., DNA) passing through the pore.

The measurement modality and electronics for transducing blockage events produced by single dNMPs as they electrophoretically move through in-plane nanopores involves a three-electrode voltage divider network are schematically illustrated in FIG. 9A. Electrodes are placed in reservoirs flanking either side of a nanochannel with a third electrode situated in the middle of the nanochannel between a pair of in-plane pores. A standard voltage amplifier circuit with gain can be used to measure the voltage signals. In this measurement scheme, a blockage event in Pore 1 will cause the voltage measured across Pore 2 to increase (positive polarity). A blockage event in Pore 2 will cause the measured voltage to decrease (negative polarity). In this fashion, a pair of blockage events can be correlated to a single molecule and not different molecules (a positive/negative pulse pair represents a single molecule, FIG. 9B, inset). This effect is optimized when the resistance of the nanopores, which is determined by their cross-sectional area, is identical, so as to generate the largest voltage change for a blockage event. Alternatively, when the resistances of the nanopores differ, a physical resistor can be added to the circuitry in series with the lowest resistance pore to equalize the voltages.

This measurement method offers advantages compared to a current transient measurement method typically employed for nanopore sensing, including: (i) an increased signal-to-noise ratio (SNR); (ii) the noise is directly dependent on pore noise voltage rather than current; (iii) the bandwidth is less dependent on nanochannel parasitic capacitance; (iv) it is easier to design a high bandwidth low noise voltage amplifier; (v) amenable to using a differential amplifier to measure potentials across $R_{pore1}$ and $R_{pore2}$ thus removing common mode noise; and (vi) there is an opposite polarity for $R_{pore1}$ versus $R_{pore2}$ (FIG. 9B, inset). The electronics package used had a footprint of ~10" (wide)×6" (deep)×4" (height).

Although a three-electrode system with voltage measuring electronics is described as the primary method with the largest number of advantages for measuring the blockage events, other techniques can also be used. These include, but are not limited to, the use of current-measurement devices such as TransImpedance Amplifiers (TIAs) as well as a variety of commercial current-measuring instruments. Electrode geometries and types may also be altered to allow use of these alternative methods.

The third electrode situated in the middle of the nanochannel flight tube can be, for example, an evaporated/sputtered metal electrode, a metallic nanowire, a nano-patterned carbon nanotube and/or graphene, or another nanofluidic channel filled with a conductive electrolyte.

Figure 9C:
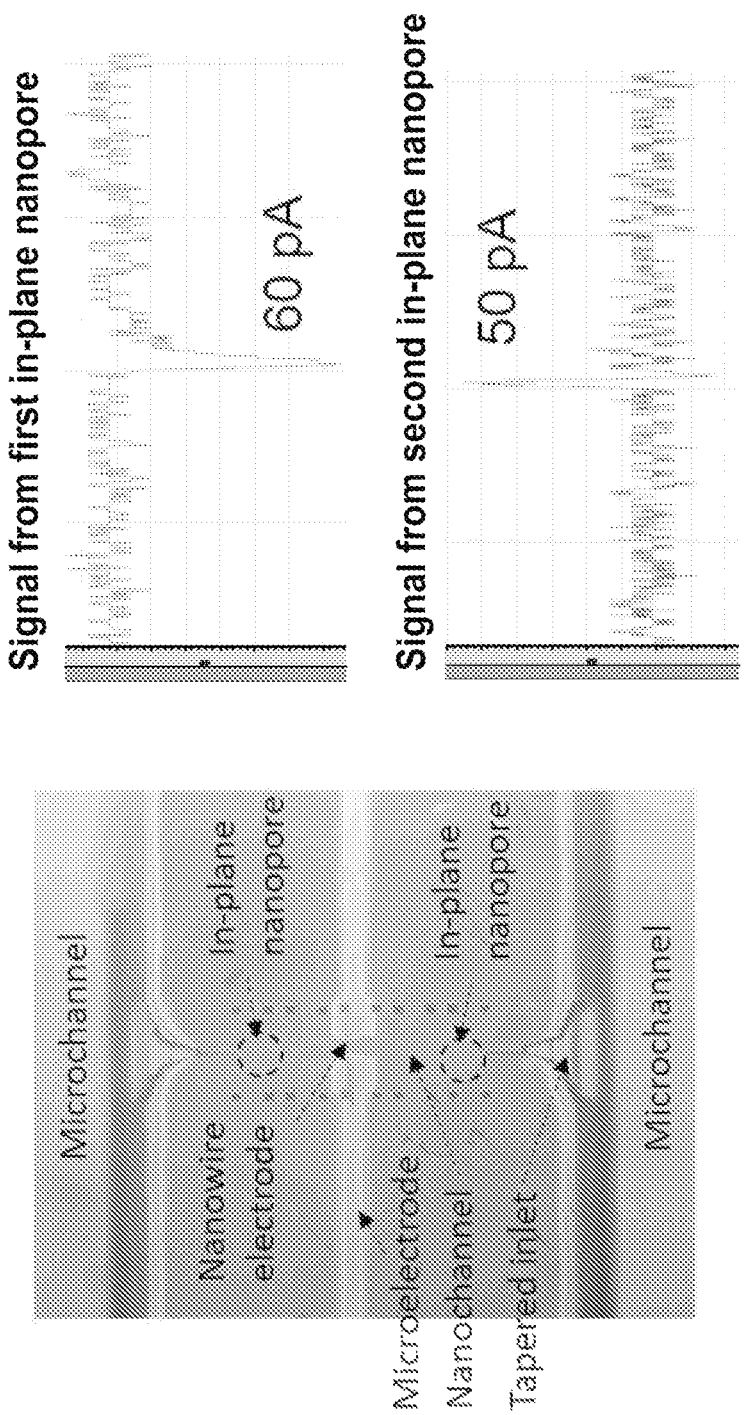
FIG. 9C is an optical micrograph for an example nanochannel containing a pair of in-plane nanopores with three electrodes. Two electrodes are positioned at the inlet and outlet microchannels. The third electrode was a metallic nanowire placed on and connected to a microelectrode formed via sputtering of Pt through a stencil mask. In the right is shown example transient current signals obtained from first and second in-plane nanopores during translocation of λ-DNA.

FIG. 9C shows an example of the three electrode system realized in PMMA substrate. The two electrodes will be positioned at the inlet and outlet microchannels. The third middle electrode is a metallic nanowire placed perpendicular to the nanochannel flight tube. The nanowire electrode was connected to microelectrodes formed via sputtering Pt through a stencil mask. In the right are shown the two transient current peaks measured separated between the top electrode and the middle nanowire electrode and between the bottom electrode and the middle nanowire electrode.

Figure 9D:
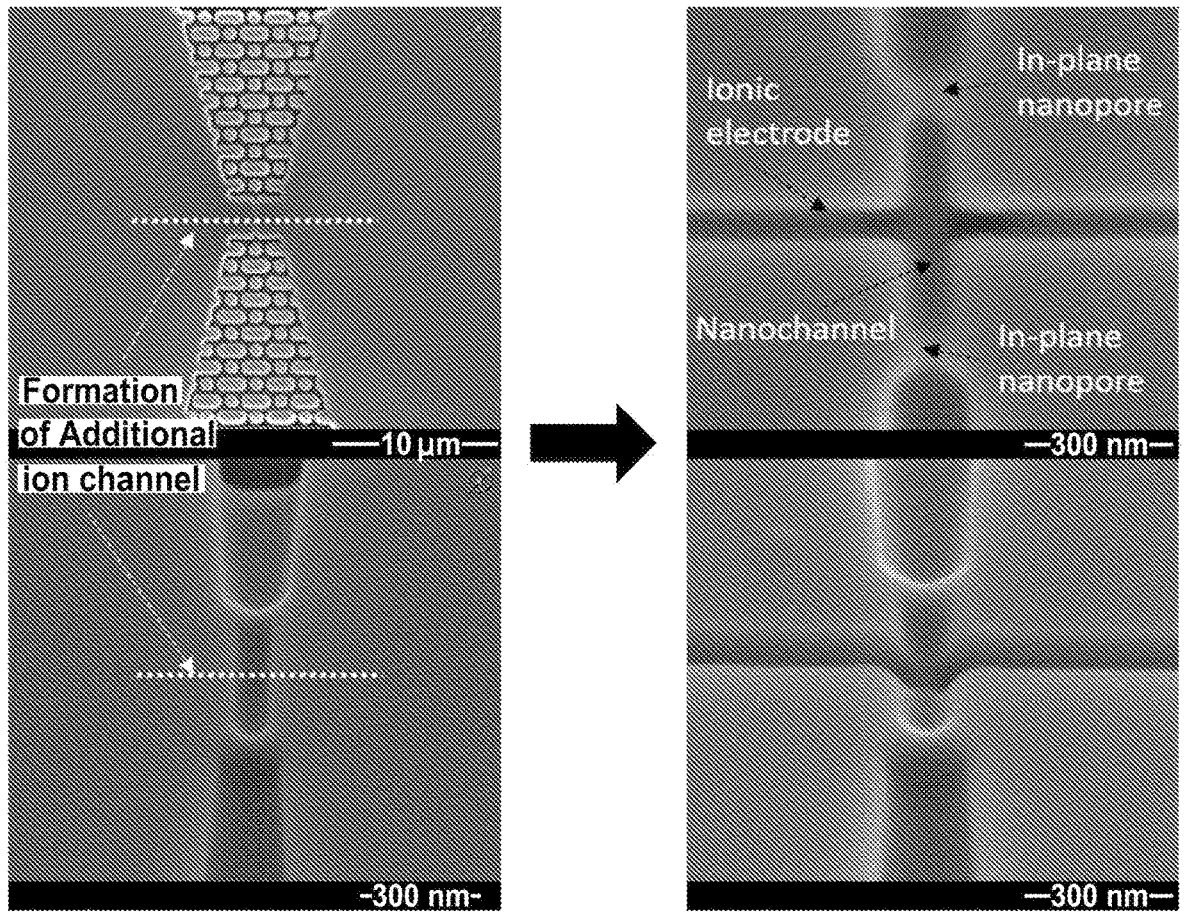
FIG. 9D is scanning electron micrographs for an example nanochannel containing a pair of in-plane nanopores with three electrodes. Two electrodes are positioned at the inlet and outlet microchannels. The third electrode was an ionic electrode consisting of a fluidic channel formed perpendicular to the nanochannel for translocation of molecules to be interrogated.

FIG. 9D shows an example of the three electrode system realized in Si master mold. The two electrodes will be positioned at the inlet and outlet microchannels. The third middle electrode is a nanochannel milled perpendicular to the nanochannel flight tube. The nanochannel is then filled with a conductive electrolyte, which will serve the middle electrode.

Patterning Electrodes

As shown in FIG. 9A, electrodes (3 per sensor) will be patterned on the cover plate of the device to generate the necessary leads to funnel signals to the measurement electronics. These electrodes can be patterned using standard optical lithography and thin film processing techniques. However, there are certain nuances to consider including the fact that the cover plate is assembled via thermal processing to the fluidic substrate. The dimensions of the middle electrical lead (see FIG. 9A) is important for device performance. Because the middle electrode operates at a fixed voltage, it generates an electric field-free region where the molecules can drift via diffusion in the absence of an electroosmotic flow. This drift can be minimized by employing an electrode with a small diameter (e.g., less than 1 µm, such that the diameter is less than 1% of the distance between the nanopores, which in this case is on the order of 100 µm).

To add flexibility in the placement of electrodes, magnetic nanowires have been fabricated by template-assisted electrodeposition. Coating them with gold, via a chemical displacement reaction, will render them corrosion resistant and maintain their magnetic behavior for placement. Fe—Ni—Co nanowire cores can be used here, and the magnetic properties and coefficient of thermal expansion can be tailored through changes in composition. These nanowires can be oriented and aligned at desired location within the nanofluidic device.

The use of nanowires as opposed to thin film electrodes can offer certain advantages. For example, the nanowires can be placed at the wafer-level, which does not require a cleanroom. The nanowires also will not delaminate from the plastic surface or crack during thermal steps used during device assembly. In addition, the nanowires can be prepared in bulk using templating techniques (porous $Al_2O_3$) to a variety of dimensions (diameter and length) using a variety of different materials to suit the needs of device design. In addition, the nanowires can exhibit improved electrical conductivity as compared to thin film electrodes.

Device Performance

The sequencing throughput of the devices described in this example is a function of the number of individual sensor units that can be handled by the instrument, the enzymatic clipping rate of the exonuclease, the error rate of the detector, and the particular application. As discussed above, λ-exonuclease can be used for applications in sequencing dsDNAs. Of course, other processive exonucleases can be used. Appropriate exonucleases can be selected for ssDNAs and RNAs. λ-exonuclease can generate dNMPs at a rate of 1,100 per second (~1.0 ms per base) when immobilized onto a solid support. The enzyme shows a processivity of 40 kbp, and thus, the minimum time required to sequence a single 40 kbp DNA molecule would be approximately 36 seconds. This time-frame is contingent on the electrophoresis time of the dNMPs being less than the exonuclease cleavage rate per base, the number of reads required to achieve accurate consensus, as well as the loading time of a new molecule into the individual sensor for sequencing the next fragment.

Electric field strengths of greater than 20,000 V/cm can be used in the nanochannel flight tubes without experiencing deleterious effects resulting in zone variance. With the electrophoretic mobility of the dNMPs in the flight tubes being $5 \times 10^{-4}$ cm$^2$/Vs and if a flight tube of 50 µm in length is used to provide sufficient resolution to generate a calling accuracy >90% based on dNMP time-of-flight (ToF), the travel time of each dNMP through the flight tube is <500 µs, which is less than the average spacing of the mononucleotides as determined from the activity of λ-exonuclease.

Pacific Biosystems has demonstrated that sequencing a given fragment 50-fold allows one to build a consensus sequence with >99.99% accuracy. A modified rolling circle technology can be used to sequence linear tandem copies of the same fragment using the devices described herein. For example, sequencing the same fragment eleven times at 90% accuracy on each single read will provide an overall accuracy of >99.999% provided the errors are random and not sequence-related.

Each device can be loaded with a second fragment during the sequencing run of the first fragment. This second fragment can be "stored" in an entropic trap associated with each device. Simply changing the electric field strength will thread the second DNA molecule through the immobilized enzyme. The sequencing run can then commence once the cofactor is added.

The number of sequencing runs that can be performed using a single device described herein is a function of the number of λ-exonuclease enzymes that can be loaded onto the nanopillar. Only a single enzyme molecule is used for each sequencing cycle. Assuming a loading density of λ-exonuclease of $1 \times 10^{12}$ mol cm$^{-2}$ on the available surface area of a single pillar (e.g., a 500 nm diameter pillar 50 nm in height), a device can include 450 individual λ-exonuclease molecules.

If desired, multiple devices can be fabricated within a single substrate wafer (also referred to as a chip). The number of devices that can be fabricated on a single chip can depend on the footprint occupied by each device as well as the patterning size that can be accommodated, which is determined by the wafer size that can be processed by the NIL machine (In this case 6"). However, if other methods such as roll imprinting are utilized, this number can increase dramatically. The footprint of each device is approximately 500,000 µm$^2$ (0.005 cm$^2$; 500×1,000 µm; including loading and access channels and the nanochannel flight tube) and thus, approximately 36,400 sensors will fit onto a single 6" wafer (the effective size for the sensors is 135 mm×135 mm, or about 5.3" square).

The devices described herein do not need to be interfaced with optical instrumentation to read the data emanating from the device. Therefore, multiple wafers can be stacked occupying a small footprint (for example, the chip thickness in this example was 2.5 mm and therefore, the footprint occupied by 10 chips would be 15.2×15.2×25 cm$^3$; all of the electrical connections can be configured along one side of the chip stack and inserted into a slot to make the appropriate connections to the measuring electronics; an additional advantage is that each chip can fit into a single slot and thus a modular format where each sequencing run could be configured with the operator's desired chip number to accommodate the necessary sequencing capacity for a single run). Thus, as long as the electronic circuitry capacity is resident within the instrument, multiple chips can be processed simultaneously by a single instrument without affecting footprint. If it is assumed that a single instrument is capable of accommodating 10 chips (6" wafers), then the total number of devices that can be handled by the instrument would be 364,000. Of course, instruments can in principle be fabricated to accommodate a larger number of chips.

The sequencing throughput can be calculated from the total number of devices resident in the instrument and the clipping rate of the λ-exonuclease. With this information in hand, a raw data production rate of $3.64 \times 10^8$ bp s$^{-1}$ can be predicted. If two example applications are contemplated, the approximate throughput can be assessed. In the first example, assume the aim is to obtain complete genome sequence of either germline DNA, tumor DNA from a biopsy, or tumor DNA from purified circulating tumor cells.

The current standard for genome sequencing is 30-fold coverage, or approximately 100 GB of raw data. For the purposes of this example, it is assumed that gentle fragmentation of DNA will produce fragments of ~40 kbp and further, the λ-exonuclease will process each fragment to its entirety with an accuracy of 90%. For germline DNA, each chromosome should have about 15-fold coverage, and thus most SNPs, indels, and copy variations should be identified. By requiring that a given mutation or SNP appear in at least 4 raw sequencing runs with at least 8-fold coverage, the consensus accuracy would be >99.3%. If the single-pass sequencing read were to improve to 95% accuracy, the consensus accuracy would be >99.96% assuming that errors would be randomly distributed. With an average of 40 kb sequence per read, this would establish phase of multiple SNPs across the locus and thus improve overall call accuracy.

In the second example, assume the aim is to perform targeted cancer sequencing directly from blood using circulating cell free DNA as a source of material for the analysis. The aim would be to cover 200 kb@10,000 deep=2 GB of read-length with at least 15-fold coverage from circle-sequencing of 5 kb per each 160 bp cfDNA fragment. Under these conditions, the consensus sequence accuracy is higher, because the same 160 bp fragment has been replicated at least 15 times during a rolling circle amplification. This becomes important in identifying low-level mutations in the plasma at a frequency of 2-3 per 10,000 genome equivalents. A summary of this data is provided in Table 1 below.

While these examples have focused predominately on DNA sequencing, the devices described in this example can be readily programmed to elucidate the structure of other biopolymers, such as RNAs. For example, XRN-1 is a RNA exonuclease and can release ribonucleotides in the 5' →3' direction from single-stranded RNAs. As another example, RNaseII can be used for sequencing ssRNA in the 3'→5'. For proteins, various proteases, such as trypsin, can be immobilized to generate peptides from single protein molecules. The devices described herein can be used for peptide mass fingerprinting of single protein molecules.

TABLE 1

Summary of sequencing metrics for the devices described herein.

|  | GENOME (30-fold) 364,000 sensors (40 kb fragments) | Cancer Genes from cfDNA 364,000 sensors (10,000 genome equivalents) |
|---|---|---|
| Total Output | 1,456 GB | 41.2 GB |
| Run time | 1 h | 1 h |
| Time/fragment | 36 s | 5 s |
| Fragment length | 40 kb (x 8-fold coverage) | 160 bp (x 15 replicates) |
| Single pass accuracy | 90% | 90% |
| Consensus | >99.3% | >99.999% |
| # reads/sensor | 100 | 720 |
| Kb/sensor | 4,000 | 115.2 |
| Genome @ 30-fold coverage | 14.5 |  |
| Cancer genes: 200 kb @ 10K-fold |  | 20 samples/cancer genes from cfDNA in blood |

These numbers compare favorably with current instrumentation when 10 chips are used per instrument run. However, because there is no fluorescence or optical readout required, these projected reads can be achieved at a fraction of the cost compared to current instrumentation. Further, when directly sequencing genomic DNA, there is an opportunity to also score for methylated CpG sites. Because locations of CpG sites in the human genome promoter sequence is known, identification of methylated regions should be achievable. As a final note to throughput, improvements in electronic packaging and speed (for example using field programmable gate arrays to reduce electronic footprint and processing speed) of the measuring circuitry, the instrument capacity for simultaneously processing multiple chips is reasonable. Therefore, the above calculations are conservative estimates.

Importantly, the modular nature of the fluidic chip architecture will allow the devices described herein to perform sample pre-processing prior to the sequencing. For example, we can add to the sample processing region (or to the chip as a whole) sample processing elements for isolating circulating tumor cells (CTCs), cell free DNA (cfDNA) or both directly from whole blood, sample processing elements to perform a solid-phase extraction and/or enrichment of DNA (genomic or cfDNA or both) and/or RNA, fragment the DNA to ~40 kbp lengths, and feed the DNA fragments into the bioreactor chamber for sequence analysis. Thus, the devices and systems described herein can automate the entire sample-processing pipeline, an attractive format for clinical sequencing of both DNA and RNA.

Single-Molecule Processing of Single-Stranded (ss)DNAs using Exo I. Exo I can be immobilized to a pillar configured in a solid-phase reactor to process ssDNA molecules in the 3'→5' direction to generate single dNMPs. The use of Exo I and its ability to process ssDNA can provide for new functionality, such as single-molecule sequencing using X-TOF not accommodated by λ-Exo.

Exo I is a processive enzyme that uses a Mg' cofactor and cleaves ssDNAs into single dNMPs. As with most ssDNA exonucleases, Exo I maintains processivity by holding ssDNA in an electropositive cleft that is too narrow (<2 nm) to accommodate dsDNA. The cleft can electrostatically bind to ssDNA even when the active site is inactive (no $Mg^{2+}$), but cannot maintain processivity through secondary structures, which do not fit within the binding cleft. As such, in vivo Exo I is complexed with a SSB protein (SSB; $K_d$=10$^-$7M). SSB is a tetrameric protein that binds both ssDNA and Exo I, sliding along the ssDNA substrate and unwinding secondary structures to maintain Exo I processivity, as well as enhance clipping rates. In solution, SSB-Exo I can clip ssDNA at ~120 nucleotides/s and has a processivity ≥625 nucleotides.

Figure 27:
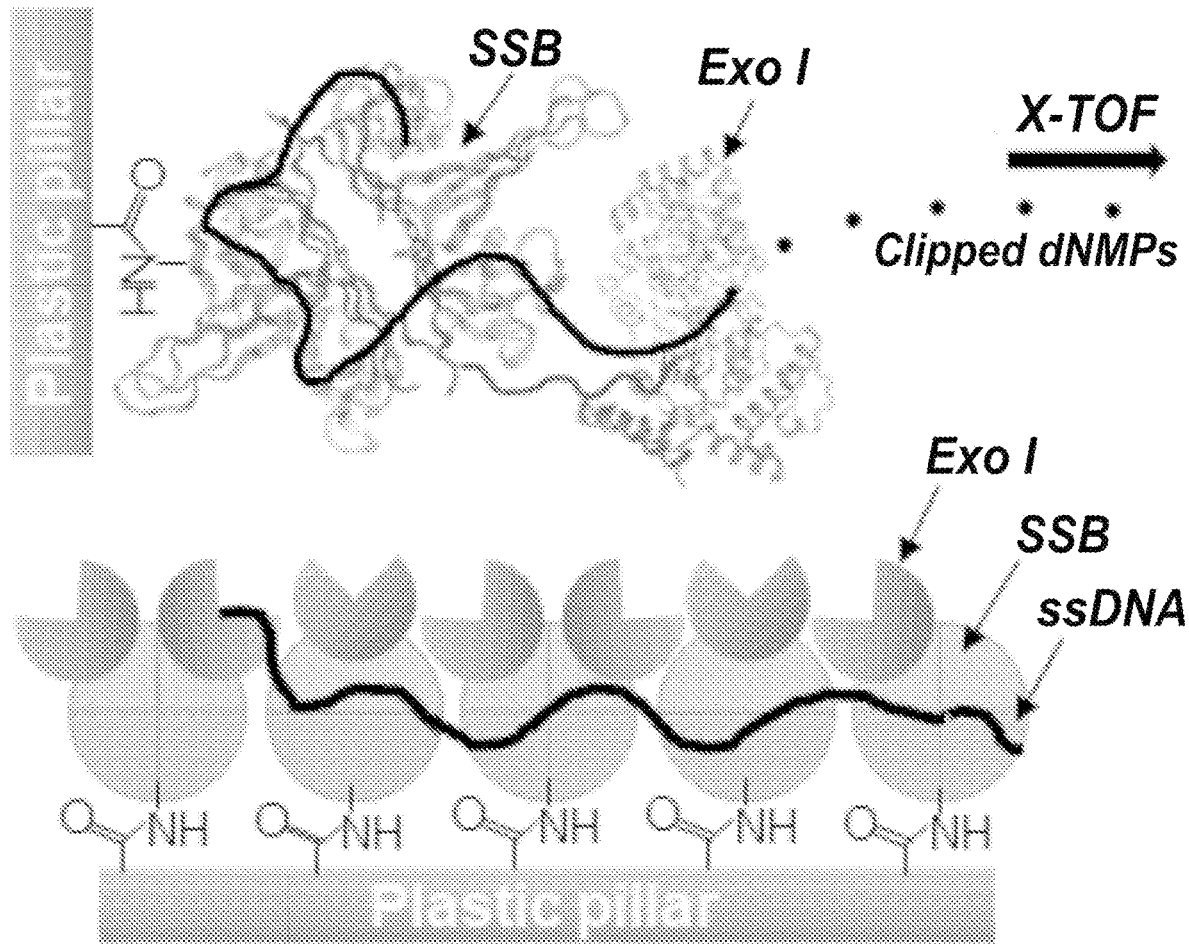
FIG. 27 is a schematic illustration showing the covalent immobilization of single-strand binding protein (SSB) to a UV/O3-irradiated plastic support followed by assembly with Exo I (ribbon structures). The SSB can bind up to 65 nt of ssDNA and 4 Exo I enzymes. Nano-electrophoresis can be used to interrogate reaction products (dNMPs) generated by the Exo I cleavage reaction.

For the solid-phase reactor using Exo I, SSB can be covalently linked to a reaction pillar that has been UV/$O_3$ or $O_2$ plasma activated with EDC/NHS coupling chemistry as described above with respect to XRN-1. Then, Exo I can self-assemble onto the surface through the immobilized SSB (FIG. 27). Because both SSB and Exo I can bind ssDNA, this strategy properly orients the Exo I active site towards solution.

Effect of Nanopore Length on Device Performance

Figure 10:
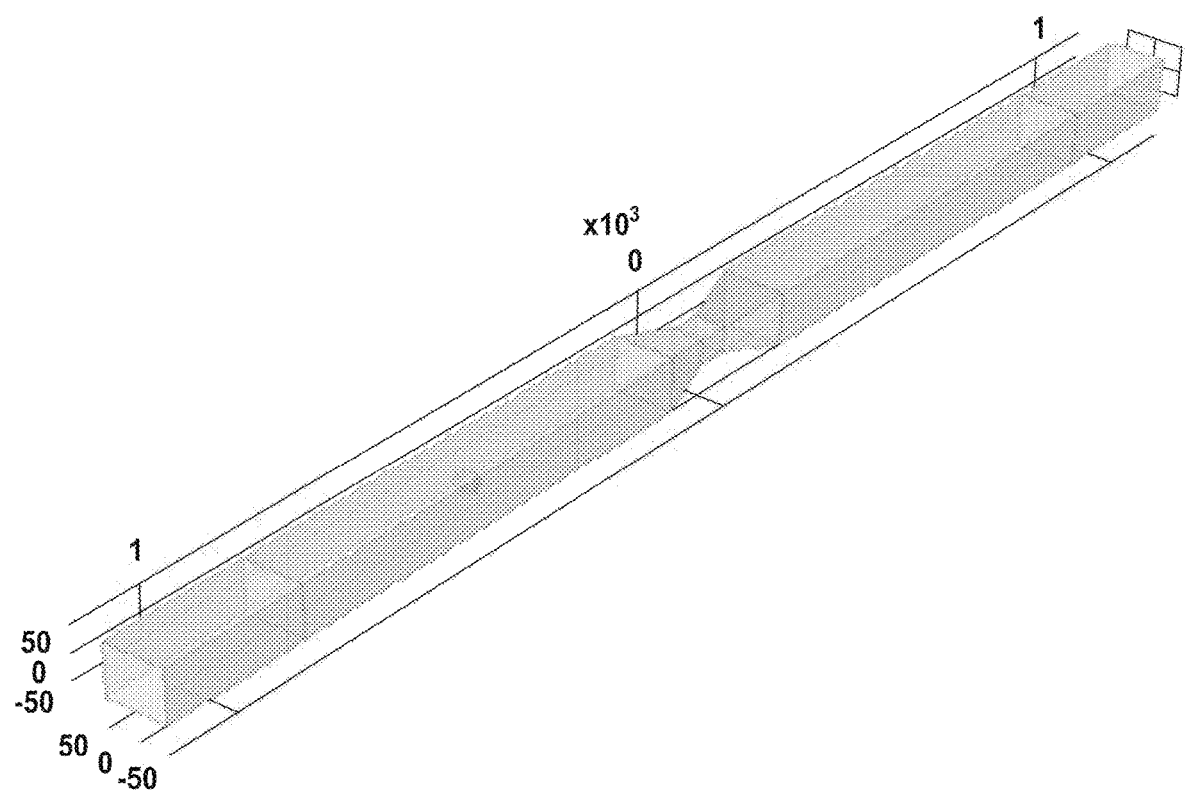
FIG. 10 shows a simulated nanochannel and a nanopore that was used to evaluate the effect of nanopore length on the current transient signal.

The length of the nanopores can also be tailored and tuned to impart differences in the time duration of the current transient signal invoked by single molecules to help differentiate between responses generated at the first nanopore from those at the second nanopore. A simulation was utilized to study this effect with only a nanochannel and a nanopore centered within it. This model was tested using AutoCAD 2014 and then imported into COMSOL 4.3; it can be seen in FIG. 10.

Figure 11A:
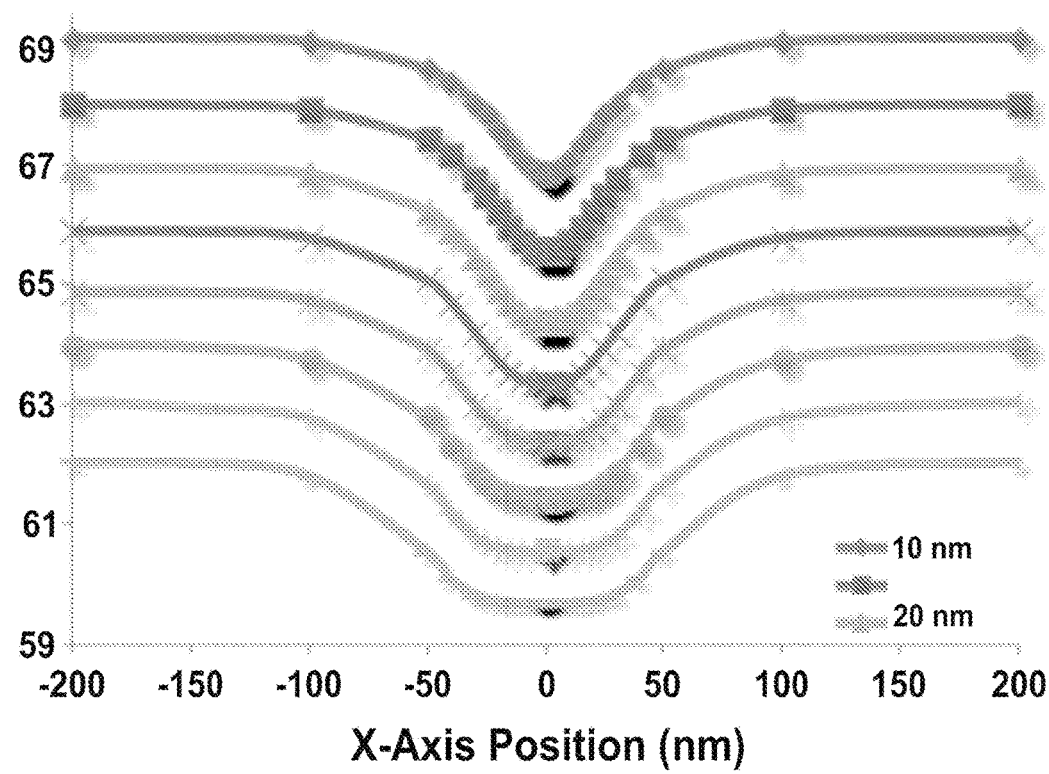
FIG. 11A is a plot illustrating the calculated current drop during passage of a spheroid representing a single molecule through nanopores having lengths ranging from 10 nm (top trace) to 80 nm (bottom trace).

FIG. 11A is a plot illustrating the calculated current drop during passage of a spheroid representing a single molecule through nanopores having lengths ranging from 10 nm (top trace) to 80 nm (bottom trace). For these experiments, the other channel and pore dimensions as well as the radius of the molecule (2 nm) were held constant, along with the buffer concentration (2.5×TBE) and driving potential (10 V).

The current observed when the single molecule, modeled as a spheroid, is located in the first part of the nanochannel upstream of the pore is visible on the far left of the plot. As the molecule is "stepped" through the nanochannel and nanopore, current measurements were calculated at 45 distinct points. The current drop increased as the pore length approached the molecule diameter. Additionally, an increase in the length of the pore increased the duration of the current signal.

Figure 11B:
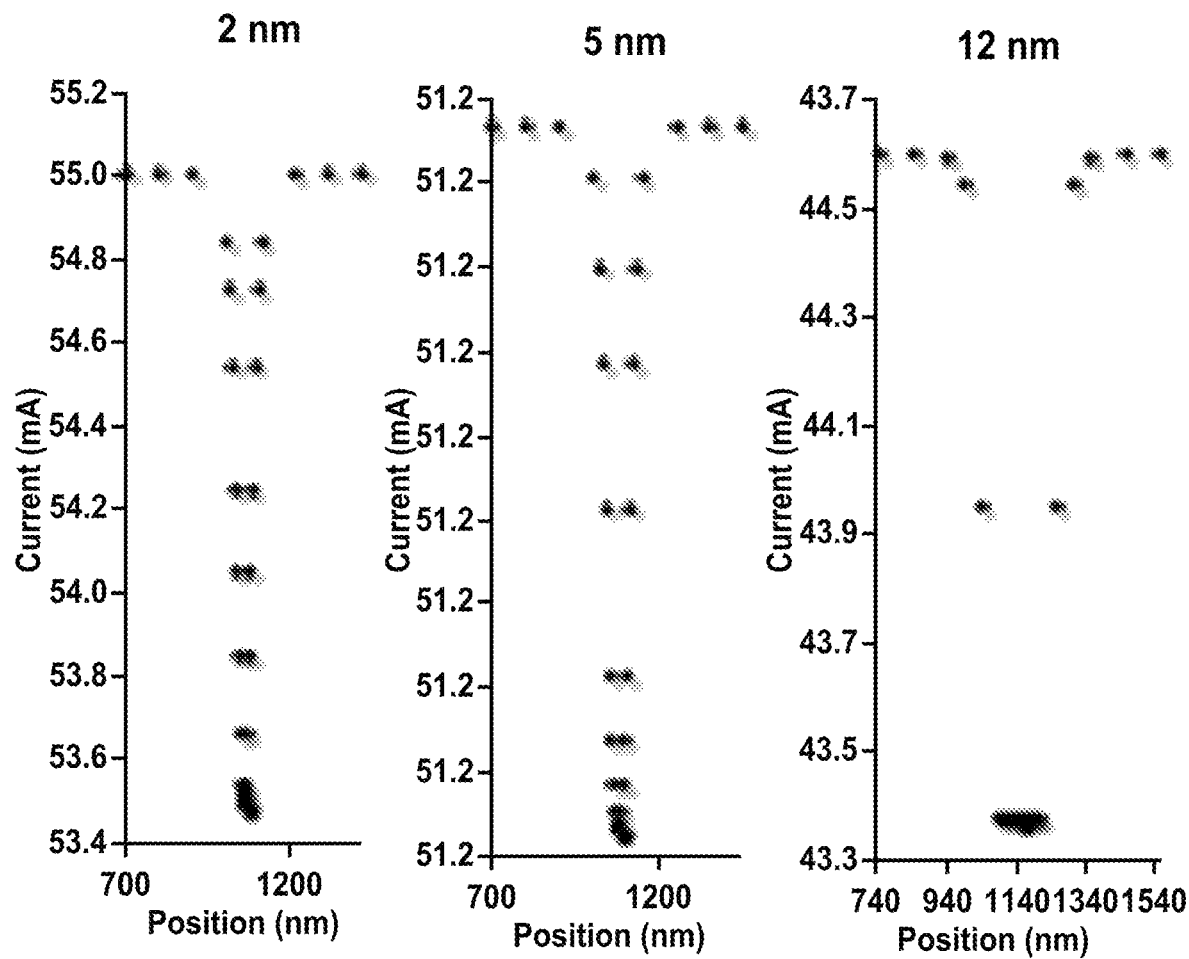
FIG. 11B is a plot illustrating the calculated current drop during passage of a spheroid representing a single molecule through nanopores having lengths of 2 nm, 5 nm, and 12 nm.

Further modeling was performed to better understand the relationship between the pore length and the shape of the signal output from the sensor. The same geometry was used in this second analysis but with a finer mesh, especially around the curvature of the molecular sphere. The results are shown in FIG. 11B. Again, it was demonstrated that the lengths closest to the diameter of the molecule showed the largest current drop, with diminishing signals as the pore length got much larger or smaller (the 2 nm pore recorded a current change of 1.52 nA, the 5 nm pore recorded 1.67 nA, and the 12 nm pore recorded 1.23 nA).

The difference in the width of the signal was also seen more clearly, further elucidating the idea that the sensor geometry could be modified to match the hardware that is performing the current measurements. For systems where the sampling frequency limit is being approached, a longer pore could allow for more molecules to be correctly detected. Conversely, for systems where the dynamic range is the limiting variable, a shorter pore, closer to the diameter of the particle, could be used to ensure that the signal has the highest amplitude possible.

Example 2: Large Area Mold Fabrication and CIM of Mixed-Scale Structures in Thermoplastics Use of high throughput ICM to fabricate nanofluidic structures has been impeded by several factors: (1) Fabrication of high quality, large area molds with nanofluidic structures. Basic requirements for mixed-scale molds include high shape repeatability to help manufacturing quality control, long molding tool lifetime to reduce the frequency of tool change over and production interruption, low friction, minimal chemical interaction, low thermal expansion to facilitate demolding, and low cost and high speed molding tool fabrication. (2) Molding of multi-scale features in large areas, which can cause inhomogeneous filling and stress behavior at different locations of the molded structures. This could result in molding failure due to locally incomplete filling, undesirable deformation, and partial/total ripping of molded materials. (3) Demolding failure due to severe warping and/or local substrate bending, making it difficult to generate a tight seal between the fluidic substrate and cover plate. Such issues can be addressed through proper design of the mold insert structures in combination with the use of the engineered materials for mold inserts. An example includes addition of auxiliary structures in appropriate locations to enhance filling and to avoid stress concentration in active structures. (4) Location-dependent dimensional variation of molded structures. This location-dependent dimensional variation occurs due to the thermal expansion/shrinkage of mold inserts during the molding/cooling process and becomes more significant as the size of mold tools increases. The strategy to overcome this obstacle is the use of materials with tailored coefficient of thermal expansion (CTE), such as Super Invar-like composite for electroplating to produce molding tools.

Design and Fabrication of Large Area Molds for ICM

Figure 12:
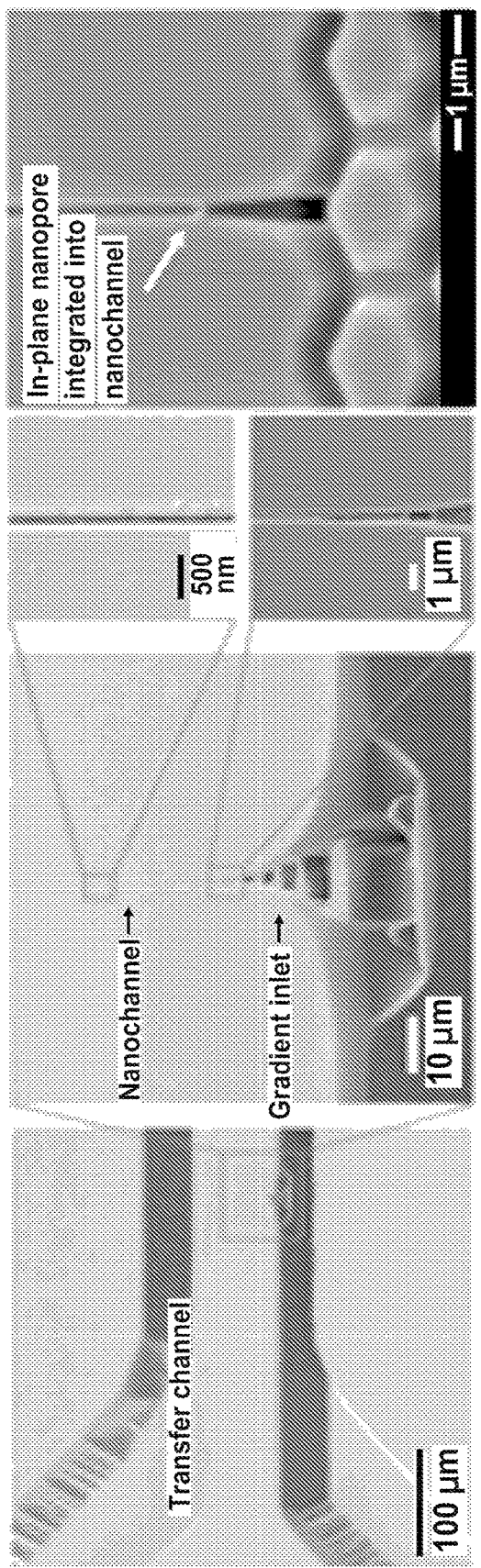
FIG. 12 shows a Si master with nanochannels and in-plane nanopore fabricated by FIB milling.

Si mold master fabrication. For the fabrication of a master mold in Si with mixed-scale nanofluidic structures, high-end nanofabrication tools can be hierarchically combined with micromachining techniques. The micro- to macro-scale fluidic network can be prepared via photolithography, followed by pattern transfer into Si through etching. The KOH wet etching of Si usually produces tapered structures with low surface roughness, as compared to rough, almost vertical sidewall profiles generated by reactive ion etching. In some cases, the tapered structure can be used for the fluidic network because it can help guide the introduction of molecular targets into the nanochannels. The nanochannels can be directly written using a $Ga^+$ FIB into the Si substrate. As shown in FIG. 12, nanochannels with the width of ~50 nm and in-plane nanopores with sub-10 nm depths integrated into the nanochannel can be readily prepared.

Because the maximum sample size to mill with our FIB system is limited to ~2"×2", a 6" Si master was produced with a single sensor structure generated as described previously and large area molds were then produced via a step-and-repeat process. In this way, location-dependent variations in the sensor structures due to de-focusing of ion beams can be minimized. Large area molds can be generated so that in a single ICM cycle, multiple devices can be generated reducing device cost and increasing the production rate. In addition, multiple devices on a single wafer can improve device throughput in terms of sample processing—high throughput analysis.

Electrodeposition of composites with tailored CTE. From the Si mold master, an ICM molding tool can be generated via electrodeposition of the appropriate material. As a plating base, a thin, seed layer of Ti (~5 nm) and Au (10 nm) can be deposited onto the Si structures, which can be followed by electrodeposition of CTE-tailored deposits. In order to minimize the location-dependent dimensional variation occurring during the molding/cooling process, materials with tailored CTE, such as Super Invar-like alloys can be used for electroplating to produce the ICM molding tools. Another advantage of using Super Invar-like composite materials is their high Young's modulus, which is attractive to increase the durability of the molding tool. These methods can be used to create robust Super Invar-like mixed-scale molding tools (nm→mm) to be used with ICM.

While most electrodeposited metals and alloys exhibit high CTE, few have low ones, and most methodologies established for plating do not take into account multi-scale features, which can generate a distribution of the actual deposition driving force, locally. These methods can utilize a CTE-tailored Super Invar-like alloy electrodeposited into recesses fabricated via lithography. The Super Invar-like composition, 64 wt % Fe, 31 wt % Ni, and 5 wt % Co, is realized in recesses by using different pulsing waveforms and the composition distribution along the length of the recesses confirmed the control of local composition, and a low corresponding CTE. The presence of micro-cracks were evident when the measured CTE was negative, i.e. the raised structures shrink with a temperature increase. A challenge to be addressed is that the layer defined by the plating base can be non-uniform and make it difficult to control the composition and properties in the recesses. A distribution analysis can be used to design the plating cell configuration to "jig" the anode, cathode and insulator arrangement for changes in substrate topography.

Electrodeposition and pulse electrodeposition can be used as an effective means to create high aspect ratio deposits. Materials can be added into Fe—Ni—Co alloys that exhibit negative CTE, to better tailor the overall composite CTE, incorporating the AWN family of ceramics, such as zirconium tungstate oxides and those with the addition of molybdenum as nanoparticles into the metal alloy matrix, to form composites. These materials can exhibit large isotropic negative thermal expansion over a wide temperature range. Ceramics are inherently brittle, thus including them as a composite in a metal matrix, provides a means to reduce the brittleness and take advantage of the metal properties, such as elasticity, hardness, and ductility.

Figure 13:
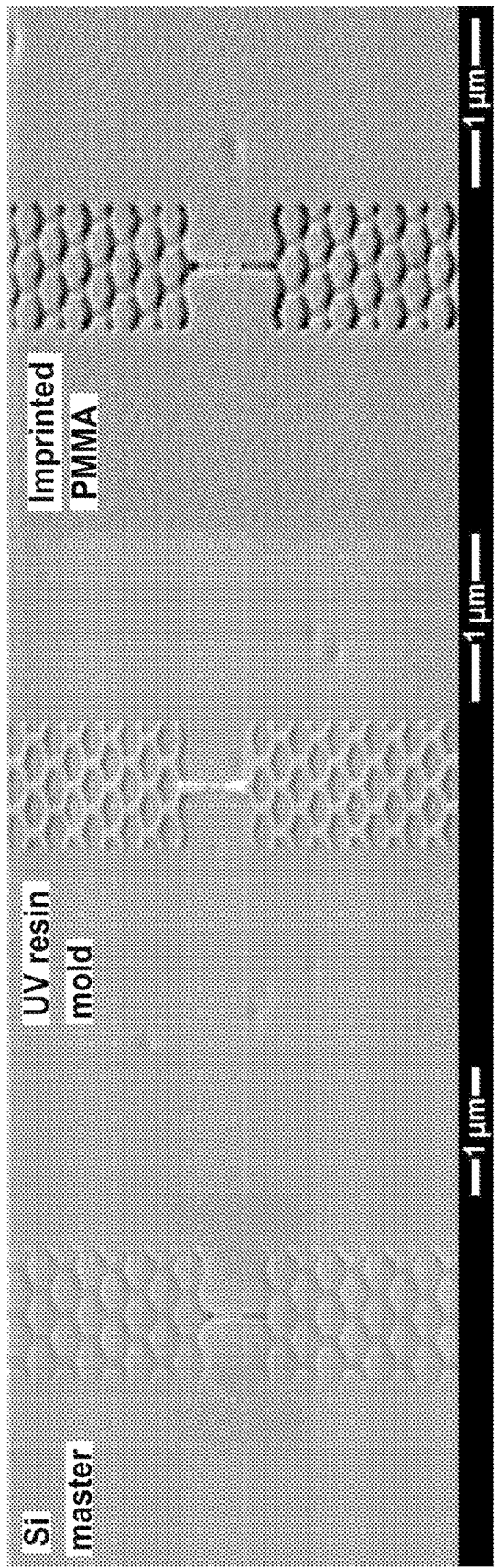
FIG. 13 shows SEM images of a nanochannel in (left) Si master, (middle) UV curable polymer stamp replicated from Si master, and (right) imprinted PMMA with the polymer stamp.

Alternative molding tools. Adhesion force is related to both surface energy and Young's modulus. However, most efforts to improve demolding have focused on reducing surface energy of molding tools. While the range of varying the surface energy by either material selection or surface modification is limited to at most an order of magnitude, one can vary Young's modulus by orders of magnitude via appropriate material selection. An imprint stamp made of a UV curable polymer (resin stamp) can be used to directly nanoimprint the nanosensor structures into a PMMA substrate. In this way, even sub-10 nm in-plane nanopores were faithfully replicated (FIG. 13). However, use of a simple resin stamp as molding tools for ICM can experience a loss of tool shape during molding and consequently lead to poor replication fidelity. The lifetime of the molding tool is another issue. Therefore, an alternative strategy of using electroplated metal molding tools is the use of organic-inorganic composite resist materials to produce molding tools from the Si master mold. Commercially available organic-inorganic composite resist materials include hydrogen silsesquioxane (HSQ) and polysilazane. The compositions of the resist components can be varied to modify the Young's moduli of these resists. The goal is to find a composition which reduces adhesion sufficiently and at the same time shows high mechanical stability to sustain the ICM conditions.

Multi-scale ICM of Nanofluidic Structures. To understand the underlying mechanisms and to better control large area and multi-scale ICM, experimental and simulation studies of molding and demolding with the CTE-tailored composite or organic-inorganic composite molding tools can be combined.

Figure 14:
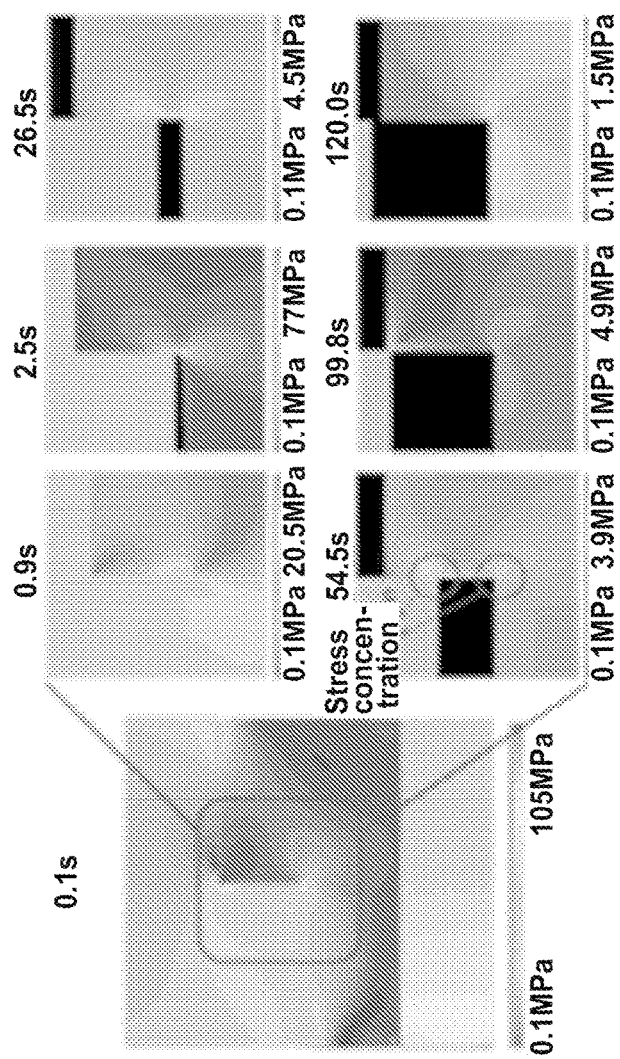
FIG. 14 shows Von Mises stress evolution in PMMA resist during normal demolding for single symmetric structure.

An example result is shown in FIG. 14, where the demolding process of thermal NIL was simulated for a standard setup of Si stamp/resist/Si substrate. The force required for demolding and the local highest stress was determined as a function of demolding temperature, demolding rate, friction coefficient, and location of structures under vertical displacement of stamps with respect to the substrate surface. The effect of shrinkage and adhesion on the resultant demolding force was also evaluated. The results show that contribution of shrinkage stress to demolding force is as significant as that of adhesion, which indicates that efforts to reduce shrinkage stress needs to be combined in addition to the effort to reduce surface energy in order to improve the demolding process.

Modeling of molding/demolding processes for large area, multi-scale CIM can be pursued using finite element analysis, ANSYS. The main focus of the molding simulation will be to investigate the filling of polymers into hard stamp cavities of various geometries and locations, with the ultimate goal of achieving a high yield process with good replication fidelity at low-cost and fast optimization of parameters such as temperature, pressure, and molding time. On the other hand, through the demolding simulation, the local and overall stress changes and the resulting undesirable deformation in the molded polymer substrate can be determined. The viscoelastic-plastic model will be used for thermoplastics used as the substrate. The simulation method can be expanded for molds that contain multi-scale structures in large area. Various stamp designs can be simulated under different process conditions. The systematic study on the demolding force under various conditions can be used to determine governing rules leading to the success of molding with regard to the parameters involved.

A three-dimensional (3-D) map showing the demolding forces as a function of structured surface areas, surface energies and effective Young's modulus of mold inserts for a certain resist or the demolding forces as a function of the pressure, time, and demolding temperature can be generated. There will be an abruption in the 3D curves, which represents occurrence of failure in the molded structure. Once such maps are established, they can be useful in designing and optimizing structures and processes that are "patternable" via ICM.

With the CTE-tailored composite molds or organic-inorganic composite molds, ICM can be performed using the commercial ICM machines. Up to 6" mold inserts will be used. Location-dependent replication fidelity and durability of the molds can be assessed by various metrology instruments such as AFM, SEM and profilometer.

Fabrication Methods

Figure 28A:
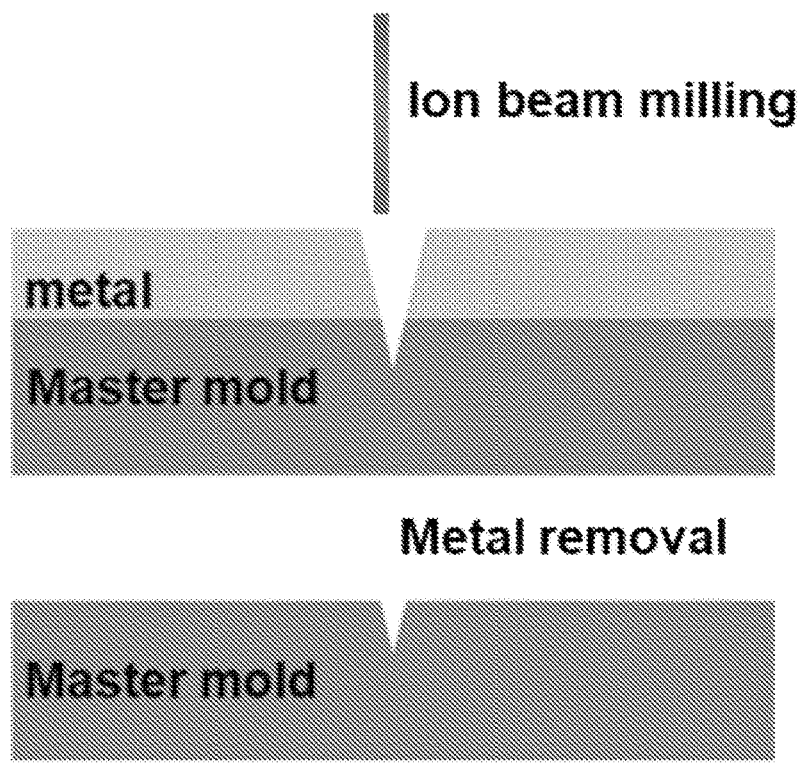
FIG. 28A is a schematic illustration of metal-assisted FIB milling.

Sub-5 nm nanochannels can be fabricated in a quartz substrate via focused ion beam (FIB) milling into a thin metallic sacrificial layer coated on the quartz substrate. The channel was milled through the metal layer until it penetrated a prescribed depth into the underlying substrate. A schematic diagram of metal-assisted FIB milling is shown in FIG. 28A.

Figure 28B:
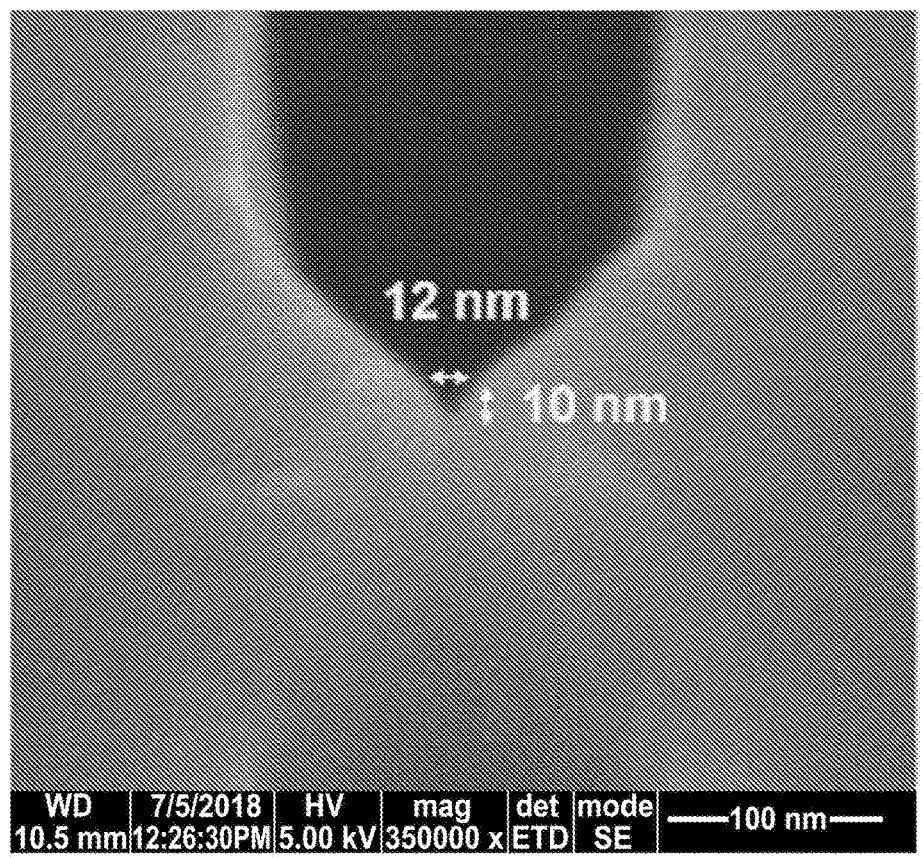
FIG. 28B is an SEM micrograph showing an in-plane nanopore fabricated by metal-assisted FIB milling with a 150 nm thick Al sacrificial layer coated on Si substrate.
Figure 28C:
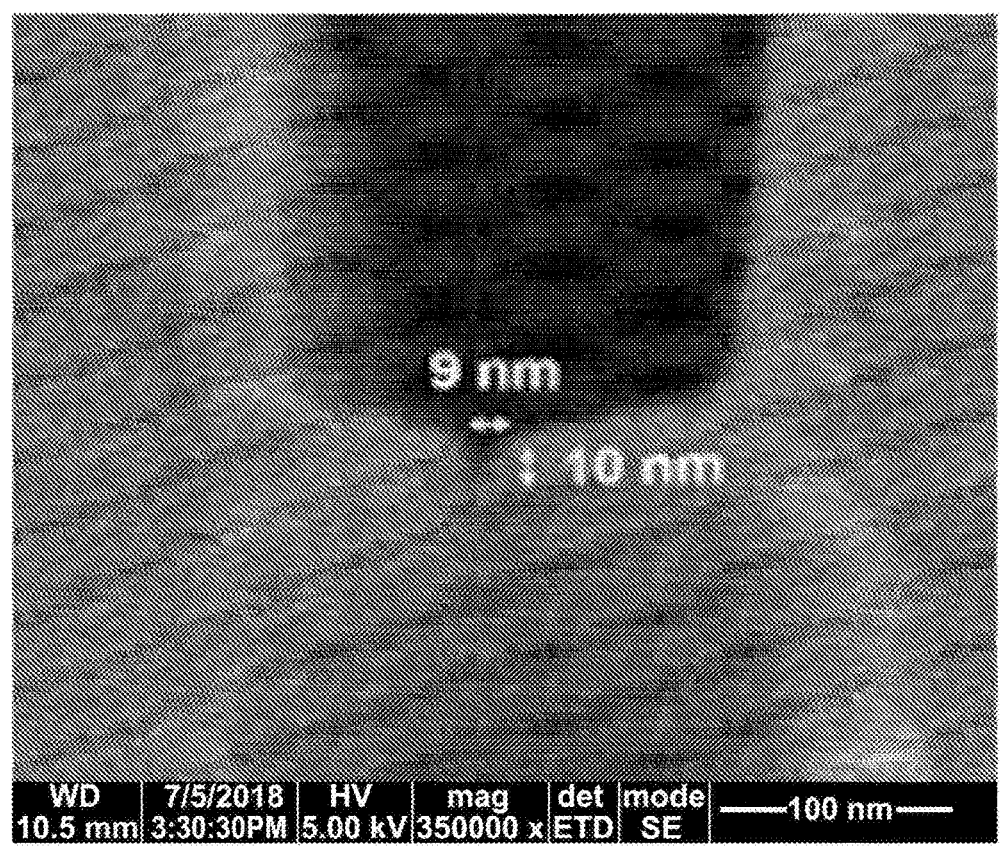
FIG. 28C is an SEM micrograph showing an in-plane nanopore in COC substrate replicated from the Si mold shown in FIG. 28B.

A preliminary test for metal-assisted FIB milling was performed with a 150 nm thick Al layer coated on a Si substrate. FIG. 28B shows a nanopore with a similar width and depth in Si after removal of the sacrificial Al layer. The Si master was replicated into a UV resin and then into a plastic substrate, which was cyclic olefin copolymer (COC) in this case; good replication fidelity was observed as seen In FIG. 28C. Metal-assisted FIB milling process can be used to produce Si masters with the nanochannels including nanopore of different sizes depending on the types of molecules to be interrogated with the sensors.

For thermal NIL, a hard plastic substrate can be used as opposed to PEGDA, which has a low Young's modulus and as such is prone to collapse during assembly of the fluidic device. In particular, COC can be used due to its high replication fidelity using thermal NIL and long-term stability against solvents and electrolytes.

Another issue to consider in the design and fabrication of the in-plane nanopore sensors is that the size of the nanopores is reduced during thermal fusion bonding of a cover plate to the substrate because the bonding process inevitably involves mixing of polymer chains from the molded substrate and cover plate. The bonding layer should be thick enough to result in sufficient bonding strength to operate nanofluidic experiments. However, at the same time, a thick bonding layer will make it difficult to accurately control the final pore size. Therefore, for better control of device feature sizes, especially the in-plane nanopores in bonded nanofluidic devices, Si masters can be fabricated with dimensions similar to or slightly larger than the final device dimensions required. To accomplish this, intensive nanomanufacturing work will be performed to achieve dimensional control over the device feature size during FIB milling, NIL, and cover plate bonding processes. If necessary, a controllable process can be developed to reduce the nanopore size during the thermal fusion bonding process. A thermal fusion bonding system will be built, which will allow monitoring the lateral stretching of the substrate via a strain sensor and monitor the pore size via conductance measurements; conductance changes arise from pore size-dependent ionic current flow through the in-plane pores. The effects of the fabrication process parameters on the nanopore size, the signal-to-noise ratio of current transient signals from single molecules, and standard deviations in the current transient amplitudes for the same molecule will be evaluated.

Example 3: Electronics

Figure 15:
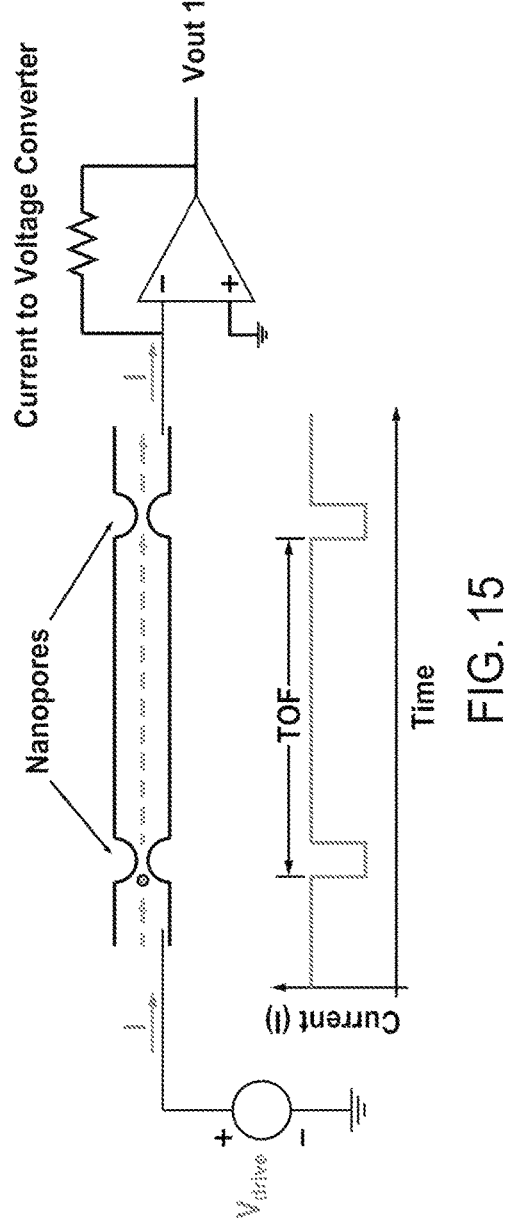
FIG. 15 is a schematic diagram showing the method of electronically detecting pore occlusions and measuring the time of flight (TOF) of particles in the channel. A channel containing an entrance and exit nanopore forms the basic nanosensor. An ionic fluid stream containing particles of interest is presented to the channel and is iontophoretically driven by the DC voltage source, $V_{drive}$. The particles typically have higher electrical resistance than the ionic fluid so that the current decreases as the particles are driven through the entrance and exit pores. This change in current can be measured using standard current-to-voltage converter circuitry.
Figure 16:
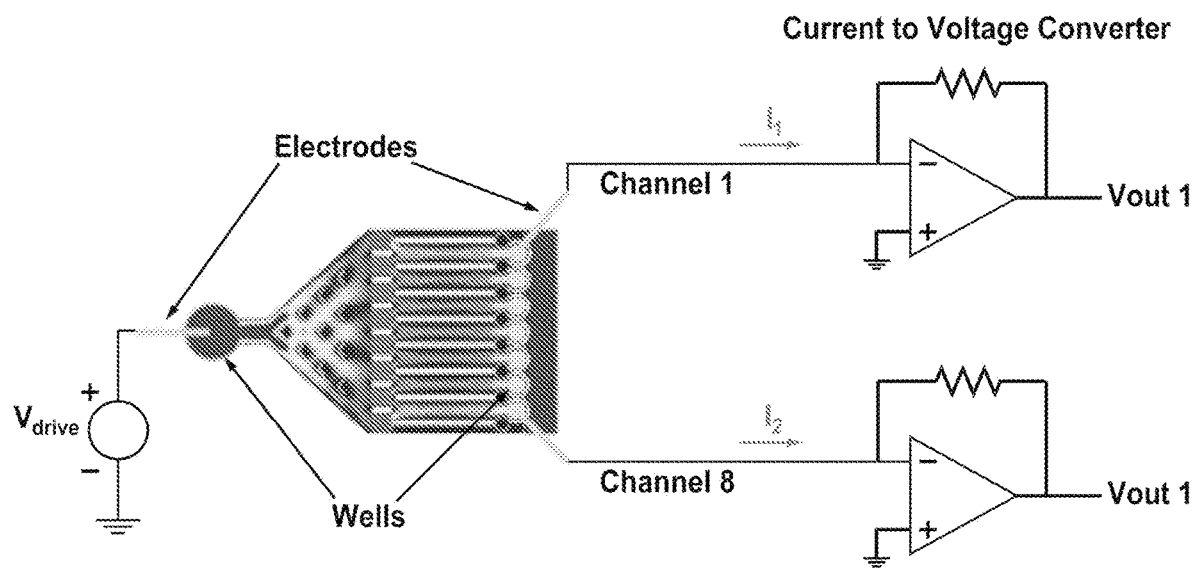
FIG. 16 is a diagram showing the previous current-measuring concept applied to an array of nanopore TOF channels. This example shows an array of channels with a common fluid input well and electrically isolated outlet wells. Electrodes in the wells provide the path for the drive current and the paths for making independent current measurements for each channel.
Figure 17:
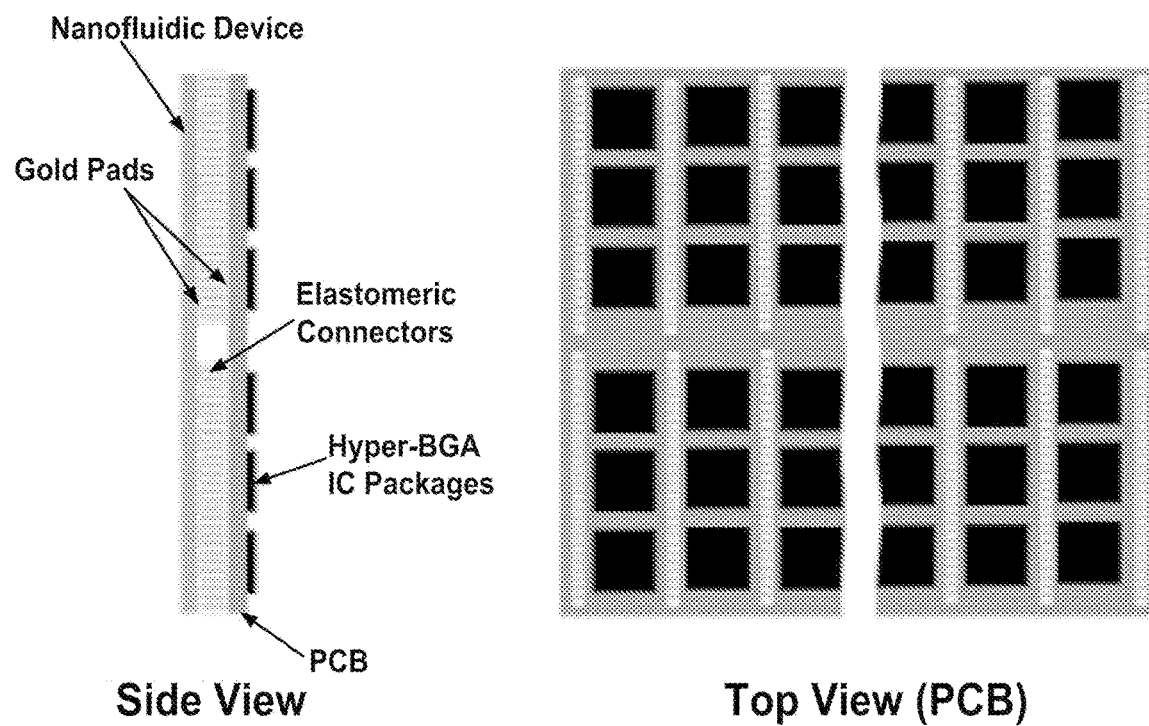
FIG. 17 shows the scaling up the number of electronic channels to accommodate multiple parallel nanochannels. It shows a configuration which allows high-density electrical connections between the nanofluidic device (nanosensor) and a typical printed circuit board (PCB). Gold contacts are plated onto the nanosensor and on the PCB. Elastomeric ("Zebra") connectors are used to make connection between the gold pads. The elastomeric connectors are commercially-available connectors comprising alternating conductive and insulating layers in a compressible elastomer. Gold pads with a width to accept at least two conductive layers in the elastomeric connector are used to ease the alignment of the panels and the connector. The nanosensor and the PCB are then put under compression to make the connection. The nanosensor can be removed and replaced allowing the nanosensor to be a disposable component. HyperBGA or other commercial-style integrated circuit (IC) packages with high connector density can be used to house the electronic circuitry required for the readout of the nanosensors.

There are several methods by which time-of-flight (TOF) and channel conductivity can be measured as particles traverse in-plane nanopores located in a nanochannel. Conducting electrodes must be introduced into the channel that can be connected to electronic circuitry which can be located on the same substrate or on a secondary substrate (i.e., silicon, PCB, etc.). There exist several electrode topologies that are used and each of those can have several electronic circuit topologies that can be associated with them. In addition, the term electrode as used here means any conductive material that can be used to electrically interrogate the nanochannel and its pores. Therefore, the electrodes can consist of materials such as (but not limited to) conductive metals, films, and fluids in any combination. For example, metallic electrodes can make contact to additional nanochannels containing conductive fluids that provide the contact to fluid in the main nanochannel/nanopore path. The electrodes can also provide capacitive contact (AC) to the nanofluidic circuit as well as direct contact (DC). Finally, electrical interconnections between the fluidic device and the electronic circuit must be made (FIG. 15). These interconnections can be relatively simple for low channel counts, but become more complex with increasing parallel channel counts (FIGS. 16 and 17).

Two-Electrode Case

Figure 18:
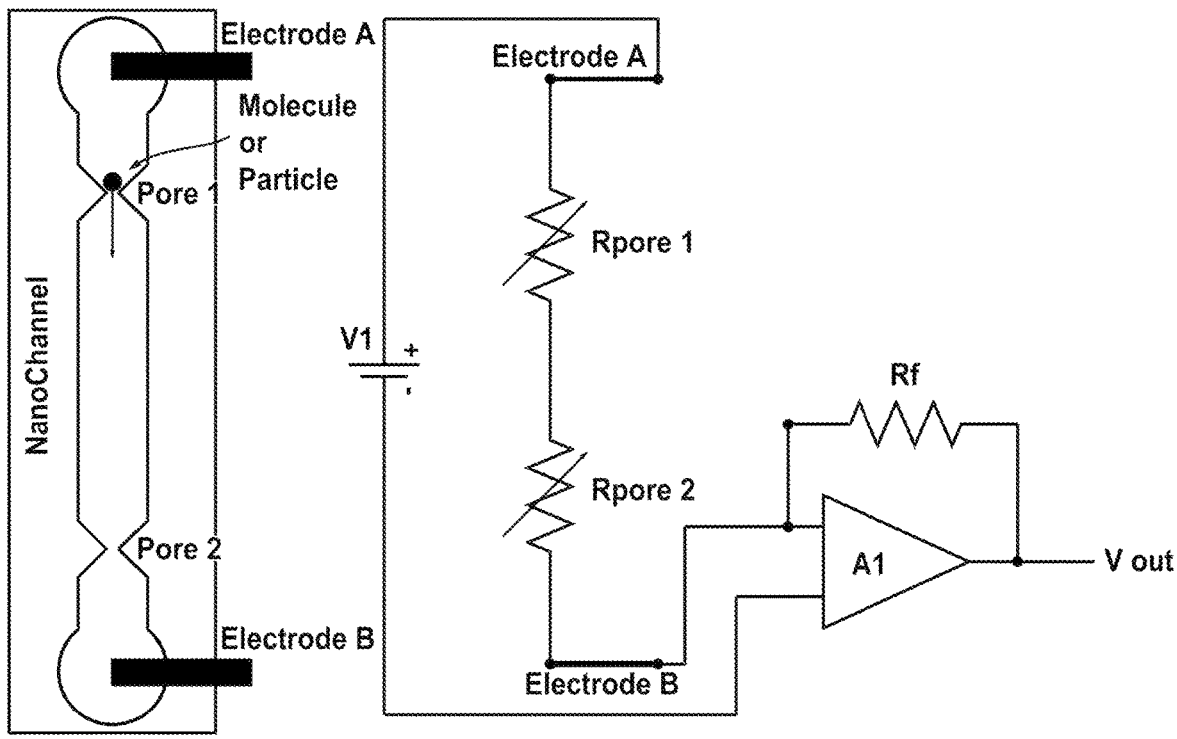
FIG. 18 shows a two-electrode system on the left and an equivalent electrical circuit on the right including a DC coupled Transimpedance Amplifier (TIA) circuit for measuring blockade events. V1 is the voltage source that provides the iontophoretic driving current to move particles through the nanochannel. Rpore 1 and Rpore 2 represent the resistances of the individual pores which vary depending upon the magnitude of the blockage at the respective pores when a particle traverses them. Note that the return path for the iontophoretic current is through the virtual ground of the TIA topology of A1.
Figure 19:
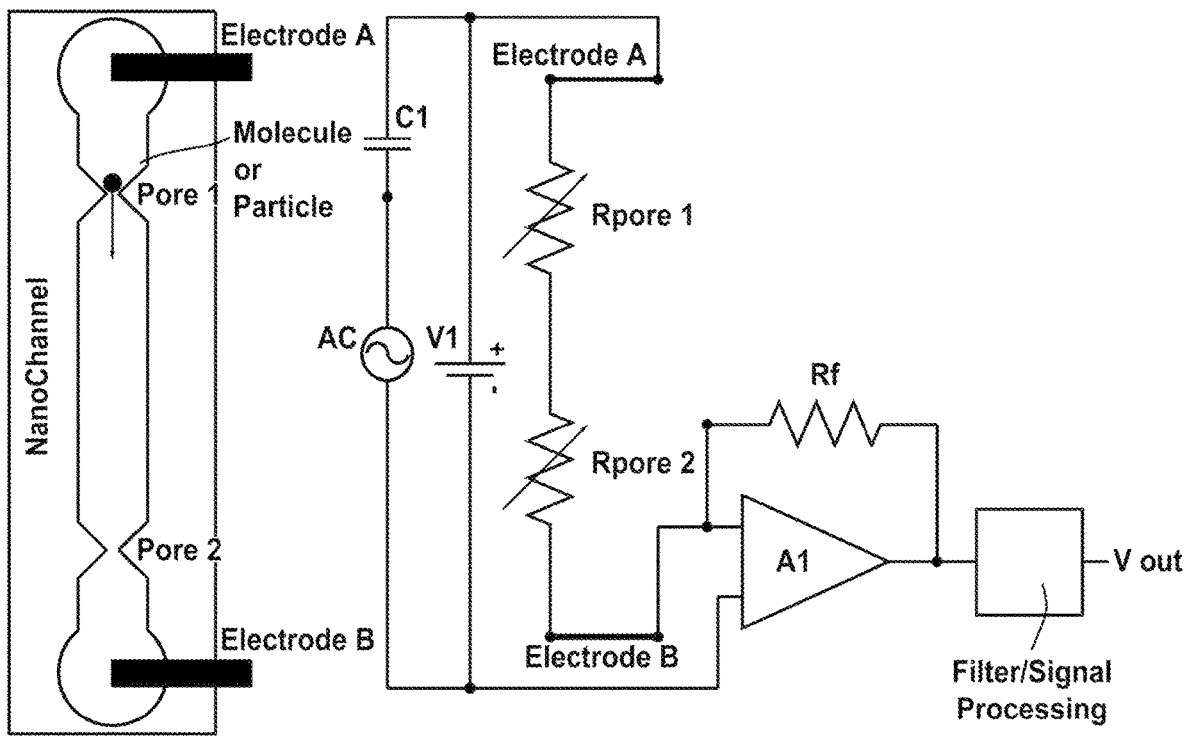
FIG. 19 shows the same two-electrode nanochannel configuration with the same TIA as in FIG. 18, but with the addition of a separate AC signal source. In this case, V1 still provides the iontophoretic drive current, but there is an AC signal superimposed on it that operates at a frequency above the "relaxation" times of the particles travelling in the nanochannel such that they are not physically affected by the presence of the AC signal. Blockade events can now be detected by both changes in the DC iontophoretic drive current and changes in the AC signal. In addition, both phase and amplitude of the AC signal can be measured by signal processing after filtering. This allows higher statistical accuracy because there are now three orthogonal measurements being made simultaneously from single blockade events.

The simplest electrode topology includes two electrodes, one located at the entrance to the first pore and a second located at the exit of the second pore (FIG. 15). These electrodes provide a connection to a power supply that provides the iontophoretic drive that propels particles through the pores and nanochannel. The resulting change in current when a particle occludes a pore (blockade current) indicates the time the particle moves through each pore, thus yielding the TOF. In addition, the amplitude of the change in current can be used to identify the particle size and/or the nature of the particle (i.e., identification of A, C, T, or G in the case of nucleotides passing through the pores). In this case, a current measuring device, such as a transimpedance amplifier (TIA) or other current measuring device can be used to measure this current. If the pore sizes are identical, then the pairs of blockade events must be identified and associated with a specific particle. The pore sizes can be different, resulting in a known difference in the blockade current when a particle enters each pore, enabling easier particle identification and computation of TOF. The circuit can be either DC or AC coupled since the blockade events result in transient current changes (FIGS. 18 and 19).

Three-Electrode Case

Figure 20:
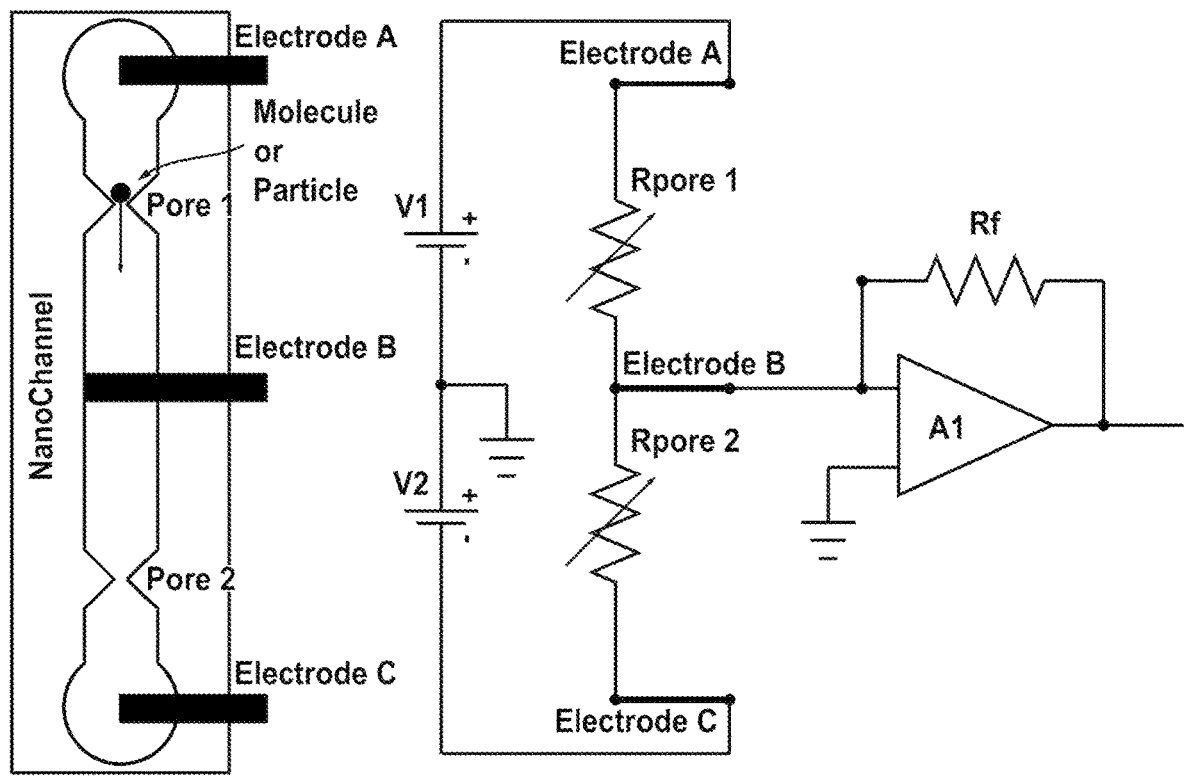
FIG. 20 shows a three-electrode configuration for the nanochannel along with a DC-coupled TIA to measure the change in current. It utilizes two separate voltage sources to control the iontophoretic drive across each individual pore referenced to a centralized electrode. An extension of this would be to have an additional pair of AC sources or a center-tapped transformer-coupled AC source superimposed across the DC drive sources. The AC techniques described in FIG. 19 can then be applied to this three-electrode method.
Figure 21:
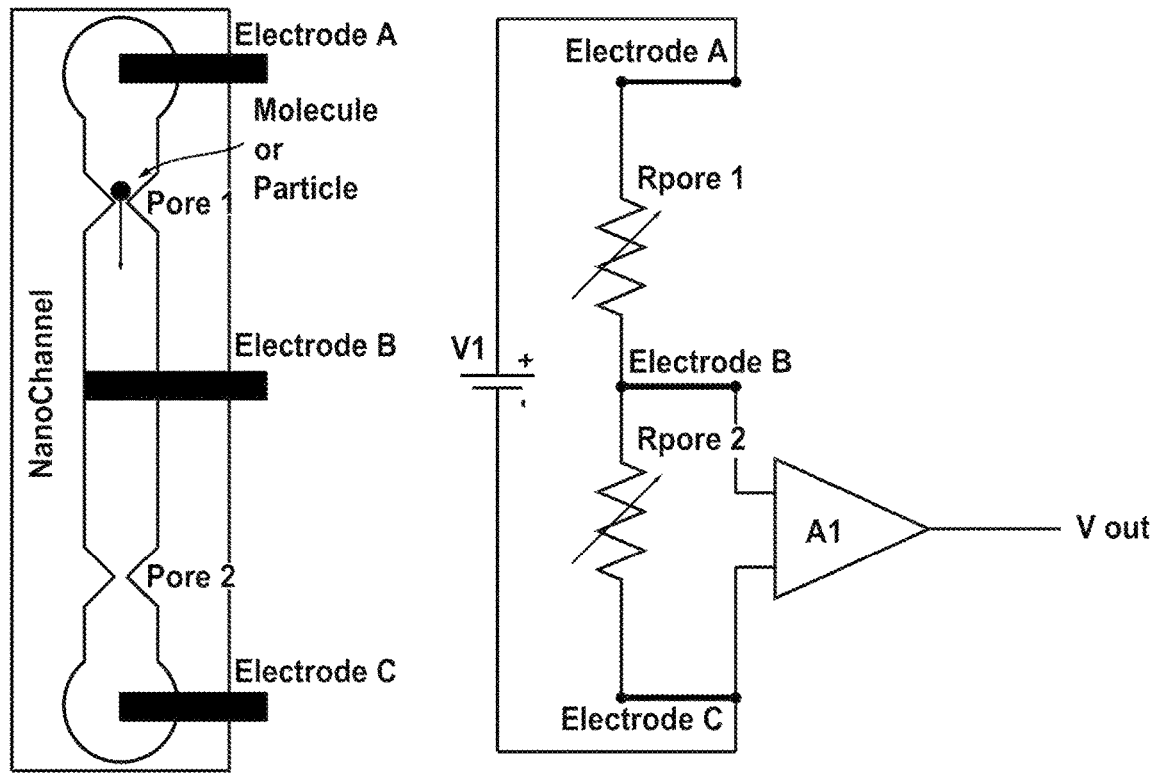
FIG. 21 shows a three-electrode system utilizing voltage measurement circuitry instead of current measuring circuitry. V1 provides the iontophoretic drive current while A1 (a voltage amplifier with high impedance inputs) measures voltage difference across Rpore2. A change in current at either pore will cause a potential change across the input of A1. Electrode C is the common, or return point for this circuit.
Figure 22:
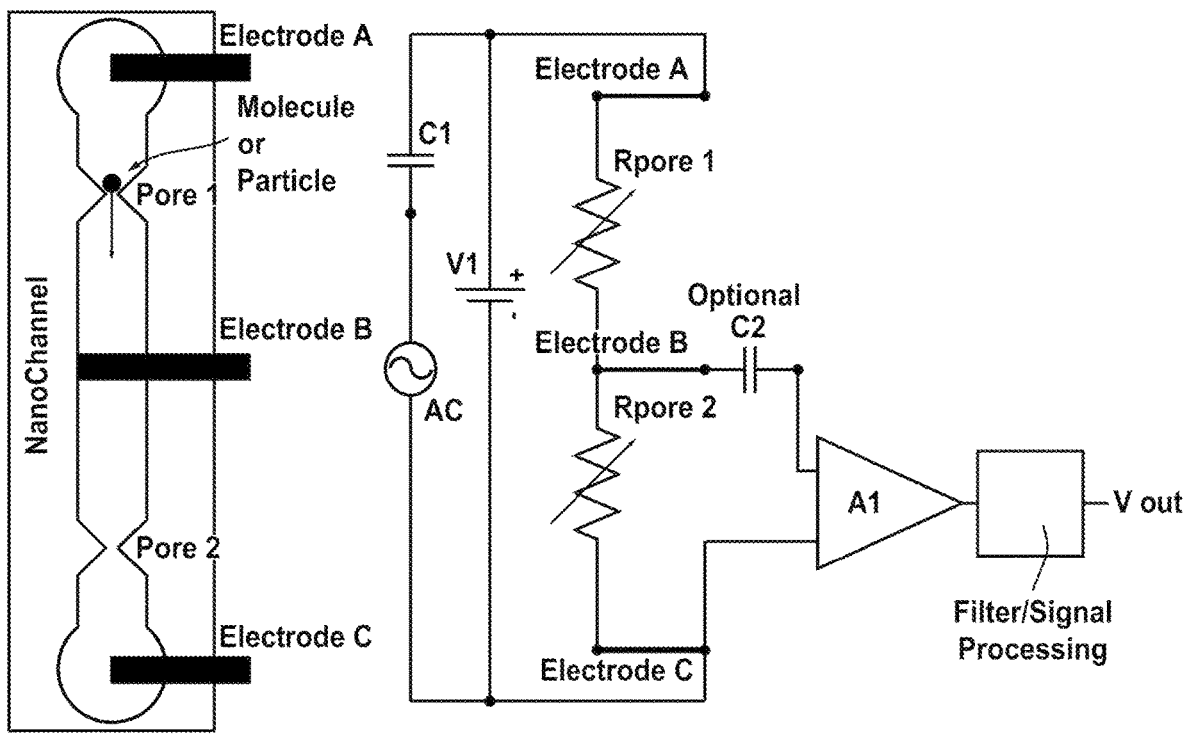
FIG. 22 shows a variation of the scheme in FIG. 21 showing the circuitry that allows DC and/or AC measurements of voltage changes. A1 can be either AC or DC coupled. DC coupling allows the measurement of both the AC and DC changes that result from blockade events.
Figure 23:
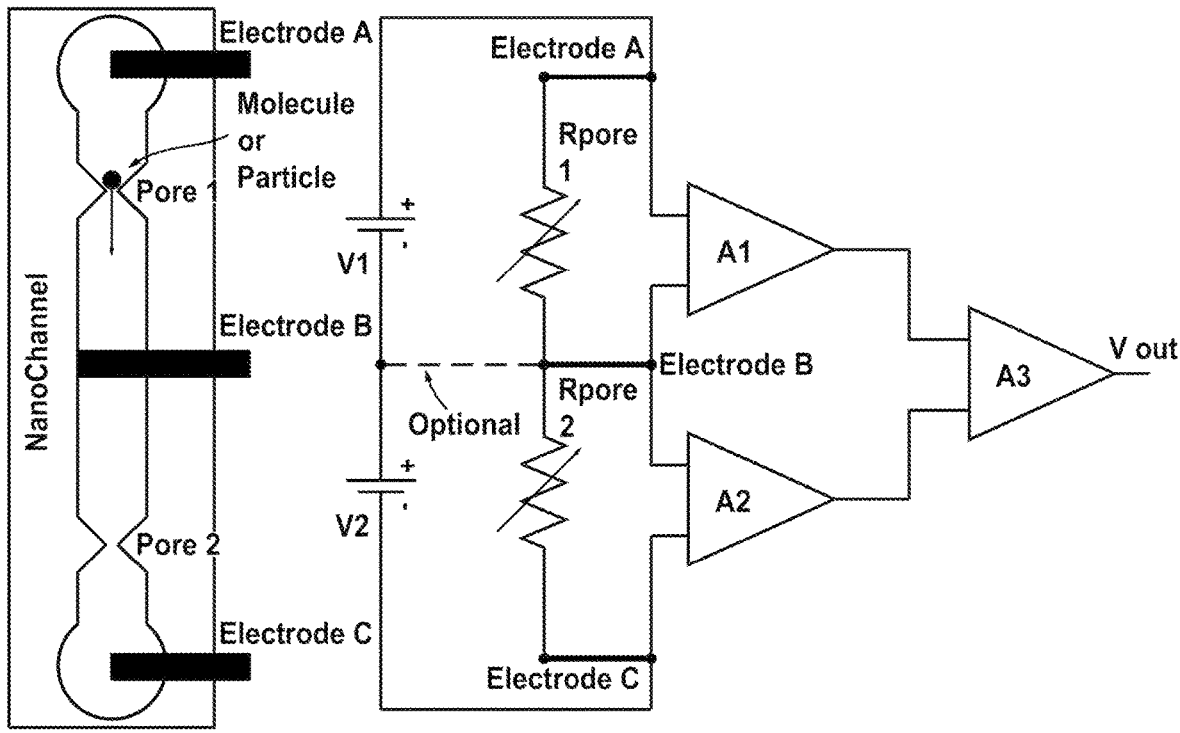
FIG. 23 illustrates a method of measuring the differential DC voltages across each of the pores. In this method, the polarity of blockade events is different for each of the two pores, thus allowing easy determination of the location of the blockage when the pores are of equal or similar size.
Figure 24:
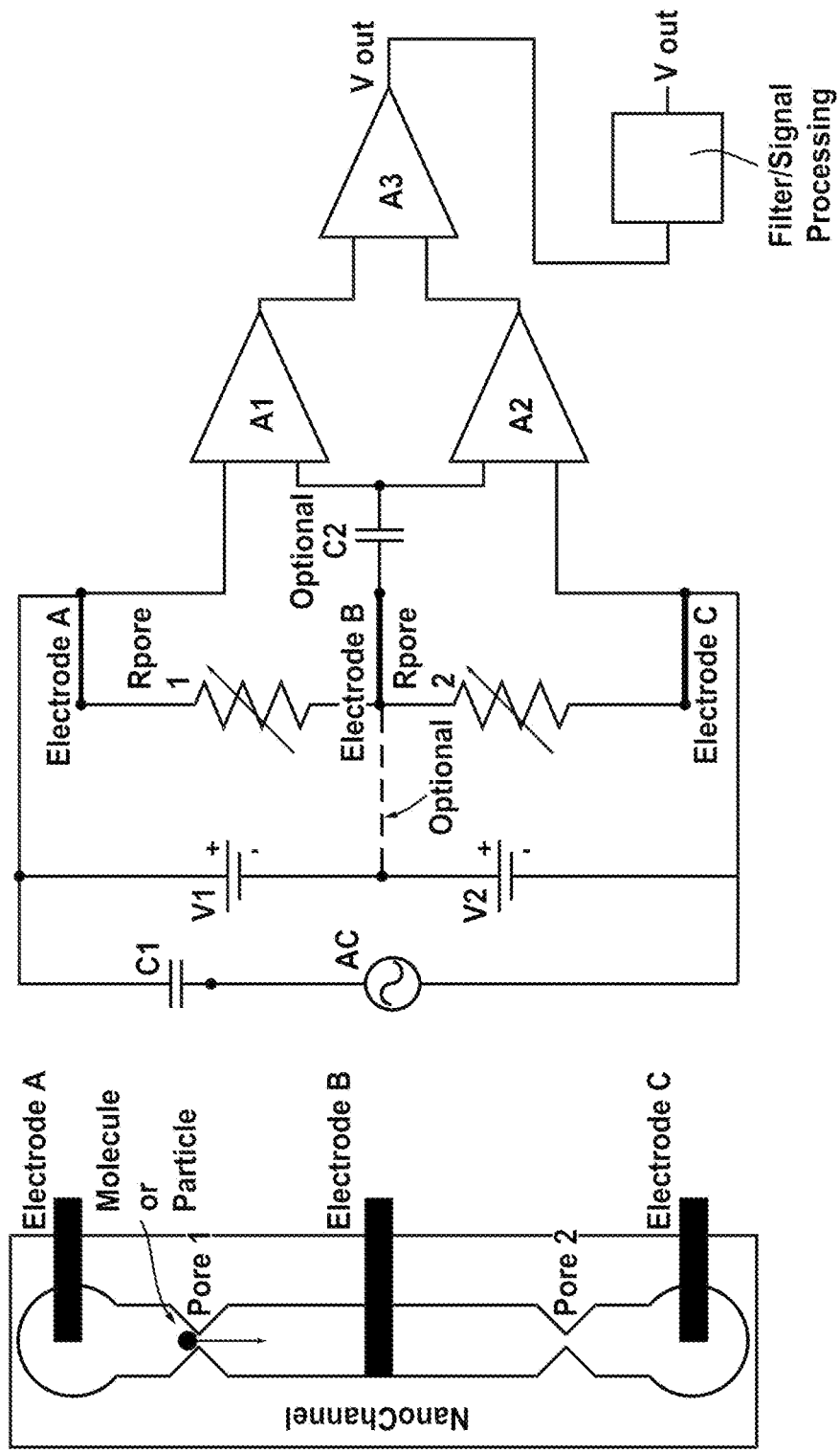
FIG. 24 illustrates the use of both AC and DC methods with the three electrode system employing a full differential amplifier topology. This topology retains all the advantages of the previous AC circuits while using voltage measuring circuitry.
Figure 25:
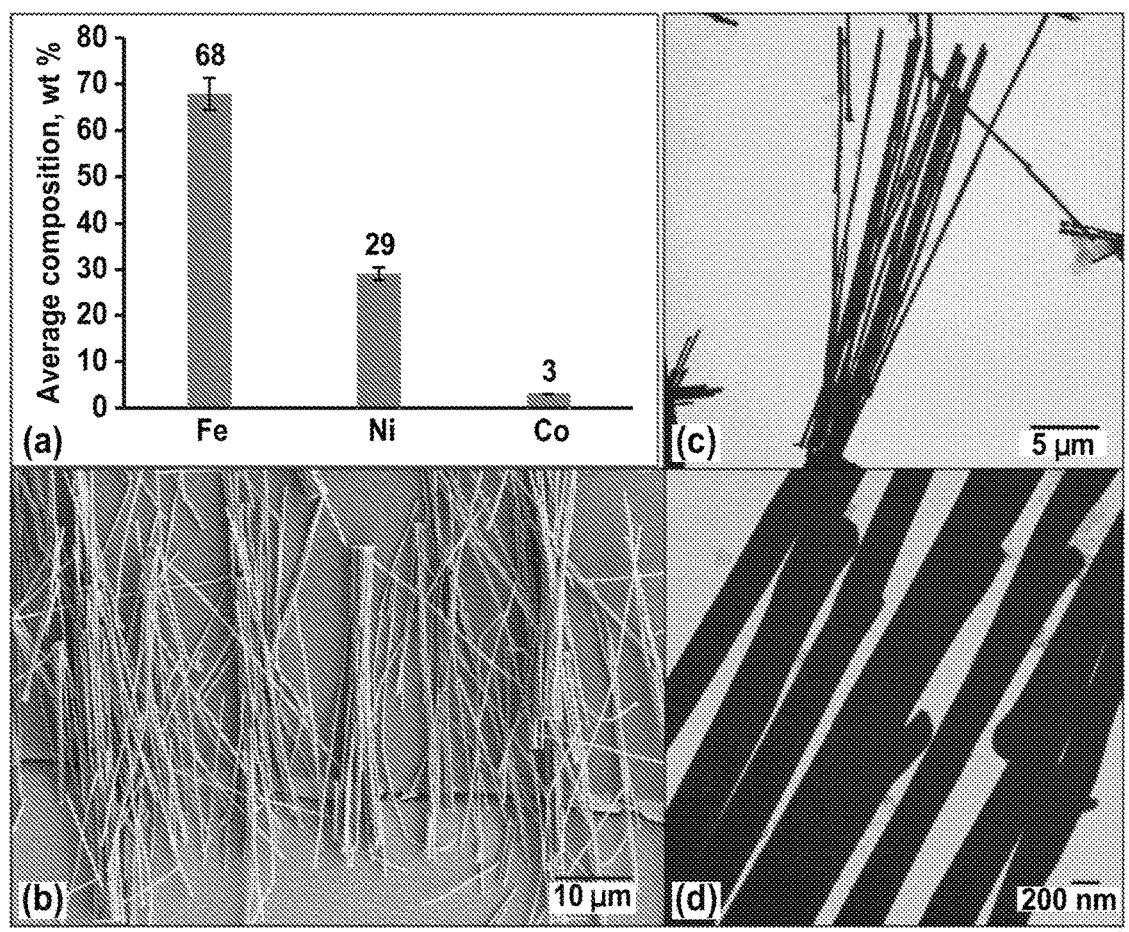
FIG. 25 shows the composition (panel a) and SEM and TEM images (panels b-d) of as deposited wires from a template with the template removed. These nanowire (coated with metals such as gold, platinum, silver, and copper) can be used as electrodes in the devices described herein.
Figure 26:
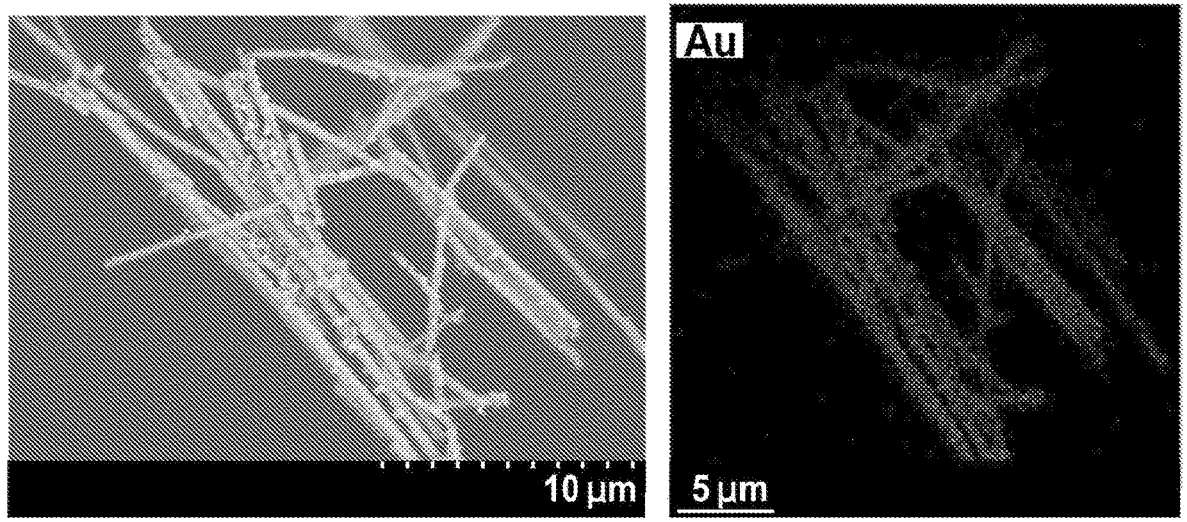
FIG. 26 shows an example of Fe—Ni—Co nanowires coated with gold; right side shows evidence that gold is indeed there (by EDS analysis).

Three electrodes can be used to provide a difference current or voltage between a common electrode and two other electrodes. If the common electrode is located so that it makes contact to the fluid in the nanochannel between the nanopores, then the measured signal from each pore will be of the opposite polarity with respect to the common electrode, thus allowing immediate identification of the pore at which a blockade event is occurring by its signal polarity. Several voltage detection methods have been described in the UMP patent application, including AC and DC-coupled differential voltage measurement techniques (FIGS. 20-24). In certain embodiments, a common reference between two power supplies is used. In these cases, the resulting difference current at the common electrode can be measured as shown in FIG. 20 below.

Signal Processing

All of the electronic circuit and electrode topologies discussed above will require some form of signal processing of the Vout signal to improve the signal-to-noise ratio (SNR) and to prepare the data for TOF calculation, including data compression techniques in hardware and software to reduce the total amount of data produced by each nanochannel. In addition, AI or machine learning algorithms can be used to interpret the data to improve the detection and identification of various particles based on "fingerprinting" and/or learning of the various attributes of the particles in a given nanochannel. Big Data Analytic techniques can be applied here as well. For systems using AC excitation, the phase and magnitude data can be utilized together to improve the statistics for detection and identification of particles by adding extra coherent orthogonal data. Hardware circuitry including threshold detection of blockade events along with sample/hold devices can be used to extract only the useful data out of a long stream of data. This would allow the TOF and amplitude of entry and exit of each particle to be extracted from a continuous stream of high speed analog data, thus allowing large numbers of parallel nanochannels to be accommodated with reasonable data streaming speeds and memory requirements.

Example 4: Nanowire Electrodes

Nanowires can also be used as the electrodes in the devices described herein. The conditions to create Fe—Ni—Co nano and micro-scale wires by electrodeposition have been determined. The nanowires can have a composition near the Invar range (Fe-rich composition, with a minor component of Co, difference Ni) that is expected to have a low coefficient of thermal expansion. Being inherently magnetic allows for the placement of the wires magnetically into the nano/micro fluidic regions of the device. They can also be used as a template for creating nanochannels through nanoimprinting. In particular, coating them with a noble metal (gold, silver, platinum, copper, etc.) enhances their resistivity and this coating doesn't necessarily need to completely cover the Fe—Ni—Co material but should form a contiguous path along the wire length.

FIG. 5: Machine Learning (ML) Algorithm for Data Analysis

Machine Learning (ML) can be used to assist in the identification of single molecules from the current transient signals and TOF data secured by our nanofluidic sensor. The current transient trace data contains characteristic signatures of the blockade events during a molecular translocation as well as the TOF information. Patterns in the current transients can supply information on various electronic properties of the single molecules that we will also evaluate via ML to classify the event. For example, the duration of the current transient can provide information as to the length of single DNA/RNA molecules or structure-dependent information for proteins, such as protein size, dipole moment, and/or volume.

Figure 29A:
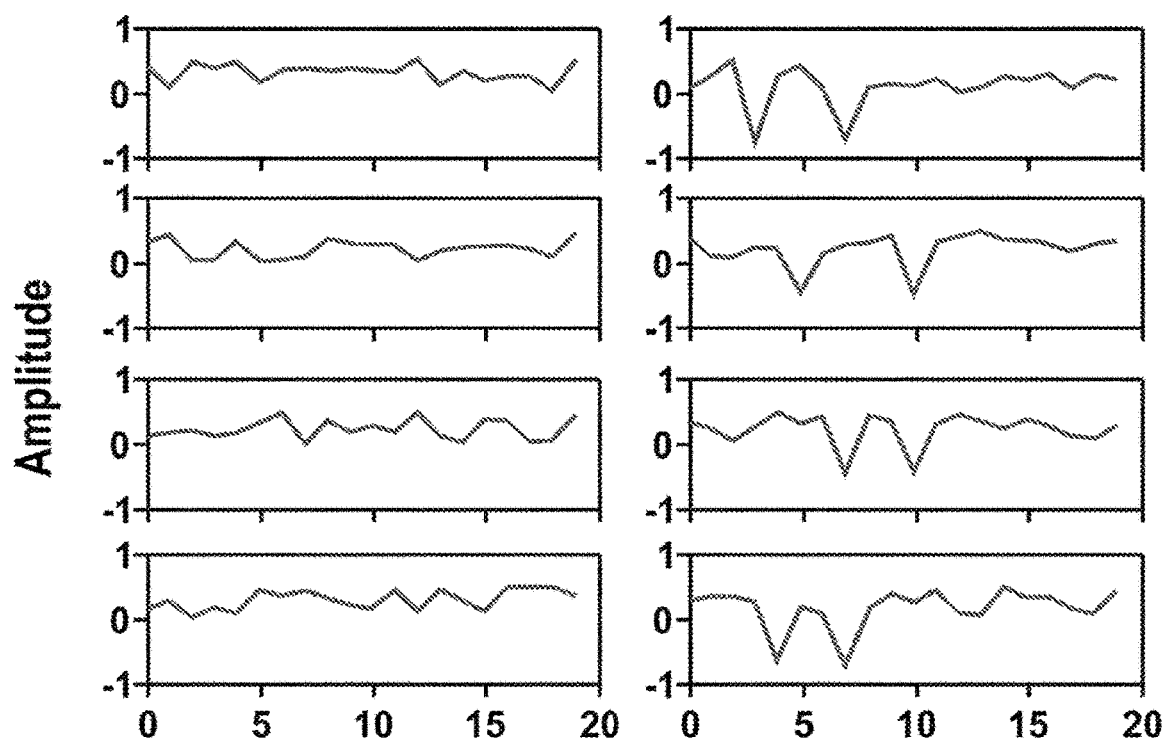
FIGS. 29A-29C show time-series data (time slices) showing non-event (column 1) and valid event examples (column 2) used to train the model. Time-series data identified as a two-peak event with 99.84% confidence (FIG. 29B) and 99.7% confidence (FIG. 29C) with reduced amplitudes.
Figure 29B:
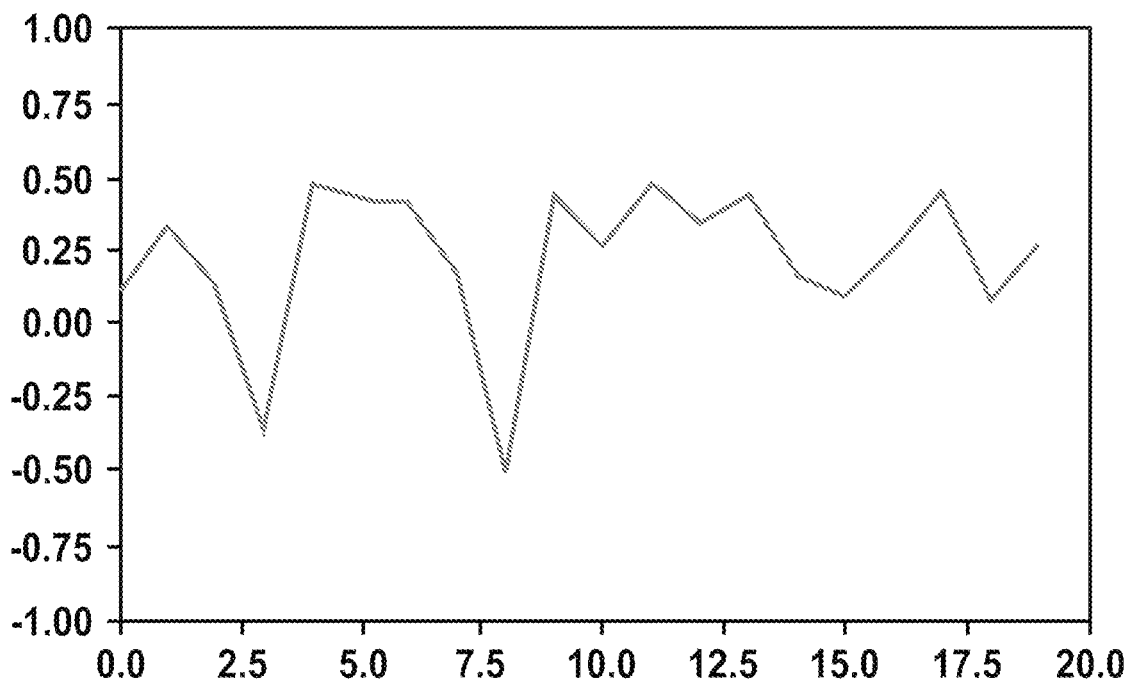
Figure 29C:
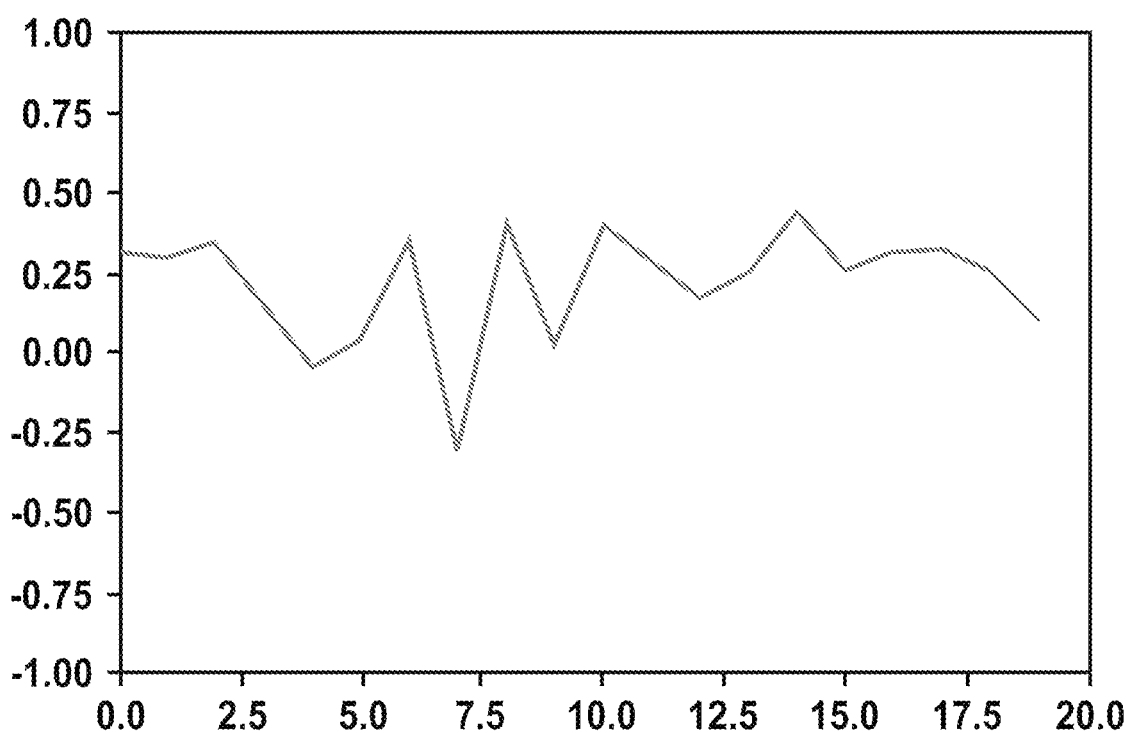

Initially, a binary classifier can be used to identify events in a time-series signal. The ML network was trained with labeled examples of non-events (background) and events (current transient peaks). FIG. 29A illustrates simulated training data sets showing non-events (left column) and valid events (right column) examples used to train the model. After training, the network was used to classify non-labeled examples as either a non-event or event with an associated confidence score (FIG. 29B). As can be seen in FIG. 29C, a peak pair embedded in high electrical noise background could be identified as a peak pair with 99.7% confidence. Later, the ML network will be expanded to support multiclass classification, allowing the detection and classification of single molecules.

Small ML models can be trained using local computing resources, but larger models are better trained on specialized hardware (GPUs) often available as cloud resources. After training, the network can be deployed in the cloud or local hardware, facilitating incorporation into either bench-top or portable instrumentation. Computation speeds in either the cloud, local hardware, or a combination of the two should allow near real-time classification.

The devices, systems, and methods of the appended claims are not limited in scope by the specific devices, systems, and methods described herein, which are intended as illustrations of a few aspects of the claims. Any devices, systems, and methods that are functionally equivalent are intended to fall within the scope of the claims. Various modifications of the devices, systems, and methods in addition to those shown and described herein are intended to fall within the scope of the appended claims. Further, while only certain representative devices, systems, and method steps disclosed herein are specifically described, other combinations of the devices, systems, and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. An analytical device comprising:
   (a) a sample processing region comprising two or more fluidically coupled sample handling elements defined by a substrate, wherein the two or more sample handling elements together affect a physical change on a sample introduced into the sample processing region; and
   (b) a first nanochannel formed in the substrate and fluidically coupled to the sample processing region, the first nanochannel comprising an input end of the first nanochannel, an output end of the first nanochannel, a first nanopore proximate to the input end of the first nanochannel, and a second nanopore spaced apart from the first nanopore and proximate to the output end of the first nanochannel, and
   (c) a second nanochannel coupled orthogonally with the first nanochannel, wherein the second nanochannel comprises an input end of the second nanochannel, an output end of the second nanochannel, a third nanopore proximate to the input end of the second nanochannel, and a fourth nanopore spaced apart from the third nanopore and proximate to the output end of the second nanochannel.

2. The device of claim 1, wherein the first nanochannel has a height of from greater than 10 nm to 500 nm, a width of from greater than 10 nm and up to 500 nm, a length of from 100 nm to 5 mm, or a combination thereof.

3. The device of claim 1, wherein the first nanopore, the second nanopore, or a combination thereof has a width and the first nanochannel has a width, and wherein the width of the first nanopore, the second nanopore, or a combination thereof is from 10% to 50% of the width of the first nanochannel, and/or
   wherein the first nanopore, the second nanopore, or a combination thereof has a height and the first nanochannel has a height, and wherein the height of the first nanopore, the second nanopore, or a combination thereof is from 10% to 50% of the height of the first nanochannel.

4. The device of claim 1, wherein the first nanopore has a width and the second nanopore has a width, and wherein the width of the first nanopore is different than the width of the second nanopore.

5. The device of claim 1, wherein the first nanochannel has a cross-sectional area, and the first nanopore, the second nanopore, or a combination thereof has a cross-sectional area; and wherein the cross-sectional area of the first nanopore, the second nanopore, or a combination thereof is 30% or less of the cross-sectional area of the first nanochannel.

6. The device of claim 1, wherein the first nanochannel further comprises a fifth nanopore disposed along the first nanochannel between the first nanopore and the second nanopore.

7. The device of claim 1, wherein the substrate is chosen from a thermoplastic, an elastomer, a paper, a ceramic, a glass, quartz, silicon, or a combination thereof.

8. The device of claim 1, further comprising a first electrode in electrical contact with the first nanochannel upstream of the first nanopore and a second electrode in electrical contact with the first nanochannel downstream of the second nanopore.

9. The device of claim 1, further comprising a third electrode in electrical contact with the first nanochannel downstream of the first nanopore and upstream of the second nanopore.

10. The device of claim 1, further comprising a third nanochannel fluidly connected to the nanochannel upstream of the first nanopore and a second electrode in electrical contact with the first nanochannel downstream of the second nanopore.

11. The device of claim 1, wherein the two or more fluidically coupled sample handling elements comprise an enrichment bed fluidically coupled to a microchannel.

12. The device of claim 1, wherein the two or more fluidically coupled sample handling elements together enrich concentration of an analyte present in the sample introduced into the sample processing region and/or purify an analyte present in the sample introduced into the sample processing region.

13. The device of claim 1, wherein the sample processing region comprises:
(i) a bioreactor chamber defined by the substrate;
(ii) a support structure within the bioreactor chamber and attached to the substrate; and
(iii) a cleaving enzyme immobilized to the support structure and operatively positioned within the bioreactor chamber to cleave monomer or multimer units of a biopolymer operatively engaged by the cleaving enzyme.

14. The device of claim 1, wherein the sample processing region further comprises an inlet channel defined by walls of the substrate, the inlet channel having a length extending from an input end proximate to a surface of the substrate to an output end fluidically connected to a bioreactor chamber.

15. The device of claim 1, further comprising an electric field generator operatively positioned to create an electric field in a bioreactor chamber and along the length of the first nanochannel.

16. The device of claim 1, wherein the first nanochannel comprises a hydrophobic surface.

17. The device of claim 16, wherein the second nanochannel comprises a charged surface.

18. A substrate wafer comprising a plurality of analytical devices each defined by claim 1.

* * * * *